US005866679A

United States Patent [19]
DeFeo-Jones et al.

[11] Patent Number: 5,866,679
[45] Date of Patent: *Feb. 2, 1999

[54] PEPTIDES

[75] Inventors: Deborah DeFeo-Jones, Lansdale; Victor M. Garsky, Blue Bell; Dong-Mei Feng, Harleysville; Raymond E. Jones, Lansdale; Allen I. Oliff, Gwynedd Valley, all of Pa.

[73] Assignee: Merck & Co., Inc., Rahway, N.J.

[*] Notice: This patent issued on a continued prosecution application filed under 37 CFR 1.53(d), and is subject to the twenty year patent term provisions of 35 U.S.C. 154(a)(2).

The term of this patent shall not extend beyond the expiration date of Pat. No. 5,599,686.

[21] Appl. No.: 540,412

[22] Filed: Oct. 6, 1995

Related U.S. Application Data

[63] Continuation-in-part of Ser. No. 468,161, Jun. 6, 1995, which is a continuation-in-part of Ser. No. 404,833, Mar. 15, 1995, abandoned, which is a continuation-in-part of Ser. No. 267,092, Jun. 28, 1994, Pat. No. 5,599,686.

[51] Int. Cl.$^6$ .............................. C07K 5/09; A61K 38/00
[52] U.S. Cl. ......................... 530/322; 530/324; 530/326; 530/328; 530/329; 514/14; 514/15; 514/13; 514/12; 514/16; 514/17
[58] Field of Search ................................. 530/324, 326, 530/328, 329, 322; 514/14, 15, 13, 12, 16, 17

[56] References Cited

U.S. PATENT DOCUMENTS

| | | | |
|---|---|---|---|
| 4,277,466 | 7/1981 | Trouet | 424/185.1 |
| 4,296,105 | 10/1981 | Baurain et al. | 424/185.1 |
| 4,388,305 | 6/1983 | Trouet et al. | 424/185.1 |
| 4,446,122 | 5/1984 | Chu et al. | 435/4 |
| 4,703,107 | 10/1987 | Monsigny et al. | 530/330 |
| 4,753,984 | 6/1988 | Delmotte et al. | 525/54.1 |
| 4,828,831 | 5/1989 | Hannart et al. | 424/185.1 |
| 4,870,162 | 9/1989 | Trouet et al. | 530/363 |
| 5,024,835 | 6/1991 | Rao et al. | 514/8 |
| 5,030,620 | 7/1991 | Hannart et al. | 514/8 |
| 5,220,001 | 6/1993 | Ok et al. | 536/6.4 |
| 5,288,612 | 2/1994 | Griffin et al. | 435/23 |
| 5,349,066 | 9/1994 | Kaneko et al. | 546/294 |
| 5,391,723 | 2/1995 | Priest | 536/23.1 |
| 5,599,685 | 2/1997 | DeFeo-Jones et al. | 435/23 |

FOREIGN PATENT DOCUMENTS

| | | |
|---|---|---|
| 0 126 344 A2 | 11/1984 | European Pat. Off. |
| 0 554 708 A1 | 8/1993 | European Pat. Off. |
| 0 590 530 A2 | 4/1994 | European Pat. Off. |
| 2 678 274 A1 | 12/1992 | France |
| WO 92/01936 | 2/1992 | WIPO |
| WO 94/03594 | 2/1994 | WIPO |
| WO 94/10343 | 5/1994 | WIPO |
| WO 94/20114 | 9/1994 | WIPO |
| WO 95/30758 | 11/1995 | WIPO |
| WO 9605863A1 | 2/1996 | WIPO |

OTHER PUBLICATIONS

Proc. Natl. Acad. Sci. USA, vol. 83, pp. 3166–3170 (1986) Biochemistry, by Watt, et al.
Eur. J. Biochem., vol. 194, pp. 755–763 (1990), by Christensson, et al.
J. Med. Chem, vol. 26, pp. 633–638 (1983), by Chakravarty, et al.
J. of Med. Chem, vol. 26, No. 5, pp. 638–644 (1983), by Chakravarty, et al.
Eur. J. Biochem, vol. 95, pp. 115–119 (1979), by Pozsgay, et al.
Anal. Biochem., vol. 193, pp. 248–255 (1991), by Harnois–Pontoni, et al.
J. Med. Chem., vol. 34, pp. 3029–3035 (1991), by Mayer, et al.
Trail, P.A. et al., "Cure of Xenografted Human Carcinomas by BR96–Doxorubicin Immunoconjugate," Science, vol. 261, pp. 212–215 (1993).
Willner, D. et al., "(6–Maleimidocaproyl)hydrazone of Doxorubicin–A New Derivative for the Preparation of Immunoconjugates of Doxorubicin, Bioconjugate," Chem., col. 4, pp. 521–527 (1993).
Yu, H., et al., "Immunoreactive Prostate–Specific Antigen Levels in Female and Male Breast Tumors and its Association with Steroid Hormone Receptors and Paient Age." Clinical Biochemistry, vol. 27, pp. 75–79 (1994).
Rao, K.S.P.B. et al., "Vinblastin–23–oyl Amino Acid Derivatives: Chemistry, Physiochemical Data, Toxicity, and Antitumor Activities against P388 and L1210 Leukemias," Jour. Med. Chem., vol. 28, pp. 1079–1088 (1985).
Barnett, C.J., et al., "Structure–Activity Relationships of Dimeric Catharanthus Alkaloids. 1. Deacetylyinblastine Amide (Vindesine) Sulfate," Jour. Med. Chem., vol. 21, No. 1 (1978).
Lilja, H. et al., "Semenogelin, the Predominant Protein in Human Semen," Jour. of Biol. Chem., vol. 264, No. 3, pp. 1894–1900 (1989).
Lilja, H. and Lundwall, A., "Molecular cloning of epididymal and seminal vesicular transcripts encoding a semenogelin–related protein," Proc. Natl. Acad., Sci, USA, Biochem., vol. 89, pp. 4559–4563 (1992).

*Primary Examiner*—Cecilia Tsang
*Assistant Examiner*—S. G. Marshall
*Attorney, Agent, or Firm*—David A. Muthard; Mark R. Daniel

[57] ABSTRACT

Oligopeptides which comprise amino acid sequences that are recognized and proteolytically cleaved by free prostate specific antigen (PSA) are described. Also described are assays which comprise such oligopeptides useful for determining free PSA protease activity in vitro and in vivo. Therapeutic agents which comprise conjugates of such oligopeptides and known cytotoxic agents are also described.

18 Claims, 12 Drawing Sheets

1: MetLysProAsnIleIlePheValLeuSerLeuLeuLeuIleLeuGluLysGlnAlaAla –

21: ValMetGlyGlnLysGlyGlySerLysGlyArgLeuProSerGluPheSerGlnPhePro –

41: HisGlyGlnLysGlyGlnHisTyrSerGlyGlnLysGlyLysGlnGlnThrGluSerLys –

61: GlySerPheSerIleGlnTyrThrTyrHisValAspAlaAsnAspHisAspGlnSerArg –

81: LysSerGlnGlnTyrAspLeuAsnAlaLeuHisLysThrThrLysSerGlnArgHisLeu –

101: GlyGlySerGlnGlnLeuLeuHisAsnLysGlnGluGlyArgAspHisAspLysSerLys –

121: GlyHisPheHisArgValValIleHisHisLysGlyGlyLysAlaHisArgGlyThrGln –

CS#5

141 AsnProSerGlnAspGlyGlyAsnSerProSerGlyLysGlyIleSerSerGlnThr|Ser –

161: AsnThrGluGluArgLeuTrpValHisGlyLeuSerLysGluGlnThrSerValSerGly –

181: AlaGlnLysGlyArgLysGlnGlyGlySerGlnSerSerTyrValLeuGlnThrGluGlu –

201: LeuValAlaAsnLysGlnGlnArgGluThrLysAsnSerHisGlnAsnLysGlyHisTyr –

221: GlnAsnValValGluValArgGluGluHisSerSerLysValGlnThrSerLeuCysPro –

241: AlaHisGlnAspLysLeuGlnHisGlySerLysAspIlePheSerThrGlnAspGluLeu –

FIG. 1

261: LeuValTyrAsnLysAsnGlnHisGlnThrLysAsnLeuAsnGlnAspGlnGlnHisGly —

CS#3

281: ArgLysAlaAsnLysIleSerTyrGln|SerSerSerThrGluGluArgArgLeuHisTyr —

CS#4

301: GlyGluAsnGlyValGlnLysAspValSerGlnSerSerIleTyrSer|GlnThrGluGlu —

321: LysAlaGlnGlyLysSerGlnLysGlnIleThrIleProSerGlnGluGlnGluHisSer —

CS#1

341: GlnLysAlaAsnLysIleSerTyrGln|SerSerSerThrGluGluArgArgLeuHisTyr —

CS#2

361: GlyGluAsnGlyValGlnLysAspValSerGlnArgSerIleTyrSer|GlnThrGluLys —

381: LeuValAlaGlyLysSerGlnIleGlnAlaProAsnProLysGlnGluProTrpHisGly —

401: GluAsnAlaLysGlyGluSerGlyGlnSerThrAsnArgGluGlnAspLeuLeuSerHis —

421: GluGlnLysGlyArgHisGlnHisGlySerHisGlyGlyLeuAspIleValIleIleGlu —

441: GlnGluAspAspSerAspArgHisLeuAlaGlnHisLeuAsnAsnAspArgAsnProLeu —

461: PheThr —

FIG. 1A

| PERCENT PEPTIDE HYDROLYSIS | | | | | | |
|---|---|---|---|---|---|---|
| | TIME OF INCUBATION (HOURS) | | | | | |
| PEPTIDE | 0.5 | 1 | 2 | 3 | 4 | 20 |
| 1. SYQSSSTE | ND | 0 | ND | 0 | ND | 0 |
| 2. ISYQSSSTE | ND | 0 | ND | 0 | ND | 0 |
| 3. KISYQSSSTE | ND | 10 | ND | 30 | ND | 90 |
| 4. NKISYQSSSTE | ND | 30 | ND | 70 | ND | 100 |
| 5. NKISYQSSST | ND | 20 | 30 | ND | ND | 100 |
| 6. ANKISYQSSSTE | 15 | 25 | ND | ND | 80 | 100 |
| 7. ANKISYQSSS | 4 | 6 | 16 | 30 | 45 | ND |
| 8. NKISYQSSS | 2 | 6 | 22 | 44 | 55 | ND |
| 9. ANKISYQSS | 1 | ND | 12 | ND | 39 | ND |
| 10. GRKANKISYQS-SSTEERRLHYGENG | 20 | 50 | ND | ND | 90 | 100 |

ND = not determined
The single letter code for amino acids is used: A=Ala, E=Glu, G=Gly, H=His, I=Ile, K=Lys, L=Leu, N=Asn, Q=Gln, R=Arg, S=Ser, T=Thr, Y=Tyr

FIG.2

SEQUENCE LISTING ( 1 ) GENERAL INFORMATION:

( i i i ) NUMBER OF SEQUENCES: 194

( 2 ) INFORMATION FOR SEQ ID NO:1:

( i ) SEQUENCE CHARACTERISTICS:
        ( A ) LENGTH: 462 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:1:

```
Met  Lys  Pro  Asn  Ile  Ile  Phe  Val  Leu  Ser  Leu  Leu  Leu  Ile  Leu  Glu
 1              5                        10                       15

Lys  Gln  Ala  Ala  Val  Met  Gly  Gln  Lys  Gly  Gly  Ser  Lys  Gly  Arg  Leu
              20                       25                       30

Pro  Ser  Glu  Phe  Ser  Gln  Phe  Pro  His  Gly  Gln  Lys  Gly  Gln  His  Tyr
              35                       40                       45

Ser  Gly  Gln  Lys  Gly  Lys  Gln  Gln  Thr  Glu  Ser  Lys  Gly  Ser  Phe  Ser
         50                       55                       60
```

| Ile | Gln | Tyr | Thr | Tyr | His | Val | Asp | Ala | Asn | Asp | His | Asp | Gln | Ser | Arg |
| 65 | | | | 70 | | | | | 75 | | | | | | 80 |
| Lys | Ser | Gln | Gln | Tyr | Asp | Leu | Asn | Ala | Leu | His | Lys | Thr | Thr | Lys | Ser |
| | | | | 85 | | | | | 90 | | | | | 95 | |
| Gln | Arg | His | Leu | Gly | Gly | Ser | Gln | Leu | Leu | His | Asn | Lys | Gln | Glu | |
| | | | 100 | | | | | 105 | | | | | 110 | | |
| Gly | Arg | Asp | His | Asp | Lys | Ser | Lys | Gly | His | Phe | His | Arg | Val | Val | Ile |
| | | | 115 | | | | | 120 | | | | 125 | | | |
| His | His | Lys | Gly | Gly | Lys | Ala | His | Arg | Gly | Thr | Gln | Asn | Pro | Ser | Gln |
| | 130 | | | | | 135 | | | | | 140 | | | | |
| Asp | Gln | Gly | Asn | Ser | Pro | Ser | Gly | Lys | Gly | Ile | Ser | Ser | Gln | Tyr | Ser |
| 145 | | | | | 150 | | | | | 155 | | | | | 160 |
| Asn | Thr | Glu | Glu | Arg | Leu | Trp | Val | His | Gly | Leu | Ser | Lys | Glu | Gln | Thr |
| | | | | 165 | | | | | 170 | | | | | 175 | |
| Ser | Val | Ser | Gly | Ala | Gln | Lys | Gly | Arg | Lys | Gln | Gly | Gly | Ser | Gln | Ser |
| | | | 180 | | | | | 185 | | | | | 190 | | |
| Ser | Tyr | Val | Leu | Gln | Thr | Glu | Glu | Leu | Val | Ala | Asn | Lys | Gln | Gln | Arg |
| | | 195 | | | | | 200 | | | | | 205 | | | |
| Glu | Thr | Lys | Asn | Ser | His | Gln | Asn | Lys | Gly | His | Tyr | Gln | Asn | Val | Val |
| | 210 | | | | | 215 | | | | | 220 | | | | |
| Glu | Val | Arg | Glu | Glu | His | Ser | Ser | Lys | Val | Gln | Thr | Ser | Leu | Cys | Pro |
| 225 | | | | | 230 | | | | | 235 | | | | | 240 |
| Ala | His | Gln | Asp | Lys | Leu | Gln | His | Gly | Ser | Lys | Asp | Ile | Phe | Ser | Thr |
| | | | | 245 | | | | | 250 | | | | | 255 | |
| Gln | Asp | Glu | Leu | Leu | Val | Tyr | Asn | Lys | Asn | Gln | His | Gln | Thr | Lys | Asn |
| | | | 260 | | | | | 265 | | | | | 270 | | |
| Leu | Asn | Gln | Asp | Gln | His | Gly | Arg | Lys | Ala | Asn | Lys | Ile | Ser | Tyr | |
| | | 275 | | | | | 280 | | | | | 285 | | | |
| Gln | Ser | Ser | Thr | Glu | Glu | Arg | Arg | Leu | His | Tyr | Gly | Glu | Asn | Gly | |
| | 290 | | | | | 295 | | | | | 300 | | | | |
| Val | Gln | Lys | Asp | Val | Ser | Gln | Ser | Ser | Ile | Tyr | Ser | Gln | Thr | Glu | Glu |
| 305 | | | | | 310 | | | | | 315 | | | | | 320 |
| Lys | Ala | Gln | Gly | Lys | Ser | Gln | Lys | Gln | Ile | Thr | Ile | Pro | Ser | Gln | Glu |
| | | | | 325 | | | | | 330 | | | | | 335 | |
| Gln | Glu | His | Ser | Gln | Lys | Ala | Asn | Lys | Ile | Ser | Tyr | Gln | Ser | Ser | Ser |
| | | | 340 | | | | | 345 | | | | | 350 | | |
| Thr | Glu | Glu | Arg | Arg | Leu | His | Tyr | Gly | Glu | Asn | Gly | Val | Gln | Lys | Asp |
| | | | 355 | | | | | 360 | | | | | 365 | | |
| Val | Ser | Gln | Arg | Ser | Ile | Tyr | Ser | Gln | Thr | Glu | Lys | Leu | Val | Ala | Gly |
| | | 370 | | | | | 375 | | | | | 380 | | | |
| Lys | Ser | Gln | Ile | Gln | Ala | Pro | Asn | Pro | Lys | Gln | Glu | Pro | Trp | His | Gly |
| 385 | | | | | 390 | | | | | 395 | | | | | 400 |
| Glu | Asn | Ala | Lys | Gly | Glu | Ser | Gly | Gln | Ser | Thr | Asn | Arg | Glu | Gln | Asp |
| | | | | 405 | | | | | 410 | | | | | 415 | |
| Leu | Leu | Ser | His | Glu | Gln | Lys | Gly | Arg | His | Gln | His | Gly | Ser | His | Gly |
| | | | 420 | | | | | 425 | | | | | 430 | | |
| Gly | Leu | Asp | Ile | Val | Ile | Ile | Glu | Gln | Glu | Asp | Asp | Ser | Asp | Arg | His |
| | | 435 | | | | | 440 | | | | | 445 | | | |
| Leu | Ala | Gln | His | Leu | Asn | Asn | Asp | Arg | Asn | Pro | Leu | Phe | Thr | | |
| | 450 | | | | | 455 | | | | | 460 | | | | |

( 2 ) INFORMATION FOR SEQ ID NO:2:

( i ) SEQUENCE CHARACTERISTICS:

( A ) LENGTH: 15 amino acids (B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:2:

```
Gly Lys Gly Ile Ser Ser Gln Tyr Ser Asn Thr Glu Glu Arg Leu
1               5                   10                  15
```

(2) INFORMATION FOR SEQ ID NO:3:

(i) SEQUENCE CHARACTERISTICS:
(A) LENGTH: 11 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:3:

```
Asn Lys Ile Ser Tyr Gln Ser Ser Ser Thr Glu
1               5                   10
```

(2) INFORMATION FOR SEQ ID NO:4:

(i) SEQUENCE CHARACTERISTICS:
(A) LENGTH: 19 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:4:

```
Gly Glu Asn Gly Val Gln Lys Asp Val Ser Gln Arg Ser Ile Tyr Ser
1               5                   10                  15

Gln Thr Glu
```

(2) INFORMATION FOR SEQ ID NO:5:

(i) SEQUENCE CHARACTERISTICS:
(A) LENGTH: 19 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (x i) SEQUENCE DESCRIPTION: SEQ ID NO:5:

Gly Glu Asn Gly Val Gln Lys Asp Val Ser Gln Ser Ser Ile Tyr Ser
1               5                   10                  15

Gln Thr Glu (2) INFORMATION FOR SEQ ID NO:6:

(i) SEQUENCE CHARACTERISTICS:
    (A) LENGTH: 25 amino acids
    (B) TYPE: amino acid
    (C) STRANDEDNESS: single
    (D) TOPOLOGY: linear (i i) MOLECULE TYPE: peptide (i i i) HYPOTHETICAL: NO (i v) ANTI-SENSE: NO (v) FRAGMENT TYPE: internal (x i) SEQUENCE DESCRIPTION: SEQ ID NO:6:

Gly Arg Lys Ala Asn Lys Ile Ser Tyr Gln Ser Ser Thr Glu Glu
1               5                   10                  15

Arg Arg Leu His Tyr Gly Glu Asn Gly
            20              25

(2) INFORMATION FOR SEQ ID NO:7:

(i) SEQUENCE CHARACTERISTICS:
    (A) LENGTH: 8 amino acids
    (B) TYPE: amino acid
    (C) STRANDEDNESS: single
    (D) TOPOLOGY: linear (i i) MOLECULE TYPE: peptide (i i i) HYPOTHETICAL: NO (i v) ANTI-SENSE: NO (v) FRAGMENT TYPE: internal (x i) SEQUENCE DESCRIPTION: SEQ ID NO:7:

Ser Tyr Gln Ser Ser Ser Thr Glu
1               5

(2) INFORMATION FOR SEQ ID NO:8:

(i) SEQUENCE CHARACTERISTICS:
    (A) LENGTH: 9 amino acids
    (B) TYPE: amino acid
    (C) STRANDEDNESS: single
    (D) TOPOLOGY: linear (i i) MOLECULE TYPE: peptide (i i i) HYPOTHETICAL: NO (i v) ANTI-SENSE: NO (v) FRAGMENT TYPE: internal (x i) SEQUENCE DESCRIPTION: SEQ ID NO:8:

Ile Ser Tyr Gln Ser Ser Ser Thr Glu
1               5

(2) INFORMATION FOR SEQ ID NO:9:

(i) SEQUENCE CHARACTERISTICS:

(A) LENGTH: 10 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:9:

Lys Ile Ser Tyr Gln Ser Ser Ser Thr Glu
1               5                   10

(2) INFORMATION FOR SEQ ID NO:10:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:10:

Asn Lys Ile Ser Tyr Gln Ser Ser Ser Thr
1               5                   10

(2) INFORMATION FOR SEQ ID NO:11:

(i) SEQUENCE CHARACTERISTICS:
(A) LENGTH: 12 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:11:

Ala Asn Lys Ile Ser Tyr Gln Ser Ser Ser Thr Glu
1               5                   10

(2) INFORMATION FOR SEQ ID NO:12:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:12:

```
Ala  Gly  Pro  Thr  Gly  Ala  Ser  Ala
1                  5
```

(2) INFORMATION FOR SEQ ID NO:13:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:13:

```
Asn  Lys  Ile  Ser  Tyr  Gln  Ser
1                  5
```

(2) INFORMATION FOR SEQ ID NO:14:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:14:

```
Lys  Ile  Ser  Tyr  Gln  Ser
1                  5
```

(2) INFORMATION FOR SEQ ID NO:15:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Peptide
        (B) LOCATION: 12
        (D) OTHER INFORMATION: /note= "any natural amino acid"

(xi) SEQUENCE DESCRIPTION: SEQ ID NO:15:

```
Gly  Glu  Asn  Gly  Val  Gln  Lys  Asp  Val  Ser  Gln  Xaa  Ser  Ile  Tyr  Ser
1                  5                            10                           15
Gln  Thr  Glu
```

(2) INFORMATION FOR SEQ ID NO:16:

( i ) SEQUENCE CHARACTERISTICS:
  ( A ) LENGTH: 8 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:16:

Asn Lys Ile Ser Tyr Gln Ser Ser
1               5

( 2 ) INFORMATION FOR SEQ ID NO:17:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:17:

Asn Lys Ile Ser Tyr Gln Ser Ser Ser
1               5

( 2 ) INFORMATION FOR SEQ ID NO:18:

( i ) SEQUENCE CHARACTERISTICS:
    ( A ) LENGTH: 10 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:18:

Ala Asn Lys Ile Ser Tyr Gln Ser Ser Ser
1               5                   10

( 2 ) INFORMATION FOR SEQ ID NO:19:

( i ) SEQUENCE CHARACTERISTICS:
    ( A ) LENGTH: 10 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:19:

Lys Ile Ser Tyr Gln Ser Ser Ser Thr Glu
1               5                   10

( 2 ) INFORMATION FOR SEQ ID NO:20:

( i ) SEQUENCE CHARACTERISTICS:
      ( A ) LENGTH: 17 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:20:

Gln Leu Asp Asn Lys Ile Ser Tyr Gln Ser Ser Thr His Gln Ser
1               5                   10                  15

Ser ( 2 ) INFORMATION FOR SEQ ID NO:21:

( i ) SEQUENCE CHARACTERISTICS:
      ( A ) LENGTH: 7 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:21:

Asn Arg Ile Ser Tyr Gln Ser
1               5

( 2 ) INFORMATION FOR SEQ ID NO:22:

( i ) SEQUENCE CHARACTERISTICS:
      ( A ) LENGTH: 7 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:22:

Asn Lys Val Ser Tyr Gln Ser
1               5

( 2 ) INFORMATION FOR SEQ ID NO:23:

( i ) SEQUENCE CHARACTERISTICS:
      ( A ) LENGTH: 8 amino acids
      ( B ) TYPE: amino acid
      ( C ) STRANDEDNESS: single (D) TOPOLOGY: linear (ii) MOLECULE TYPE: protein (iii) HYPOTHETICAL: NO (iv) ANTI-SENSE: NO (v) FRAGMENT TYPE: internal (xi) SEQUENCE DESCRIPTION: SEQ ID NO:23:

Asn Lys Met Ser Tyr Gln Ser Ser
1               5

(2) INFORMATION FOR SEQ ID NO:24:

(i) SEQUENCE CHARACTERISTICS:
    (A) LENGTH: 8 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:24:

Asn Lys Leu Ser Tyr Gln Ser Ser
1               5

(2) INFORMATION FOR SEQ ID NO:25:

(i) SEQUENCE CHARACTERISTICS:
    (A) LENGTH: 9 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:25:

Asn Lys Ile Thr Tyr Gln Ser Ser Ser
1               5

(2) INFORMATION FOR SEQ ID NO:26:

(i) SEQUENCE CHARACTERISTICS:
    (A) LENGTH: 9 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:26:

Asn Lys Ile Ser Phe Gln Ser Ser Ser
1               5

( 2 ) INFORMATION FOR SEQ ID NO:27:

( i ) SEQUENCE CHARACTERISTICS:
      ( A ) LENGTH: 10 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:27:

Asn Lys Ile Ser Trp Gln Ser Ser Ser Thr
   1               5                   10

( 2 ) INFORMATION FOR SEQ ID NO:28:

( i ) SEQUENCE CHARACTERISTICS:
      ( A ) LENGTH: 10 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:28:

Asn Lys Ile Ser Tyr Asn Ser Ser Ser Thr
   1               5                   10

( 2 ) INFORMATION FOR SEQ ID NO:29:

( i ) SEQUENCE CHARACTERISTICS:
      ( A ) LENGTH: 10 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:29:

Asn Lys Ile Ser Tyr Gln Thr Ser Ser Thr
   1               5                   10

( 2 ) INFORMATION FOR SEQ ID NO:30:

( i ) SEQUENCE CHARACTERISTICS:
      ( A ) LENGTH: 7 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO (iv) ANTI-SENSE: NO (v) FRAGMENT TYPE: internal (xi) SEQUENCE DESCRIPTION: SEQ ID NO:30:

Asn Lys Ile Ser Tyr Gln Ser
1               5

(2) INFORMATION FOR SEQ ID NO:31:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:31:

Gln Lys Ile Ser Tyr Gln Ser Ser
1               5

(2) INFORMATION FOR SEQ ID NO:32:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:32:

Asn Arg Ile Thr Tyr Gln Ser Ser Ser
1               5

(2) INFORMATION FOR SEQ ID NO:33:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:33:

Asn Arg Ile Ser Phe Gln Ser Ser Ser Thr
1               5                   10

(2) INFORMATION FOR SEQ ID NO:34:

(i) SEQUENCE CHARACTERISTICS:
        (A) LENGTH: 10 amino acids ( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:34:

Gln Lys Ile Ser Tyr Gln Thr Ser Ser Thr
1               5                   10

( 2 ) INFORMATION FOR SEQ ID NO:35:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:35:

Asn Arg Ile Ser Trp Gln Ser Ser Ser Thr
1               5                   10

( 2 ) INFORMATION FOR SEQ ID NO:36:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:36:

Asn Arg Ile Ser Tyr Gln Thr Ser Ser Thr
1               5                   10

( 2 ) INFORMATION FOR SEQ ID NO:37:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:37:

```
Asn Lys Ile Thr Tyr Gln Thr Ser Ser Thr
1               5                   1 0
```

( 2 ) INFORMATION FOR SEQ ID NO:38:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:38:

```
Asn Lys Leu Ser Tyr Gln Thr Ser Ser Thr
1               5                   1 0
```

( 2 ) INFORMATION FOR SEQ ID NO:39:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:39:

```
Gln Lys Leu Ser Tyr Gln Ser Ser Ser Thr
1               5                   1 0
```

( 2 ) INFORMATION FOR SEQ ID NO:40:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:40:

```
Asn Arg Leu Ser Tyr Gln Thr Ser Ser Thr
1               5                   1 0
```

( 2 ) INFORMATION FOR SEQ ID NO:41:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:41:

Asn Lys Val Ser Phe Gln Ser Ser Ser Thr
1               5                   10

( 2 ) INFORMATION FOR SEQ ID NO:42:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:42:

Asn Arg Val Ser Trp Gln Ser Ser Ser Thr
1               5                   10

( 2 ) INFORMATION FOR SEQ ID NO:43:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:43:

Gln Lys Val Ser Tyr Gln Ser Ser Ser Thr
1               5                   10

( 2 ) INFORMATION FOR SEQ ID NO:44:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:44:

Asn Lys Ile Ser Tyr Gln Ser Ser Ser Thr
1               5                   10

( 2 ) INFORMATION FOR SEQ ID NO:45:

( i ) SEQUENCE CHARACTERISTICS:
   ( A ) LENGTH: 19 amino acids
   ( B ) TYPE: amino acid
   ( C ) STRANDEDNESS: single
   ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:45:

Gly Glu Gln Gly Val Gln Lys Asp Val Ser Gln Ser Ser Ile Tyr Ser
1               5                   10                  15
Gln Thr Glu ( 2 ) INFORMATION FOR SEQ ID NO:46:

( i ) SEQUENCE CHARACTERISTICS:
      ( A ) LENGTH: 15 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:46:

Gly Lys Gly Ile Ser Ser Gln Tyr Ser Asn Thr Asp Glu Arg Leu
1               5                   10                  15

( 2 ) INFORMATION FOR SEQ ID NO:47:

( i ) SEQUENCE CHARACTERISTICS:
      ( A ) LENGTH: 19 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:47:

Gly Glu Asn Gly Leu Gln Lys Asp Val Ser Gln Ser Ser Ile Tyr Ser
1               5                   10                  15
Gln Thr Glu ( 2 ) INFORMATION FOR SEQ ID NO:48:

( i ) SEQUENCE CHARACTERISTICS:
      ( A ) LENGTH: 19 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO (i v) ANTI-SENSE: NO (v) FRAGMENT TYPE: internal (x i) SEQUENCE DESCRIPTION: SEQ ID NO:48:

Gly Glu Asn Gly Val Asn Lys Asp Val Ser Gln Ser Ser Ile Tyr Ser
1               5                   10                  15

Gln Thr Glu (2) INFORMATION FOR SEQ ID NO:49:

(i) SEQUENCE CHARACTERISTICS:
    (A) LENGTH: 19 amino acids
    (B) TYPE: amino acid
    (C) STRANDEDNESS: single
    (D) TOPOLOGY: linear (i i) MOLECULE TYPE: peptide (i i i) HYPOTHETICAL: NO (i v) ANTI-SENSE: NO (v) FRAGMENT TYPE: internal (x i) SEQUENCE DESCRIPTION: SEQ ID NO:49:

Gly Glu Asn Gly Val Gln Arg Asp Val Ser Gln Arg Ser Ile Tyr Ser
1               5                   10                  15

Gln Thr Glu (2) INFORMATION FOR SEQ ID NO:50:

(i) SEQUENCE CHARACTERISTICS:
    (A) LENGTH: 19 amino acids
    (B) TYPE: amino acid
    (C) STRANDEDNESS: single
    (D) TOPOLOGY: linear (i i) MOLECULE TYPE: peptide (i i i) HYPOTHETICAL: NO (i v) ANTI-SENSE: NO (v) FRAGMENT TYPE: internal (x i) SEQUENCE DESCRIPTION: SEQ ID NO:50:

Gly Glu Asn Gly Val Gln Lys Asp Val Ser Gln Lys Ser Ile Tyr Ser
1               5                   10                  15

Gln Thr Glu (2) INFORMATION FOR SEQ ID NO:51:

(i) SEQUENCE CHARACTERISTICS:
    (A) LENGTH: 19 amino acids
    (B) TYPE: amino acid
    (C) STRANDEDNESS: single
    (D) TOPOLOGY: linear (i i) MOLECULE TYPE: peptide (i i i) HYPOTHETICAL: NO (i v) ANTI-SENSE: NO (v) FRAGMENT TYPE: internal (x i) SEQUENCE DESCRIPTION: SEQ ID NO:51:

Gly Glu Asn Gly Val Gln Lys Asp Leu Ser Gln Thr Ser Ile Tyr Ser
1               5                   10                  15

Gln Thr Glu ( 2 ) INFORMATION FOR SEQ ID NO:52:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:52:

```
Gly Glu Asn Gly Val Gln Lys Asp Val Ser Gln Ser Ser Ile Phe Ser
1               5                   10                  15
Gln Thr Glu
```

( 2 ) INFORMATION FOR SEQ ID NO:53:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:53:

```
Gly Glu Asn Gly Val Gln Lys Asp Met Ser Gln Ser Ser Ile Tyr Thr
1               5                   10                  15
Gln Thr Glu
```

( 2 ) INFORMATION FOR SEQ ID NO:54:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:54:

```
Gly Glu Asn Gly Val Gln Lys Asp Val Ser Gln Arg Ser Ile Tyr Thr
1               5                   10                  15
Gln Thr Glu
```

( 2 ) INFORMATION FOR SEQ ID NO:55:

( i ) SEQUENCE CHARACTERISTICS:
        ( A ) LENGTH: 19 amino acids ( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:55:

Gly Glu Asn Gly Val Gln Lys Asp Val Ser Gln Ser Ser Ile Tyr Ser
1               5                   10                  15

Gln Ser Glu ( 2 ) INFORMATION FOR SEQ ID NO:56:

( i ) SEQUENCE CHARACTERISTICS:
( A ) LENGTH: 19 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:56:

Gly Glu Asn Gly Val Gln Lys Asp Val Ser Gln Arg Ser Ile Tyr Ser
1               5                   10                  15

Asn Thr Glu ( 2 ) INFORMATION FOR SEQ ID NO:57:

( i ) SEQUENCE CHARACTERISTICS:
( A ) LENGTH: 15 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:57:

Gly Lys Ala Ile Ser Ser Gln Tyr Ser Asn Thr Glu Glu Arg Leu
1               5                   10                  15

( 2 ) INFORMATION FOR SEQ ID NO:58:

( i ) SEQUENCE CHARACTERISTICS:
( A ) LENGTH: 15 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:58:

Gly Lys Gly Ile Ser Ser Gln Tyr Ser Asn Ser Glu Glu Arg Leu
1               5                   10                  15

( 2 ) INFORMATION FOR SEQ ID NO:59:

( i ) SEQUENCE CHARACTERISTICS:
      ( A ) LENGTH: 15 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:59:

Gly Arg Gly Ile Ser Ser Gln Tyr Ser Asn Thr Glu Glu Arg Leu
1               5                   10                  15

( 2 ) INFORMATION FOR SEQ ID NO:60:

( i ) SEQUENCE CHARACTERISTICS:
      ( A ) LENGTH: 15 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:60:

Gly Lys Gly Ile Thr Ser Gln Tyr Ser Asn Thr Glu Glu Arg Leu
1               5                   10                  15

( 2 ) INFORMATION FOR SEQ ID NO:61:

( i ) SEQUENCE CHARACTERISTICS:
      ( A ) LENGTH: 15 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:61:

Gly Lys Gly Ile Ser Thr Gln Tyr Ser Asn Thr Glu Glu Arg Leu
1               5                   10                  15

( 2 ) INFORMATION FOR SEQ ID NO:62:

( i ) SEQUENCE CHARACTERISTICS:
      ( A ) LENGTH: 15 amino acids
      ( B ) TYPE: amino acid
      ( C ) STRANDEDNESS: single (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:62:

```
Gly  Lys  Gly  Ile  Ser  Ser  Asn  Tyr  Ser  Asn  Thr  Glu  Glu  Arg  Leu
1                  5                  10                            15
```

(2) INFORMATION FOR SEQ ID NO:63:

(i) SEQUENCE CHARACTERISTICS:
(A) LENGTH: 15 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:63:

```
Ala  Lys  Gly  Ile  Ser  Ser  Gln  Tyr  Ser  Asn  Thr  Glu  Glu  Arg  Leu
1                  5                  10                            15
```

(2) INFORMATION FOR SEQ ID NO:64:

(i) SEQUENCE CHARACTERISTICS:
(A) LENGTH: 15 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:64:

```
Gly  Lys  Gly  Ile  Ser  Ser  Gln  Phe  Ser  Asn  Thr  Glu  Glu  Arg  Leu
1                  5                  10                            15
```

(2) INFORMATION FOR SEQ ID NO:65:

(i) SEQUENCE CHARACTERISTICS:
(A) LENGTH: 15 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:65:

```
Gly  Lys  Gly  Ile  Ser  Ser  Gln  Tyr  Thr  Asn  Ser  Glu  Glu  Arg  Leu
1                  5                  10                            15
```

(2) INFORMATION FOR SEQ ID NO:66:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:66:

```
Gly Lys Gly Ile Ser Ser Gln Tyr Ser Asn Ser Glu Glu Arg Leu
1               5                   10                  15
```

(2) INFORMATION FOR SEQ ID NO:67:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:67:

```
Ser Gln Lys Ala Asn Lys Ile Ser Tyr Gln Ser Ser Ser Thr Glu Glu
1               5                   10                  15
Arg Arg Leu His Tyr Gly Glu Asn Gly
                20                  25
```

(2) INFORMATION FOR SEQ ID NO:68:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:68:

```
Ile Ser Tyr Gln Ser Ser Ser Thr
1               5
```

(2) INFORMATION FOR SEQ ID NO:69:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (  i i i ) HYPOTHETICAL: NO (  i v ) ANTI-SENSE: NO ( v ) FRAGMENT TYPE: internal ( x i ) SEQUENCE DESCRIPTION: SEQ ID NO:69:

```
Ala  Asn  Lys  Ile  Ser  Tyr  Gln  Ser  Ser
1                  5
```

( 2 ) INFORMATION FOR SEQ ID NO:70:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide (  i i i ) HYPOTHETICAL: NO (  i v ) ANTI-SENSE: NO ( v ) FRAGMENT TYPE: internal ( x i ) SEQUENCE DESCRIPTION: SEQ ID NO:70:

```
Ala  Asn  Lys  Ile  Ser  Tyr  Gln  Ser  Ser  Ser  Thr  Leu
1                  5                           10
```

( 2 ) INFORMATION FOR SEQ ID NO:71:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide (  i i i ) HYPOTHETICAL: NO (  i v ) ANTI-SENSE: NO ( v ) FRAGMENT TYPE: internal ( x i ) SEQUENCE DESCRIPTION: SEQ ID NO:71:

```
Ala  Asn  Gly  Ile  Ser  Tyr  Gln  Ser  Ser  Ser  Thr  Glu
1                  5                           10
```

( 2 ) INFORMATION FOR SEQ ID NO:72:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide (  i i i ) HYPOTHETICAL: NO (  i v ) ANTI-SENSE: NO ( v ) FRAGMENT TYPE: internal ( x i ) SEQUENCE DESCRIPTION: SEQ ID NO:72:

```
Ala  Asn  Pro  Ile  Ser  Tyr  Gln  Ser  Ser  Ser  Thr  Glu
1                  5                           10
```

( 2 ) INFORMATION FOR SEQ ID NO:73:

( i ) SEQUENCE CHARACTERISTICS:
  ( A ) LENGTH: 12 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:73:

```
Ala  Asn  Lys  Ile  Ser  Tyr  Gln  Ser  Ala  Ser  Thr  Glu
1                   5                        10
```

( 2 ) INFORMATION FOR SEQ ID NO:74:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:74:

```
Ala  Asn  Lys  Ile  Ser  Tyr  Gln  Ser  Ser  Lys  Thr  Glu
1                   5                        10
```

( 2 ) INFORMATION FOR SEQ ID NO:75:

( i ) SEQUENCE CHARACTERISTICS:
    ( A ) LENGTH: 11 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:75:

```
Ala  Asn  Lys  Ile  Ser  Tyr  Gln  Ser  Ser  Thr  Glu
1                   5                        10
```

( 2 ) INFORMATION FOR SEQ ID NO:76:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
    ( A ) NAME/KEY: Peptide
    ( B ) LOCATION: 5
    ( D ) OTHER INFORMATION: /label= d- serine
        / note= "unnatural configuration of the amino acid"

( x i ) SEQUENCE DESCRIPTION: SEQ ID NO:76:

```
Ala  Asn  Lys  Ile  Ser  Tyr  Gln  Ser  Ser  Ser  Thr  Glu
1                  5                          10
```

( 2 ) INFORMATION FOR SEQ ID NO:77:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
    ( A ) NAME/KEY: Peptide
    ( B ) LOCATION: 4
    ( D ) OTHER INFORMATION: /label= d- isoleucine
        / note= "unnatural amino acid stereochemical configuration"

( x i ) SEQUENCE DESCRIPTION: SEQ ID NO:77:

```
Ala  Asn  Lys  Ile  Ser  Tyr  Gln  Ser  Ser  Ser  Thr  Glu
1                  5                          10
```

( 2 ) INFORMATION FOR SEQ ID NO:78:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:78:

```
Ala  Asn  Lys  Ile  Ser  Tyr  Gln  Ser  Ser  Gln  Thr  Glu
1                  5                          10
```

( 2 ) INFORMATION FOR SEQ ID NO:79:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:79:

Ala Asn Lys Ile Ser Tyr Gln Ser Ala Lys Thr Glu
1               5                   10

( 2 ) INFORMATION FOR SEQ ID NO:80:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
        ( A ) NAME/KEY: Peptide
        ( B ) LOCATION: 3
        ( D ) OTHER INFORMATION: /label= d- lysine
            / note= "unnatural amino acid stereochemical
            configuration"

( x i ) SEQUENCE DESCRIPTION: SEQ ID NO:80:

Ala Asn Lys Ile Ser Tyr Gln Ser Ser Ser Thr Glu
1               5                   10

( 2 ) INFORMATION FOR SEQ ID NO:81:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:81:

Ala Asn Lys Ile Ser Tyr Gln Ser Thr Glu
1               5                   10

( 2 ) INFORMATION FOR SEQ ID NO:82:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:82:

Ala Asn Lys Ser Tyr Gln Ser Ser Thr Glu
1               5                   10

( 2 ) INFORMATION FOR SEQ ID NO:83:

( i ) SEQUENCE CHARACTERISTICS:
  ( A ) LENGTH: 10 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:83:

```
Ala  Asn  Lys  Ile  Tyr  Gln  Ser  Ser  Thr  Glu
1                  5                       10
```

( 2 ) INFORMATION FOR SEQ ID NO:84:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:84:

```
Ala  Asn  Lys  Ala  Ser  Tyr  Gln  Ser  Ala  Ser  Thr  Glu
1                  5                           10
```

( 2 ) INFORMATION FOR SEQ ID NO:85:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:85:

```
Ala  Asn  Glu  Ile  Ser  Tyr  Gln  Ser  Ala  Ser  Thr  Glu
1                  5                           10
```

( 2 ) INFORMATION FOR SEQ ID NO:86:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:86:

Lys Ile Ser Tyr Gln Ser Ser
1               5

( 2 ) INFORMATION FOR SEQ ID NO:87:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:87:

Ser Tyr Gln Ser Ser Thr Glu
1               5

( 2 ) INFORMATION FOR SEQ ID NO:88:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:88:

Ser Tyr Gln Ser Ser Thr Leu
1               5

( 2 ) INFORMATION FOR SEQ ID NO:89:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:89:

Ala Ser Tyr Gln Ser Ser Thr Glu
1               5

( 2 ) INFORMATION FOR SEQ ID NO:90:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear (i i) MOLECULE TYPE: peptide (i i i) HYPOTHETICAL: NO (i v) ANTI-SENSE: NO (v) FRAGMENT TYPE: internal (x i) SEQUENCE DESCRIPTION: SEQ ID NO:90:

Glu Ile Ser Tyr Gln Ser Ser Ser Thr Glu
1               5                   10

(2) INFORMATION FOR SEQ ID NO:91:

(i) SEQUENCE CHARACTERISTICS:
        (A) LENGTH: 12 amino acids
        (B) TYPE: amino acid
        (C) STRANDEDNESS: single
        (D) TOPOLOGY: linear (i i) MOLECULE TYPE: peptide (i i i) HYPOTHETICAL: NO (i v) ANTI-SENSE: NO (v) FRAGMENT TYPE: internal (x i) SEQUENCE DESCRIPTION: SEQ ID NO:91:

Ala Asn Glu Ile Ser Tyr Gln Ser Ser Ser Thr Glu
1               5                   10

(2) INFORMATION FOR SEQ ID NO:92:

(i) SEQUENCE CHARACTERISTICS:
        (A) LENGTH: 12 amino acids
        (B) TYPE: amino acid
        (C) STRANDEDNESS: single
        (D) TOPOLOGY: linear (i i) MOLECULE TYPE: peptide (i i i) HYPOTHETICAL: NO (i v) ANTI-SENSE: NO (v) FRAGMENT TYPE: internal (x i) SEQUENCE DESCRIPTION: SEQ ID NO:92:

Ala Asn Lys Ile Ser Tyr Tyr Ser Ser Ser Thr Glu
1               5                   10

(2) INFORMATION FOR SEQ ID NO:93:

(i) SEQUENCE CHARACTERISTICS:
        (A) LENGTH: 12 amino acids
        (B) TYPE: amino acid
        (C) STRANDEDNESS: single
        (D) TOPOLOGY: linear (i i) MOLECULE TYPE: peptide (i i i) HYPOTHETICAL: NO (i v) ANTI-SENSE: NO (v) FRAGMENT TYPE: internal (x i) SEQUENCE DESCRIPTION: SEQ ID NO:93:

Ala Asn Lys Ile Ser Tyr Tyr Ser Ala Ser Thr Glu
1               5                   10

( 2 ) INFORMATION FOR SEQ ID NO:94:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:94:

Ala Ser Tyr Gln Ser Ser Leu
    1                5

( 2 ) INFORMATION FOR SEQ ID NO:95:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:95:

Ala Asn Ser Tyr Gln Ser Ser Ser Thr Glu
    1                5                   10

( 2 ) INFORMATION FOR SEQ ID NO:96:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:96:

Ala Ser Tyr Gln Ser Ser Ser Thr Glu
    1                5

( 2 ) INFORMATION FOR SEQ ID NO:97:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO (v) FRAGMENT TYPE: internal (xi) SEQUENCE DESCRIPTION: SEQ ID NO:97:

Ser Tyr Gln Ser Ser Ser Thr Glu
1               5

(2) INFORMATION FOR SEQ ID NO:98:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:98:

Ala Asn Lys Ala Ser Tyr Gln Ser Ala Ser Thr Cys
1               5                   10

(2) INFORMATION FOR SEQ ID NO:99:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:99:

Gln Ser Ser Thr Glu
1               5

(2) INFORMATION FOR SEQ ID NO:100:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:100:

Tyr Gln Ser Ser Thr Glu
1               5

(2) INFORMATION FOR SEQ ID NO:101:

(i) SEQUENCE CHARACTERISTICS:
        (A) LENGTH: 6 amino acids
        (B) TYPE: amino acid ( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:101:

Ser Gln Ser Ser Thr Glu
1               5

( 2 ) INFORMATION FOR SEQ ID NO:102:

( i ) SEQUENCE CHARACTERISTICS:
      ( A ) LENGTH: 10 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:102:

Ala Asn Lys Ile Ser Gln Ser Ser Thr Glu
1               5                   10

( 2 ) INFORMATION FOR SEQ ID NO:103:

( i ) SEQUENCE CHARACTERISTICS:
      ( A ) LENGTH: 11 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
      ( A ) NAME/KEY: Peptide
      ( B ) LOCATION: 3
      ( D ) OTHER INFORMATION: /label=unnatural
          / note= "ornithine"

( x i ) SEQUENCE DESCRIPTION: SEQ ID NO:103:

Ala Asn Xaa Ile Ser Tyr Gln Ser Ser Thr Glu
1               5                       10

( 2 ) INFORMATION FOR SEQ ID NO:104:

( i ) SEQUENCE CHARACTERISTICS:
      ( A ) LENGTH: 7 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
    ( A ) NAME/KEY: Peptide
    ( B ) LOCATION: 2
    ( D ) OTHER INFORMATION: /label=unnatural
        / note= "3,4-dichlorophenalanine"

( x i ) SEQUENCE DESCRIPTION: SEQ ID NO:104:

Ser Xaa Gln Ser Ser Thr Glu
1               5

( 2 ) INFORMATION FOR SEQ ID NO:105:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
        ( A ) NAME/KEY: Peptide
        ( B ) LOCATION: 2
        ( D ) OTHER INFORMATION: /label=unnatural
            / note= "(3-pyridinyl)alanine"

( x i ) SEQUENCE DESCRIPTION: SEQ ID NO:105:

Ser Xaa Gln Ser Ser Thr Glu
1               5

( 2 ) INFORMATION FOR SEQ ID NO:106:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:106:

Ser Lys Gln Ser Ser Thr Glu
1               5

( 2 ) INFORMATION FOR SEQ ID NO:107:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:107:

Ser Tyr Gln Ser Ser Ser Leu
1               5

( 2 ) INFORMATION FOR SEQ ID NO:108:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( i x ) FEATURE:
        ( A ) NAME/KEY: Peptide
        ( B ) LOCATION: 1
        ( D ) OTHER INFORMATION: /label=unnatural
            / note= "epsilon aminocaproic acid"

( x i ) SEQUENCE DESCRIPTION: SEQ ID NO:108:

Xaa Tyr Gln Ser Ser Ser Leu
1               5

( 2 ) INFORMATION FOR SEQ ID NO:109:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
        ( A ) NAME/KEY: Peptide
        ( B ) LOCATION: 4
        ( D ) OTHER INFORMATION: /label=unnatural
            / note= "N-methylisoleucine"

( x i ) SEQUENCE DESCRIPTION: SEQ ID NO:109:

Ala Asn Lys Xaa Ser Tyr Gln Ser Ser Thr Glu
1               5                   10

( 2 ) INFORMATION FOR SEQ ID NO:110:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:110:

```
        Ser  Tyr  Gln  Ser  Ser  Thr  Glu
        1                   5
```

( 2 ) INFORMATION FOR SEQ ID NO:111:

( i ) SEQUENCE CHARACTERISTICS:
  ( A ) LENGTH: 6 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:111:

```
        Tyr  Gln  Ser  Ser  Thr  Glu
        1               5
```

( 2 ) INFORMATION FOR SEQ ID NO:112:

( i ) SEQUENCE CHARACTERISTICS:
  ( A ) LENGTH: 7 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:112:

```
        Ser  Tyr  Lys  Ser  Ser  Thr  Glu
        1                   5
```

( 2 ) INFORMATION FOR SEQ ID NO:113:

( i ) SEQUENCE CHARACTERISTICS:
  ( A ) LENGTH: 7 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:113:

```
        Ser  Tyr  Tyr  Ser  Ser  Thr  Glu
        1                   5
```

( 2 ) INFORMATION FOR SEQ ID NO:114:

( i ) SEQUENCE CHARACTERISTICS:
  ( A ) LENGTH: 6 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:114:

Ser Tyr Gln Ser Ser Leu
1               5

( 2 ) INFORMATION FOR SEQ ID NO:115:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:115:

Ser Tyr Gln Ser Ser Leu
1               5

( 2 ) INFORMATION FOR SEQ ID NO:116:

( i ) SEQUENCE CHARACTERISTICS:
( A ) LENGTH: 7 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
( A ) NAME/KEY: Peptide
( B ) LOCATION: 1
( D ) OTHER INFORMATION: /label=unnatural
/ note= "2,3-diaminopropionic acid"

( x i ) SEQUENCE DESCRIPTION: SEQ ID NO:116:

Xaa Tyr Gln Ser Ser Ser Leu
1               5

( 2 ) INFORMATION FOR SEQ ID NO:117:

( i ) SEQUENCE CHARACTERISTICS:
( A ) LENGTH: 11 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:117:

```
Ala  Asn  Lys  Ile  Ser  Tyr  Gln  Ser  Ser  Ser  Thr
1                  5                        10
```

( 2 ) INFORMATION FOR SEQ ID NO:118:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:118:

```
Ala  Asn  Lys  Ala  Ser  Tyr  Gln  Ser  Ala  Ser  Thr  Leu
1                  5                        10
```

( 2 ) INFORMATION FOR SEQ ID NO:119:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:119:

```
Ala  Asn  Lys  Ala  Ser  Tyr  Gln  Ser  Ala  Ser  Leu
1                  5                        10
```

( 2 ) INFORMATION FOR SEQ ID NO:120:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:120:

```
Ala  Asn  Lys  Ala  Ser  Tyr  Gln  Ser  Ser  Ser  Leu
1                  5                        10
```

( 2 ) INFORMATION FOR SEQ ID NO:121:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide (  i  i  i  ) HYPOTHETICAL: NO (  i  v  ) ANTI-SENSE: NO (  v  ) FRAGMENT TYPE: internal (  x  i  ) SEQUENCE DESCRIPTION: SEQ ID NO:121:

```
Ala  Asn  Lys  Ala  Ser  Tyr  Gln  Ser  Ser  Leu
1                  5                            10
```

( 2 ) INFORMATION FOR SEQ ID NO:122:

(  i  ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear (  i  i  ) MOLECULE TYPE: peptide (  i  i  i  ) HYPOTHETICAL: NO (  i  v  ) ANTI-SENSE: NO (  v  ) FRAGMENT TYPE: internal (  i  x  ) FEATURE:
        ( A ) NAME/KEY: Peptide
        ( B ) LOCATION: 7
        ( D ) OTHER INFORMATION: /label= d- leucine
                / note= "unnatural amino acid stereochemical
                configuration"

(  x  i  ) SEQUENCE DESCRIPTION: SEQ ID NO:122:

```
Ser  Tyr  Gln  Ser  Ser  Thr  Leu
1                  5
```

( 2 ) INFORMATION FOR SEQ ID NO:123:

(  i  ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear (  i  i  ) MOLECULE TYPE: peptide (  i  i  i  ) HYPOTHETICAL: NO (  i  v  ) ANTI-SENSE: NO (  v  ) FRAGMENT TYPE: internal (  x  i  ) SEQUENCE DESCRIPTION: SEQ ID NO:123:

```
Ala  Asn  Lys  Ala  Ser  Tyr  Ala  Ser  Ser  Ser  Leu
1                  5                            10
```

( 2 ) INFORMATION FOR SEQ ID NO:124:

(  i  ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear (  i  i  ) MOLECULE TYPE: peptide (  i  i  i  ) HYPOTHETICAL: NO (  i  v  ) ANTI-SENSE: NO (  v  ) FRAGMENT TYPE: internal ( x i ) SEQUENCE DESCRIPTION: SEQ ID NO:124:

Lys Tyr Gln Ser Ser Ser Leu
1               5

( 2 ) INFORMATION FOR SEQ ID NO:125:

( i ) SEQUENCE CHARACTERISTICS:
      ( A ) LENGTH: 7 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:125:

Ser Tyr Gln Ser Ser Lys Leu
1               5

( 2 ) INFORMATION FOR SEQ ID NO:126:

( i ) SEQUENCE CHARACTERISTICS:
      ( A ) LENGTH: 7 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
      ( A ) NAME/KEY: Peptide
      ( B ) LOCATION: 7
      ( D ) OTHER INFORMATION: /label= d- leucine
              / note= "unnatural amino acid stereochemical
              configuration"

( x i ) SEQUENCE DESCRIPTION: SEQ ID NO:126:

Ser Tyr Gln Ser Ser Lys Leu
1               5

( 2 ) INFORMATION FOR SEQ ID NO:127:

( i ) SEQUENCE CHARACTERISTICS:
      ( A ) LENGTH: 7 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:127:

Asn Lys Ile Ser Tyr Tyr Ser
1               5

( 2 ) INFORMATION FOR SEQ ID NO:128:

( i ) SEQUENCE CHARACTERISTICS:
 ( A ) LENGTH: 7 amino acids
 ( B ) TYPE: amino acid
 ( C ) STRANDEDNESS: single
 ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:128:

Asn Lys Ala Ser Tyr Gln Ser
1               5

( 2 ) INFORMATION FOR SEQ ID NO:129:

( i ) SEQUENCE CHARACTERISTICS:
  ( A ) LENGTH: 5 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:129:

Ser Tyr Gln Ser Ser
1               5

( 2 ) INFORMATION FOR SEQ ID NO:130:

( i ) SEQUENCE CHARACTERISTICS:
  ( A ) LENGTH: 8 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:130:

Asn Lys Ile Ser Tyr Gln Ser Ala
1               5

( 2 ) INFORMATION FOR SEQ ID NO:131:

( i ) SEQUENCE CHARACTERISTICS:
  ( A ) LENGTH: 8 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:131:

Ala Asn Lys Ile Ser Tyr Tyr Ser
1               5

( 2 ) INFORMATION FOR SEQ ID NO:132:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:132:

Ala Asn Lys Ala Ser Tyr Gln Ser
1               5

( 2 ) INFORMATION FOR SEQ ID NO:133:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:133:

Ser Tyr Gln Ser Ser Thr
1               5

( 2 ) INFORMATION FOR SEQ ID NO:134:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:134:

Ser Tyr Gln Ser Ser Ser
1               5

( 2 ) INFORMATION FOR SEQ ID NO:135:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:135:

Ser Tyr Gln Ser Ser Leu
1               5

( 2 ) INFORMATION FOR SEQ ID NO:136:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:136:

Ala Asn Lys Ile Ser Tyr Gln Ser Ala
1               5

( 2 ) INFORMATION FOR SEQ ID NO:137:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:137:

Ala Asn Lys Ile Ser Tyr Tyr Ser Ser
1               5

( 2 ) INFORMATION FOR SEQ ID NO:138:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:138:

Ala Asn Lys Ile Ser Tyr Tyr Ser Ala
1               5

( 2 ) INFORMATION FOR SEQ ID NO:139:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:139:

Ala  Asn  Lys  Ala  Ser  Tyr  Gln  Ser  Ala
    1                   5

( 2 ) INFORMATION FOR SEQ ID NO:140:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:140:

Lys  Tyr  Gln  Ser  Ser
    1                   5

( 2 ) INFORMATION FOR SEQ ID NO:141:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
    ( A ) NAME/KEY: Peptide
    ( B ) LOCATION: 1
    ( D ) OTHER INFORMATION: /label=homoarginine ( x i ) SEQUENCE DESCRIPTION: SEQ ID NO:141:

Xaa  Tyr  Gln  Ser  Ser
    1                   5

( 2 ) INFORMATION FOR SEQ ID NO:142:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear (i i) MOLECULE TYPE: peptide (i i i) HYPOTHETICAL: NO (i v) ANTI-SENSE: NO (v) FRAGMENT TYPE: internal (x i) SEQUENCE DESCRIPTION: SEQ ID NO:142:

Lys Tyr Gln Ser Ser Ser
1               5

(2) INFORMATION FOR SEQ ID NO:143:

(i) SEQUENCE CHARACTERISTICS:
        (A) LENGTH: 6 amino acids
        (B) TYPE: amino acid
        (C) STRANDEDNESS: single
        (D) TOPOLOGY: linear (i i) MOLECULE TYPE: peptide (i i i) HYPOTHETICAL: NO (i v) ANTI-SENSE: NO (v) FRAGMENT TYPE: internal (i x) FEATURE:
        (A) NAME/KEY: Peptide
        (B) LOCATION: 1
        (D) OTHER INFORMATION: /label=homoarginine (x i) SEQUENCE DESCRIPTION: SEQ ID NO:143:

Xaa Tyr Gln Ser Ser Ser
1               5

(2) INFORMATION FOR SEQ ID NO:144:

(i) SEQUENCE CHARACTERISTICS:
        (A) LENGTH: 7 amino acids
        (B) TYPE: amino acid
        (C) STRANDEDNESS: single
        (D) TOPOLOGY: linear (i i) MOLECULE TYPE: peptide (i i i) HYPOTHETICAL: NO (i v) ANTI-SENSE: NO (v) FRAGMENT TYPE: internal (x i) SEQUENCE DESCRIPTION: SEQ ID NO:144:

Ser Tyr Gln Ser Ser Ser Leu
1               5

(2) INFORMATION FOR SEQ ID NO:145:

(i) SEQUENCE CHARACTERISTICS:
        (A) LENGTH: 7 amino acids
        (B) TYPE: amino acid
        (C) STRANDEDNESS: single
        (D) TOPOLOGY: linear (i i) MOLECULE TYPE: peptide (i i i) HYPOTHETICAL: NO (i v) ANTI-SENSE: NO (v) FRAGMENT TYPE: internal (i x) FEATURE:

(A) NAME/KEY: Peptide
                (B) LOCATION: 1
                (D) OTHER INFORMATION: /label=homoarginine (xi) SEQUENCE DESCRIPTION: SEQ ID NO:145:

Xaa  Tyr  Gln  Ser  Ser  Ser  Leu
    1                    5

(2) INFORMATION FOR SEQ ID NO:146:

(i) SEQUENCE CHARACTERISTICS:
                (A) LENGTH: 7 amino acids
                (B) TYPE: amino acid
                (C) STRANDEDNESS: single
                (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
                (A) NAME/KEY: Peptide
                (B) LOCATION: 7
                (D) OTHER INFORMATION: /label=norleucine (xi) SEQUENCE DESCRIPTION: SEQ ID NO:146:

Lys  Tyr  Gln  Ser  Ser  Ser  Leu
    1                    5

(2) INFORMATION FOR SEQ ID NO:147:

(i) SEQUENCE CHARACTERISTICS:
                (A) LENGTH: 5 amino acids
                (B) TYPE: amino acid
                (C) STRANDEDNESS: single
                (D) TOPOLOGY: linear (ii) MOLECULE TYPE: peptide (ix) FEATURE:
                (A) NAME/KEY: Peptide
                (B) LOCATION: 2
                (D) OTHER INFORMATION: /product="cyclohexylalanine"

(ix) FEATURE:
                (A) NAME/KEY: Peptide
                (B) LOCATION: 1
                (D) OTHER INFORMATION: /product="homoarginine"

(ix) FEATURE:
                (A) NAME/KEY: Peptide
                (B) LOCATION: 5
                (D) OTHER INFORMATION: /product="norleucine"

(xi) SEQUENCE DESCRIPTION: SEQ ID NO:147:

Xaa  Xaa  Gln  Ser  Leu
    1                    5

(2) INFORMATION FOR SEQ ID NO:148:

(i) SEQUENCE CHARACTERISTICS:
                (A) LENGTH: 6 amino acids
                (B) TYPE: amino acid
                (C) STRANDEDNESS: single
                (D) TOPOLOGY: linear (ii) MOLECULE TYPE: peptide (ix) FEATURE:
                (A) NAME/KEY: Peptide ( B ) LOCATION: 1
( D ) OTHER INFORMATION: /product="homoarginine"

( i x ) FEATURE:
( A ) NAME/KEY: Peptide
( B ) LOCATION: 2
( D ) OTHER INFORMATION: /product="homotyrosine"

( i x ) FEATURE:
( A ) NAME/KEY: Peptide
( B ) LOCATION: 6
( D ) OTHER INFORMATION: /product="norleucine"

( x i ) SEQUENCE DESCRIPTION: SEQ ID NO:148:

Xaa Xaa Gln Ser Ser Leu
1               5

( 2 ) INFORMATION FOR SEQ ID NO:149:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 1
( D ) OTHER INFORMATION: /product="homoarginine"

( i x ) FEATURE:
( A ) NAME/KEY: Peptide
( B ) LOCATION: 2
( D ) OTHER INFORMATION: /product="cyclohexylhomoalanine"

( i x ) FEATURE:
( A ) NAME/KEY: Peptide
( B ) LOCATION: 6
( D ) OTHER INFORMATION: /product="norleucine"

( x i ) SEQUENCE DESCRIPTION: SEQ ID NO:149:

Xaa Xaa Gln Ser Ser Leu
1               5

( 2 ) INFORMATION FOR SEQ ID NO:150:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 10
( D ) OTHER INFORMATION: /product="cyclohexylalanine"

( x i ) SEQUENCE DESCRIPTION: SEQ ID NO:150:

Ala Asn Lys Ala Ser Tyr Gln Ser Ser Xaa
1               5                   10

( 2 ) INFORMATION FOR SEQ ID NO:151:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( i x ) FEATURE:
    ( A ) NAME/KEY: Peptide
    ( B ) LOCATION: 1
    ( D ) OTHER INFORMATION: /product="homoarginine"

( x i ) SEQUENCE DESCRIPTION: SEQ ID NO:151:

```
Xaa  Tyr  Gln  Ser  Ser  Pro
1                    5
```

( 2 ) INFORMATION FOR SEQ ID NO:152:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1
        ( D ) OTHER INFORMATION: /product="homoarginine"

( x i ) SEQUENCE DESCRIPTION: SEQ ID NO:152:

```
Xaa  Tyr  Gln  Ser  Ser  His
1                    5
```

( 2 ) INFORMATION FOR SEQ ID NO:153:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1
        ( D ) OTHER INFORMATION: /product="homoarginine"

( x i ) SEQUENCE DESCRIPTION: SEQ ID NO:153:

```
Xaa  Tyr  Gln  Ser  Asn
1                    5
```

( 2 ) INFORMATION FOR SEQ ID NO:154:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1
        ( D ) OTHER INFORMATION: /product="homoarginine"

( i x ) FEATURE:
        ( A ) NAME/KEY: Peptide
        ( B ) LOCATION: 7
        ( D ) OTHER INFORMATION: /product="norleucine"

( x i ) SEQUENCE DESCRIPTION: SEQ ID NO:154:

```
Xaa  Tyr  Gln  Ser  Ser  Ser  Leu
1                    5
```

( 2 ) INFORMATION FOR SEQ ID NO:155:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1
        ( D ) OTHER INFORMATION: /product=
            " 4-aminomethylphenylalanine"

( i x ) FEATURE:
        ( A ) NAME/KEY: Peptide
        ( B ) LOCATION: 7
        ( D ) OTHER INFORMATION: /product="norleucine"

( x i ) SEQUENCE DESCRIPTION: SEQ ID NO:155:

Xaa   Tyr   Gln   Ser   Ser   Ser   Leu
    1                           5

( 2 ) INFORMATION FOR SEQ ID NO:156:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1
        ( D ) OTHER INFORMATION: /product="homoarginine"

( x i ) SEQUENCE DESCRIPTION: SEQ ID NO:156:

Xaa   Tyr   Gln   Ser   Ser   Ser   Leu
    1                           5

( 2 ) INFORMATION FOR SEQ ID NO:157:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 10
        ( D ) OTHER INFORMATION: /product="cyclohexylalanine"

( x i ) SEQUENCE DESCRIPTION: SEQ ID NO:157:

Ala   Asn   Lys   Ala   Lys   Tyr   Gln   Ser   Ser   Xaa
    1                       5                               10

( 2 ) INFORMATION FOR SEQ ID NO:158:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:

(A) NAME/KEY: Peptide
              (B) LOCATION: 1
              (D) OTHER INFORMATION: /product=
                    "2(4,6-dimethylpyrimidine)lysine"

(ix) FEATURE:
              (A) NAME/KEY: Peptide
              (B) LOCATION: 7
              (D) OTHER INFORMATION: /product="norleucine"

(xi) SEQUENCE DESCRIPTION: SEQ ID NO:158:

Xaa  Tyr  Gln  Ser  Ser  Ser  Leu
     1                   5

(2) INFORMATION FOR SEQ ID NO:159:

(i) SEQUENCE CHARACTERISTICS:
              (A) LENGTH: 6 amino acids
              (B) TYPE: amino acid
              (C) STRANDEDNESS: single
              (D) TOPOLOGY: linear (ii) MOLECULE TYPE: peptide (ix) FEATURE:
              (A) NAME/KEY: Peptide
              (B) LOCATION: 1
              (D) OTHER INFORMATION: /product="N'-(2-imidazolyl)lysine"

(xi) SEQUENCE DESCRIPTION: SEQ ID NO:159:

Xaa  Tyr  Gln  Ser  Ser  Leu
     1                   5

(2) INFORMATION FOR SEQ ID NO:160:

(i) SEQUENCE CHARACTERISTICS:
              (A) LENGTH: 10 amino acids
              (B) TYPE: amino acid
              (C) STRANDEDNESS: single
              (D) TOPOLOGY: linear (ii) MOLECULE TYPE: peptide (ix) FEATURE:
              (A) NAME/KEY: Peptide
              (B) LOCATION: 5
              (D) OTHER INFORMATION: /product="homoarginine"

(xi) SEQUENCE DESCRIPTION: SEQ ID NO:160:

Ala  Asn  Lys  Ala  Xaa  Tyr  Gln  Ser  Ser  Leu
     1                   5                        10

(2) INFORMATION FOR SEQ ID NO:161:

(i) SEQUENCE CHARACTERISTICS:
              (A) LENGTH: 7 amino acids
              (B) TYPE: amino acid
              (C) STRANDEDNESS: single
              (D) TOPOLOGY: linear (ii) MOLECULE TYPE: peptide (ix) FEATURE:
              (A) NAME/KEY: Peptide
              (B) LOCATION: 1
              (D) OTHER INFORMATION: /product=
                    "(4-aminocyclohexyl)alanine"

(ix) FEATURE:
              (A) NAME/KEY: Peptide
              (B) LOCATION: 7
              (D) OTHER INFORMATION: /product="norleucine"

(xi) SEQUENCE DESCRIPTION: SEQ ID NO:161:

Xaa Tyr Gln Ser Ser Ser Leu
1               5

(2) INFORMATION FOR SEQ ID NO:162:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1
        (D) OTHER INFORMATION: /product="N'-(2-imidazolyl)lysine"

(ix) FEATURE:
        (A) NAME/KEY: Peptide
        (B) LOCATION: 7
        (D) OTHER INFORMATION: /product="norleucine"

(xi) SEQUENCE DESCRIPTION: SEQ ID NO:162:

Xaa Tyr Gln Ser Ser Ser Leu
1               5

(2) INFORMATION FOR SEQ ID NO:163:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1
        (D) OTHER INFORMATION: /product="homoarginine"

(ix) FEATURE:
        (A) NAME/KEY: Peptide
        (B) LOCATION: 2
        (D) OTHER INFORMATION: /product="cyclohexylalanine"

(ix) FEATURE:
        (A) NAME/KEY: Peptide
        (B) LOCATION: 7
        (D) OTHER INFORMATION: /product="norleucine"

(xi) SEQUENCE DESCRIPTION: SEQ ID NO:163:

Xaa Xaa Gln Ser Ser Ser Leu
1               5

(2) INFORMATION FOR SEQ ID NO:164:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1
        (D) OTHER INFORMATION: /product="homoarginine"

(ix) FEATURE:
        (A) NAME/KEY: Peptide
        (B) LOCATION: 7

( D ) OTHER INFORMATION: /product="homoarginine"

( x i ) SEQUENCE DESCRIPTION: SEQ ID NO:164:

Xaa Tyr Gln Ser Ser Ser Xaa
1               5

( 2 ) INFORMATION FOR SEQ ID NO:165:

( i ) SEQUENCE CHARACTERISTICS:
      ( A ) LENGTH: 10 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: Peptide
      ( B ) LOCATION: 5
      ( D ) OTHER INFORMATION: /product="N'-(2-imidazolyl)lysine"

( i x ) FEATURE:
      ( A ) NAME/KEY: Peptide
      ( B ) LOCATION: 10
      ( D ) OTHER INFORMATION: /product="norleucine"

( x i ) SEQUENCE DESCRIPTION: SEQ ID NO:165:

Ala Asn Lys Ala Xaa Tyr Gln Ser Ser Leu
1               5                   10

( 2 ) INFORMATION FOR SEQ ID NO:166:

( i ) SEQUENCE CHARACTERISTICS:
      ( A ) LENGTH: 7 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: Peptide
      ( B ) LOCATION: 1
      ( D ) OTHER INFORMATION: /product="homoarginine"

( i x ) FEATURE:
      ( A ) NAME/KEY: Peptide
      ( B ) LOCATION: 2
      ( D ) OTHER INFORMATION: /product="3-iodotyrosine"

( i x ) FEATURE:
      ( A ) NAME/KEY: Peptide
      ( B ) LOCATION: 7
      ( D ) OTHER INFORMATION: /product="norleucine"

( x i ) SEQUENCE DESCRIPTION: SEQ ID NO:166:

Xaa Xaa Gln Ser Ser Ser Leu
1               5

( 2 ) INFORMATION FOR SEQ ID NO:167:

( i ) SEQUENCE CHARACTERISTICS:
      ( A ) LENGTH: 7 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: Peptide
      ( B ) LOCATION: 1
      ( D ) OTHER INFORMATION: /product="homoarginine"

( i x ) FEATURE:
    ( A ) NAME/KEY: Peptide
    ( B ) LOCATION: 2
    ( D ) OTHER INFORMATION: /product=
        " O-dimethylphosphotyrosine"

( i x ) FEATURE:
    ( A ) NAME/KEY: Peptide
    ( B ) LOCATION: 7
    ( D ) OTHER INFORMATION: /product="norleucine"

( x i ) SEQUENCE DESCRIPTION: SEQ ID NO:167:

Xaa  Xaa  Gln  Ser  Ser  Ser  Leu
1                   5

( 2 ) INFORMATION FOR SEQ ID NO:168:

( i ) SEQUENCE CHARACTERISTICS:
        ( A ) LENGTH: 6 amino acids
        ( B ) TYPE: amino acid
        ( C ) STRANDEDNESS: double
        ( D ) TOPOLOGY: linear ( i i ) MOLECULE TYPE: peptide ( i x ) FEATURE:
        ( A ) NAME/KEY: Peptide
        ( B ) LOCATION: 1
        ( D ) OTHER INFORMATION: /product="homoarginine"

( x i ) SEQUENCE DESCRIPTION: SEQ ID NO:168:

Xaa  Tyr  Gln  Ser  Ser  Asp
1                   5

( 2 ) INFORMATION FOR SEQ ID NO:169:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1
        ( D ) OTHER INFORMATION: /product="homoarginine"

( i x ) FEATURE:
        ( A ) NAME/KEY: Peptide
        ( B ) LOCATION: 2
        ( D ) OTHER INFORMATION: /product="O-methyltyrosine"

( i x ) FEATURE:
        ( A ) NAME/KEY: Peptide
        ( B ) LOCATION: 7
        ( D ) OTHER INFORMATION: /product="norleucine"

( x i ) SEQUENCE DESCRIPTION: SEQ ID NO:169:

Xaa  Xaa  Gln  Ser  Ser  Ser  Leu
1                   5

( 2 ) INFORMATION FOR SEQ ID NO:170:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i x ) FEATURE:

( A ) NAME/KEY: Peptide
                    ( B ) LOCATION: 10
                    ( D ) OTHER INFORMATION: /product="norleucine"

( x i ) SEQUENCE DESCRIPTION: SEQ ID NO:170:

Ala  Asn  Lys  Ala  Lys  Tyr  Gln  Ser  Ser  Leu
     1                   5                        10

( 2 ) INFORMATION FOR SEQ ID NO:171:

( i ) SEQUENCE CHARACTERISTICS:
                    ( A ) LENGTH: 7 amino acids
                    ( B ) TYPE: amino acid
                    ( C ) STRANDEDNESS: single
                    ( D ) TOPOLOGY: linear ( i i ) MOLECULE TYPE: peptide ( i x ) FEATURE:
                    ( A ) NAME/KEY: Peptide
                    ( B ) LOCATION: 1
                    ( D ) OTHER INFORMATION: /product="homoarginine"

( i x ) FEATURE:
                    ( A ) NAME/KEY: Peptide
                    ( B ) LOCATION: 2
                    ( D ) OTHER INFORMATION: /product="cyclohexylalanine"

( x i ) SEQUENCE DESCRIPTION: SEQ ID NO:171:

Xaa  Xaa  Gln  Ser  Ser  Ser  Leu
     1                   5

( 2 ) INFORMATION FOR SEQ ID NO:172:

( i ) SEQUENCE CHARACTERISTICS:
                    ( A ) LENGTH: 7 amino acids
                    ( B ) TYPE: amino acid
                    ( C ) STRANDEDNESS: single
                    ( D ) TOPOLOGY: linear ( i i ) MOLECULE TYPE: peptide ( i x ) FEATURE:
                    ( A ) NAME/KEY: Peptide
                    ( B ) LOCATION: 1
                    ( D ) OTHER INFORMATION: /product="N'-(2-imidazolyl)lysine"

( i x ) FEATURE:
                    ( A ) NAME/KEY: Peptide
                    ( B ) LOCATION: 2
                    ( D ) OTHER INFORMATION: /product="cyclohexylalanine"

( i x ) FEATURE:
                    ( A ) NAME/KEY: Peptide
                    ( B ) LOCATION: 7
                    ( D ) OTHER INFORMATION: /product="norleucine"

( x i ) SEQUENCE DESCRIPTION: SEQ ID NO:172:

Xaa  Xaa  Gln  Ser  Ser  Ser  Leu
     1                   5

( 2 ) INFORMATION FOR SEQ ID NO:173:

( i ) SEQUENCE CHARACTERISTICS:
                    ( A ) LENGTH: 6 amino acids
                    ( B ) TYPE: amino acid
                    ( C ) STRANDEDNESS: single
                    ( D ) TOPOLOGY: linear ( i i ) MOLECULE TYPE: peptide ( i x ) FEATURE:
                    ( A ) NAME/KEY: Peptide
                    ( B ) LOCATION: 1

(D) OTHER INFORMATION: /product="homoarginine"

(ix) FEATURE:
 (A) NAME/KEY: Peptide
 (B) LOCATION: 2
 (D) OTHER INFORMATION: /product="cyclohexylalanine"

(xi) SEQUENCE DESCRIPTION: SEQ ID NO:173:

```
Xaa  Xaa  Gln  Ser  Ser  Ser
1                   5
```

(2) INFORMATION FOR SEQ ID NO:174:

(i) SEQUENCE CHARACTERISTICS:
  (A) LENGTH: 6 amino acids
  (B) TYPE: amino acid
  (C) STRANDEDNESS: single
  (D) TOPOLOGY: linear (ii) MOLECULE TYPE: peptide (ix) FEATURE:
  (A) NAME/KEY: Peptide
  (B) LOCATION: 1
  (D) OTHER INFORMATION: /product="homoarginine"

(ix) FEATURE:
  (A) NAME/KEY: Peptide
  (B) LOCATION: 2
  (D) OTHER INFORMATION: /product="cyclohexylalanine"

(ix) FEATURE:
  (A) NAME/KEY: Peptide
  (B) LOCATION: 6
  (D) OTHER INFORMATION: /product="norleucine"

(xi) SEQUENCE DESCRIPTION: SEQ ID NO:174:

```
Xaa  Xaa  Gln  Ser  Ser  Leu
1                   5
```

(2) INFORMATION FOR SEQ ID NO:175:

(i) SEQUENCE CHARACTERISTICS:
  (A) LENGTH: 6 amino acids
  (B) TYPE: amino acid
  (C) STRANDEDNESS: single
  (D) TOPOLOGY: linear (ii) MOLECULE TYPE: peptide (ix) FEATURE:
  (A) NAME/KEY: Peptide
  (B) LOCATION: 1
  (D) OTHER INFORMATION: /product="homoarginine"

(ix) FEATURE:
  (A) NAME/KEY: Peptide
  (B) LOCATION: 2
  (D) OTHER INFORMATION: /product="cyclohexylalanine"

(ix) FEATURE:
  (A) NAME/KEY: Peptide
  (B) LOCATION: 6
  (D) OTHER INFORMATION: /product="norleucine"

(xi) SEQUENCE DESCRIPTION: SEQ ID NO:175:

```
Xaa  Xaa  Gln  Ser  Pro  Leu
1                   5
```

(2) INFORMATION FOR SEQ ID NO:176:

(i) SEQUENCE CHARACTERISTICS:
  (A) LENGTH: 7 amino acids
  (B) TYPE: amino acid (C) STRANDEDNESS: single
(D) TOPOLOGY: linear (i i) MOLECULE TYPE: peptide (i x) FEATURE:
(A) NAME/KEY: Peptide
(B) LOCATION: 1
(D) OTHER INFORMATION: /product="homoarginine"

(i x) FEATURE:
(A) NAME/KEY: Peptide
(B) LOCATION: 2
(D) OTHER INFORMATION: /product="3-fluorotyrosine"

(i x) FEATURE:
(A) NAME/KEY: Peptide
(B) LOCATION: 7
(D) OTHER INFORMATION: /product="norleucine"

(x i) SEQUENCE DESCRIPTION: SEQ ID NO:176:

Xaa  Xaa  Gln  Ser  Ser  Ser  Leu
1                      5

(2) INFORMATION FOR SEQ ID NO:177:

(i) SEQUENCE CHARACTERISTICS:
(A) LENGTH: 5 amino acids
(B) TYPE: amino acid
(C) STRANDEDNESS: single
(D) TOPOLOGY: linear (i i) MOLECULE TYPE: peptide (i x) FEATURE:
(A) NAME/KEY: Peptide
(B) LOCATION: 1
(D) OTHER INFORMATION: /product="homoarginine"

(x i) SEQUENCE DESCRIPTION: SEQ ID NO:177:

Xaa  Tyr  Gln  Ser  Pro
1                      5

(2) INFORMATION FOR SEQ ID NO:178:

(i) SEQUENCE CHARACTERISTICS:
(A) LENGTH: 6 amino acids
(B) TYPE: amino acid
(C) STRANDEDNESS: single
(D) TOPOLOGY: linear (i i) MOLECULE TYPE: peptide (i x) FEATURE:
(A) NAME/KEY: Peptide
(B) LOCATION: 6
(D) OTHER INFORMATION: /product="norleucine"

(x i) SEQUENCE DESCRIPTION: SEQ ID NO:178:

Lys  Tyr  Gln  Ser  Lys  Leu
1                      5

(2) INFORMATION FOR SEQ ID NO:179:

(i) SEQUENCE CHARACTERISTICS:
(A) LENGTH: 7 amino acids
(B) TYPE: amino acid
(C) STRANDEDNESS: single
(D) TOPOLOGY: linear (i i) MOLECULE TYPE: peptide (i x) FEATURE:
(A) NAME/KEY: Peptide (B) LOCATION: 1
(D) OTHER INFORMATION: /product="homoarginine"

(ix) FEATURE:
(A) NAME/KEY: Peptide
(B) LOCATION: 2
(D) OTHER INFORMATION: /product="4-aminophenylalanine"

(ix) FEATURE:
(A) NAME/KEY: Peptide
(B) LOCATION: 7
(D) OTHER INFORMATION: /product="norleucine"

(xi) SEQUENCE DESCRIPTION: SEQ ID NO:179:

Xaa  Xaa  Gln  Ser  Ser  Ser  Leu
1                     5

(2) INFORMATION FOR SEQ ID NO:180:

(i) SEQUENCE CHARACTERISTICS:
(A) LENGTH: 7 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide
(B) LOCATION: 1
(D) OTHER INFORMATION: /product="homoarginine"

(ix) FEATURE:
(A) NAME/KEY: Peptide
(B) LOCATION: 2
(D) OTHER INFORMATION: /product=
" 7-HO-tetrahydroisoquinoline CO2H"

(ix) FEATURE:
(A) NAME/KEY: Peptide
(B) LOCATION: 7
(D) OTHER INFORMATION: /product="norleucine"

(xi) SEQUENCE DESCRIPTION: SEQ ID NO:180:

Xaa  Xaa  Gln  Ser  Ser  Ser  Leu
1                     5

(2) INFORMATION FOR SEQ ID NO:181:

(i) SEQUENCE CHARACTERISTICS:
(A) LENGTH: 7 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide
(B) LOCATION: 1
(D) OTHER INFORMATION: /product="ornithine"

(ix) FEATURE:
(A) NAME/KEY: Peptide
(B) LOCATION: 7
(D) OTHER INFORMATION: /product="norleucine"

(xi) SEQUENCE DESCRIPTION: SEQ ID NO:181:

Xaa  Tyr  Gln  Ser  Ser  Ser  Leu
1                     5

(2) INFORMATION FOR SEQ ID NO:182:

(i) SEQUENCE CHARACTERISTICS:

(A) LENGTH: 7 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:182:

Lys Ala Ala Ser Ser Ser Leu
1               5

(2) INFORMATION FOR SEQ ID NO:183:

(i) SEQUENCE CHARACTERISTICS:
(A) LENGTH: 7 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide
(B) LOCATION: 7
(D) OTHER INFORMATION: /product="norleucine"

(xi) SEQUENCE DESCRIPTION: SEQ ID NO:183:

Lys Tyr Gln Ser Ser Ser Leu
1               5

(2) INFORMATION FOR SEQ ID NO:184:

(i) SEQUENCE CHARACTERISTICS:
(A) LENGTH: 11 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:184:

Leu Asn Lys Ala Ser Tyr Gln Ser Ser Ser Leu
1               5                   10

(2) INFORMATION FOR SEQ ID NO:185:

(i) SEQUENCE CHARACTERISTICS:
(A) LENGTH: 5 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide
(B) LOCATION: 1
(D) OTHER INFORMATION: /product="homoarginine"

(ix) FEATURE:
(A) NAME/KEY: Peptide
(B) LOCATION: 2
(D) OTHER INFORMATION: /product="cyclohexylalanine"

(xi) SEQUENCE DESCRIPTION: SEQ ID NO:185:

Xaa Xaa Gln Ser Ser
1               5

(2) INFORMATION FOR SEQ ID NO:186:

(i) SEQUENCE CHARACTERISTICS:
(A) LENGTH: 4 amino acids ( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:186:

Tyr Gln Ser Ser
1

( 2 ) INFORMATION FOR SEQ ID NO:187:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 1
( D ) OTHER INFORMATION: /product="homoarginine"

( x i ) SEQUENCE DESCRIPTION: SEQ ID NO:187:

Xaa Tyr Gln Ser
1

( 2 ) INFORMATION FOR SEQ ID NO:188:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 1
( D ) OTHER INFORMATION: /product="homoarginine"

( x i ) SEQUENCE DESCRIPTION: SEQ ID NO:188:

Xaa Tyr Gln Ser Ser Ser
1               5

( 2 ) INFORMATION FOR SEQ ID NO:189:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 5
( D ) OTHER INFORMATION: /product="norleucine"

( x i ) SEQUENCE DESCRIPTION: SEQ ID NO:189:

Gln Ser Ser Ser Leu
1               5

( 2 ) INFORMATION FOR SEQ ID NO:190:

( i ) SEQUENCE CHARACTERISTICS:
( A ) LENGTH: 6 amino acids
( B ) TYPE: amino acid (C) STRANDEDNESS: single
        (D) TOPOLOGY: linear (i i) MOLECULE TYPE: peptide (i x) FEATURE:
        (A) NAME/KEY: Peptide
        (B) LOCATION: 1
        (D) OTHER INFORMATION: /product=
            "7-HO-tetrahydro-3-isoquinoline CO2H"

(i x) FEATURE:
        (A) NAME/KEY: Peptide
        (B) LOCATION: 6
        (D) OTHER INFORMATION: /product="norleucine"

(x i) SEQUENCE DESCRIPTION: SEQ ID NO:190:

Xaa  Gln  Ser  Ser  Ser  Leu
    1                   5

(2) INFORMATION FOR SEQ ID NO:191:

(i) SEQUENCE CHARACTERISTICS:
        (A) LENGTH: 11 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:191:

Ala  Asn  Lys  Ala  Ser  Tyr  Ala  Ser  Ser  Ser  Leu
    1                   5                        10

(2) INFORMATION FOR SEQ ID NO:192:

(i) SEQUENCE CHARACTERISTICS:
        (A) LENGTH: 7 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:192:

Ser  Tyr  Gln  Ser  Ser  Lys  Leu
    1                   5

(2) INFORMATION FOR SEQ ID NO:193:

(i) SEQUENCE CHARACTERISTICS:
        (A) LENGTH: 9 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:193:

Ala  Asn  Lys  Ala  Ser  Tyr  Gln  Ser  Leu
    1                   5

(2) INFORMATION FOR SEQ ID NO:194:

(i) SEQUENCE CHARACTERISTICS:
        (A) LENGTH: 7 amino acids
        (B) TYPE: amino acid
        (C) STRANDEDNESS: single
        (D) TOPOLOGY: linear (i i) MOLECULE TYPE: peptide -continued (ix) FEATURE:
  (A) NAME/KEY: Peptide
  (B) LOCATION: 1
  (D) OTHER INFORMATION: /product="ornithine"

(xi) SEQUENCE DESCRIPTION: SEQ ID NO:194:

Xaa Tyr Gln Ser Ser Ser Leu
1                 5

| Peptide | Salt | SEQ.ID.NO. | % Peptide Cleaved at 4 Hours by York PSA |
|---|---|---|---|
| Semenogelin (463 aa) | | | 100 (30 min) |
| GRKANKISYQ-SSSTEERRLHYGENG | TFA | 6 | 100 (2 hrs) |
| SQKANKISYQ-SSSTEERRLHYGENG | TFA | 67 | 100 (3 hrs) |
| ANKISYQ-SSSTE | TFA | 11 | 98 |
| ISYQ-SSST | TFA | 68 | 0 |
| NKISYQ-SSST | TFA | 10 | 62 |
| NKISYQ-SSSTE | TFA | 3 | 90 |
| KISYQ-SSSTE | TFA | 9 | 49 |
| SYQ-SSSTE | TFA | 7 | 0 (3 hrs) |
| ISYQ-SSSTE | TFA | 8 | 0 |
| NKISYQ-SSS | TFA | 17 | 55 |
| ANKISYQ-SSS | TFA | 18 | 45 |
| ANKISYQ-SS | TFA | 69 | 39 |
| ANKISYQ-SSSTE-amide | TFA | 11 | 43 |
| Ac-ANKISYQ-SSSTL | TFA | 70 | 57 |
| Ac-ANKISYQ-SSSTE-amide | TFA | 11 | 40 |
| Ac-ANKISYQ-SSSTL-amide | TFA | 70 | 46 |
| Ac-ANGISYQ-SSSTE-amide | | 71 | 0 |
| Ac-ANPISYQ-SSSTE-amide | | 72 | 0 |
| Ac-ANKISYQ-SASTE-amide | TFA | 73 | 66 |
| Ac-ANKISYQ-SSKTE-amide | TFA | 74 | 80 |
| Ac-ANKISYQ-SSTL-amide | TFA | 75 | 44 |
| Ac-ANKI(dS)YQ-SSSTE-amide | TFA | 76 | 9 |
| Ac-ANK(dI)SYQ-SSSTE-amide | TFA | 77 | 0 |
| Ac-ANKISYQ-SSQTE-amide | TFA | 78 | 55 |
| Ac-ANKISYQ-SAKTE-amide | TFA | 79 | 80 |
| Ac-AN(dK)ISYQ-SSSTE-amide | TFA | 80 | 3 |
| Ac-ANKISYQ-STE-amide | TFA | 81 | 28 |
| Ac-ANKIYQ-SSTE-amide | TFA | 82 | 0 |
| Ac-ANKSYQ-SSTE-amide | TFA | 83 | 10 |
| Ac-ANKASYQ-SASTE-amide | TFA | 84 | 98 |
| Ac-ANEISYQ-SASTE-amide | | 85 | 10 |
| Ac-NKISYQ-SS-amide | TFA | 16 | 30 |
| Ac-KISYQ-SS-amide | TFA | 86 | 15 |
| Ac-SYQ-SSTE-amide | | 87 | 65 |
| Ac-SYQ-SSTL-acid | | 88 | 83 |
| Ac-ASYQ-SSTE-amide | | 89 | 68 |
| Ac-EISYQ-SSSTE-amide | | 90 | 0 |
| Ac-ANEISYQ-SSSTE-amide | | 91 | 0 |
| Ac-ANKISYY-SSSTE-amide | TFA | 92 | 73 |
| Ac-ANKISYY-SASTE-amide | TFA | 93 | 91 |

FIG.3

| Peptide | Salt | SEQ. ID. NO. | % Peptide Cleaved at 4 Hours by York PSA |
|---|---|---|---|
| Ac-ASYQ-SSL-acid | | 94 | 71 |
| Ac-ANSYQ-SSSTE-amide | | 95 | 28 |
| Ac-ASYQ-SSSTE-amide | | 96 | 64 |
| Ac-SYQ-SSSTE-amide | | 97 | 50 |
| Ac-ANKASYQ-SASTC-amide | TFA | 98 | 78 |
| Ac-Q-SSTE-amide | | 99 | 0 |
| Ac-YQ-SSTE-amide | | 100 | 0 |
| Ac-SQ-SSTE-amide | | 101 | 0 |
| Ac-ANKISQ-SSTE-amide | TFA | 102 | 0 |
| Ac-AN(ORN)ISYQ-SSTE-amide | TFA | 103 | 34 |
| Ac-S(3PAL)Q-SSTE-amide | | 104 | 4 |
| Ac-S(3,4-Cl2F)Q-SSTE-amide | | 105 | 6 |
| Ac-SKQ-SSTE-amide | TFA | 106 | 0 |
| Ac-SYQ-SSTL-acid | | 88 | 81 |
| Ac-SYQ-SSSL-acid | | 107 | 98 |
| (e-ACA)-YQ-SSSL-amide | AA | 108 | 0 |
| ANK(N-Me-I)SYQ-SSTL-amide | TFA | 109 | 0 |
| SYQ-SSTE-amide | | 110 | 0 |
| HO(CH2)2CO-YQ-SSTE-amide | | 111 | 0 |
| Ac-SYK-SSTE-amide | TFA | 112 | 5 |
| Ac-SYY-SSTE-amide | | 113 | 93 |
| Ac-SYQ-SSL-NHNH2 | | 114 | 32 |
| Ac-SYQ-SSL-acid | | 115 | 72 |
| DAP-YQ-SSSL-amide | AA | 116 | 0 |

FIG.3A

| Peptide | Salt | SEQ.ID.NO. | Time to Cleave 50% of Substrate by York PSA |
|---|---|---|---|
| Semenogelin (463 aa) | | | 100% at 30 min |
| Ac-hR(Cha)Q-SNNle-acid | TFA | 149 | 4 HR = 0% (PS) |
| Ac-hR(Cha)Q-SNle-acid | TFA | 147 | 200 (PS) |
| Ac-hRhYQ-SSNle-acid | TFA | 148 | 95 (PS) |
| Ac-ANKASYQ-SS-Cha-NHNH2 | TFA | 150 | >240 (4 HR = 31%) |
| Ac-hRYQ-SSP-acid | TFA | 151 | 30 |
| hRYQ-SSH-acid | TFA | 152 | >240 (4 HR = 0%) |
| Ac-hRYQ-SSH-acid | TFA | 153 | 60 |
| hRYQ-SP-acid | TFA | 177 | >240 (4 HR = 0%) |
| Ac-hRYQ-SQ-acid | TFA | 177 | >240 (4 HR = 0%) |
| Ac-hRYQ-SN-acid | TFA | 153 | 90 |
| Ac-hRYQ-S-acid | TFA | 187 | >240 (4 HR = 0%) |
| Ac-hRYQ-SSSNle-acid | | 154 | 40 |
| Ac-(Amf)YQ-SSSNle-acid | | 155 | 50 |
| NH2CO-hRYQ-SSSL-acid | TFA | 156 | 60 |
| Ac-ANKAKYQ-SS(Cha)-NHNH2 | TFA | 157 | 240 |
| Ac-(DPL)YQ-SSSNle-acid | TFA | 158 | 120 |
| Ac-(imidazolyl)KYQ-SSL-acid | TFA | 159 | 25 |
| Ac-ANKA(hR)YQ-SSL-acid | TFA | 160 | 105 |
| Ac-(p-NH2-Cha)YQ-SSSNle-acid | TFA | 161 | 140 |
| Ac-(imidazolyl)KYQSSSNle-acid | TFA | 162 | 25 |
| Ac-hR(Cha)Q-SSSNle-acid | TFA | 163 | 120 |
| Ac-hRYQ-SSShR-acid | TFA | 164 | 70 |
| Ac-hRYQ-SSS(MeL) | TFA | 188 | 90 |
| Ac-hRYQ-SSS(Ethylester-L) | | 156 | 85 |
| Ac-ANKA(imidazolyl)KYQ-SSNle-acid | TFA | 165 | 95 |
| Ac-hR(3 Iodo-Y)Q-SSSNle-acid | TFA | 166 | 55 |
| Ac-hR(Me2PO3-Y)Q-SSSNle-acid | TFA | 167 | 4 HR = 0% |
| Ac-hRYQ-SSD-acid | TFA | 168 | 25 |
| Ac-hR(O-Me-Y)Q-SSSNle-acid | TFA | 169 | 4 HR = 0% |
| Ac-ANKAKYQ-SSNle-acid | TFA | 170 | 80 |
| Ac-hR(Cha)Q-SSS(ethylester-L) | | 171 | 4 HR = 36% |
| Ac-(imidazolyl)K(Cha)Q-SSSNle-acid | TFA | 172 | 180 (PS) |
| Ac-hR(TIC)Q-SSSNle-acid | TFA | 179 | 4 HR = 0% |
| Ac-Q-SSSNle-acid | TFA | 189 | 4 HR = 0% |
| Ac-hR(Cha)Q-SSS-acid | TFA | 173 | 120 |
| Ac-hR(Cha)Q-SSNle-acid | TFA | 174 | 60 (PS) |
| Ac-hR(Cha)Q-SPNle-acid | TFA | 175 | 4 HR = 12% |
| Ac-hR(m-fluoro-Y)Q-SSSNle-acid | TFA | 176 | 100 |
| Ac-(7-HO-TIC)Q-SSSNle-acid | TFA | 190 | 4 HR = 0% |

FIG. 3B

| Doxorubicin-congener | Salt | SEQ.ID.NO. | % Peptide Cleaved at 4 Hours by York PSA |
|---|---|---|---|
| Ac-ANKISYQ-SSST-DOX (3') | TFA | 117 | 20 (1 HR) no sample left |
| Ac-ANKISYQ-SSSTL-DOX (3') | TFA | 70 | 87 |
| Ac-ANKASYQ-SASTL-DOX (3') | AA | 118 | NA |
| Ac-ANKASYQ-SASL-DOX (3') | AA | 119 | 100 (3 HR) |
| Ac-ANKASYQ-SSSL-DOX (3') | AA | 120 | 100 (3 HR) |
| Ac-ANKASYQ-SSL-DOX (3') | AA | 121 | 91 |
| Ac-SYQ-SST(dL)-DOX (3') |  | 122 | 17 |
| Ac-SYQ-SSSL-DOX (3') |  | 107 | 95 (PS) |
| Ac-ANKASYA-SSSL-DOX (3') | AA | 123 | 0 |
| Ac-KYQ-SSSL-DOX (3') | AA | 124 | 98 (PS) |
| Ac-SYQ-SSKL-DOX (3') | AA | 125 | 88 |
| Ac-SYQ-SSK(dL)-DOX (3') | AA | 126 | 87 |

FIG.5

| Doxorubicin-congener | Salt | SEQ. ID. NO. | TIME TO CLEAVE 50% OF SUBSTANCE BY YORK PSA |
|---|---|---|---|
| Ac-(ORN)YQ-SSSNle-DOX )(3') | AA | 181 | 4 HR = 20% |
| Ac-KAASSSL-DOX (3') | AA | 182 | 10X [ENZ] 20 HR = 11% |
| Ac-hRh(CHA)Q-SSNle-DOX (3') | AA | 149 | 4 HR = 30% |
| Ac-hRYQ-SSP-DOX (3') | | 151 | 45 |
| Ac-hRYQ-SP-DOX (3') | | 177 | >240 (4 HR = 0%) |
| Ac-hRYQ-SSSNle-DOX (3') | | 154 | 190 (PS) |
| Ac-AmfYQ-SSSNle-DOX (3') | | 155 | 110 (PS) |
| NH2CO-hRYQ-SSSL-DOX (3') | | 156 | 105 |
| Ac-KYQ-SSNle-DOX (3') | AA | 146 | >240 (4 HR = 36%) (PS) |
| Ac-KYQ-SKNLe-DOX (3') | AA | 178 | >240 (4 HR = 20%) (NO PROD) |
| Ac(cis-p-NH2Cha)YQSSSNleDOX (3') | | 161 | 240 (PS) |
| Ac-ANKA (hR)YQ-SSL-DOX (3') | | 160 | 60 |
| Ac-hRYQ-SN-DOX (3') | AA | 153 | 90 (PS) |
| Ac-hRYQ-SSH-DOX (3') | AA | 152 | 110 |
| Ac-(imidazolyl)KYQ-SSL-DOX (3') | | 159 | 150 |
| Ac-(imidazolyl)KYQSSSNle-DOX (3') | | 162 | 60 |
| Ac-hR(Cha)Q-SSSNle-DOX (3') | | 163 | 130 |
| Ac-hR(Me2PO3Y)Q-SSSNle-DOX (3') | | 167 | 4 HR = 0% |
| Ac-hRYQ-SSShR-DOX (3') | | 164 | 50 |
| Ac-hR(3-Iodo-Y)Q-SSSNle-DOX (3') | | 166 | 4 HR = 0% (PS) |
| Ac-hR(O-Me-Y)Q-SSSNle-DOX (3') | | 169 | 4 HR = 20% |
| Ac-hR(p-NH2-F)Q-SSSNle-DOX (3') | | 179 | 90 (PS) |
| Ac-hR(Cha)Q-SSNle-DOX (3') | | 174 | 120 |
| Ac-hR(Cha)Q-SPNle-DOX (3') | | 175 | 4 HR = 0% |
| Ac-(imidazolyl)K(Cha)QSSSNleDox (3') | | 172 | 180 |
| Ac-hR(TIC)Q-SSSNle-DOX (3') | | 180 | 4 HR = 14% |
| Ac-hR(3-Fluoro)YQSSSNleDOX (3') | | 176 | 4 HR = 26% |
| desAc-vinblastine-LNKASYQ-SSL-DOX | AA | 184 | 70 (PS) |
| Ac-ANKASYQ-SL-DOX (3') | TFA | 193 | 90 |
| Ac-(ORN)YQ-SSSNle-DOX (3') | TFA | 194 | 120 |

FIG.5A

| Doxorubicin-congener | Salt | SEQ.ID.NO. | % Peptide Cleaved/ LNCaP MEDIA 4 HR | % Peptide Cleaved/ DuPRO MEDIA 4 HR |
|---|---|---|---|---|
| Ac-ANKASYQ-SASL-DOX (3') | AA | 119 | 92 | 13 |
| Ac-ANKASYQ-SSSL-DOX (3') | AA | 121 | 98 | 13 |
| Ac-ANKASYQ-SSL-DOX (3') | | 122 | 95 | 27 |
| Ac-SYQ-SSSL-DOX (3') | | 107 | 63 | 0 |

FIG.6

| Cytotoxic Agent-congener | Salt | SEQ. ID. NO. | LNCaP Cell Kill, EC50 (μM) |
|---|---|---|---|
| Ac-ANKISYQ-SSST-DOX (3') | TFA | 117 | >100 |
| Ac-ANKISYQ-SSSTL-DOX (3') | TFA | 70 | 8.4 |
| Ac-ANKASYQ-SASTL-DOX (3') | AA | 118 | 31 |
| Ac-ANKASYQ-SASL-DOX (3') | AA | 119 | 16 (DuPRO > 100) |
| Ac-ANKASYQ-SSSL-DOX (3') | AA | 120 | 15 |
| Ac-ANKASYQ-SSL-DOX (3') | AA | 121 | 6.5 (DuPRO = 117) |
| Ac-SYQ-SSSL-DOX (3') | | 144 | 20 (DuPRO>100) (PS) |
| Ac-ANKASYA-SSSL-DOX (3') | AA | 191 | > 100 |
| Ac-KYQ-SSSL-DOX (3') | AA | 124 | 6.5 (DuPRO > 100) |
| Ac-SYQ-SSKL-DOX (3') | AA | 192 | 11.8 (DuPRO > 100) |
| Ac-SYQ-SSK(dL)-DOX (3') | AA | | >100 (DuPRO > 100) |
| Ac-hRYQ-SSSL-DOX (3') | AA | 145 | 6.4 (DuPRO > 100) |
| Ac-KYQ-SSSNle-DOX (3') | AA | 183 | 4.4 (DuPRO > 100) |
| Ac-(ORN)YQ-SSNle-DOX (3') | AA | 181 | 3.3 (DuPRO = 65) |
| Ac-hRh(CHA)Q-SSNle-DOX (3') | AA | 149 | |
| a-Me-A-DOX (3') | AA | | 7.0 (DuPRO = 20.8) |
| M-DOX (3') | AA | | 6.0 (DuPRO = 13.8) |
| | | | {4.9(DuPRO-33.3)} |
| G-DOX (3') | AA | | > 100 (DuPRO > 100) |
| N-methyl-G-DOX (3') | AA | | 39.0 (DuPRO = 58.8) |
| NH2(CH2)5-CO-DOX (3') | AA | | 59.2 (DuPRO > 100) |
| Ac-hRYQ-SSP-DOX (3') | | 151 | {33.3 (DuPRO = 100)} |
| Ac-hRYQ-SP-DOX (3') | | 177 | 25.2 (DuPRO = 44.5) |
| Ac-hRYQ-SSSNle-DOX (3') | | 154 | 4.4 (DuPRO = 41.0) (PS) |
| Ac-AmfYQ-SSSNle-DOX (3') | | 155 | 7.6 (DuPRO > 100) (PS) |
| NH2CO-hRYQ-SSSL-DOX (3') | | 156 | 35.7 (DuPRO > 100) |
| Ac-KYQ-SSNle-DOX (3') | AA | 146 | 4.6 (DuPRO = 76.9) (PS) |
| Ac-KYQ-SKNle-DOX (3') | AA | 178 | 5.7 (DuPRO >> 100){3.6} |
| Ac(cis-p-NH2Cha)YQSSNleDOX (3') | | 161 | 9.8 (DuPRO = 47.1) (PS) |
| Ac-ANKA(hR)YQ-SSL-DOX (3') | | 160 | 7.3 (DuPRO >> 100) |
| Ac-hRYQ-SN-DOX (3') | AA | 153 | 70.4 (DuPRO = 75.0) |
| Ac-hRYQ-SSH-DOX (3') | AA | 152 | 25.4 (DuPRO = 35.7) |
| Ac-(imidazolyl)KYQ-SSL-DOX (3') | AA | 159 | 6.3 (DuPRO = 12.8) (PS) |
| Ac-(imidazolyl)KYQSSSNle-DOX (3') | | 162 | 3.2 (DuPRO = 23) |
| | | | (PS at 50 mM) |
| Ac-hR(Cha)Q-SSSNle-DOX (3') | | 163 | 2.3 (DuPRO >> 100) |
| Ac-hR(Me2PO3Y)Q-SSSNle-DOX (3') | | 167 | 8.0 (DuPRO > 100) |
| Ac-hRYQ-SSShR-DOX (3') | | 164 | 32 (DuPRO > 100) |

FIG. 7

| Cytotoxic Agent-congener | Salt | SEQ. ID. NO. | LNCaP Cell Kill, EC50 (μM) |
|---|---|---|---|
| Ac-hR(3-Iodo-Y)Q-SSSNle-DOX (3') | | 166 | 12.8 (DuPRO = 60.8) |
| Ac-hR(O-Me-Y)Q-SSSNle-DOX (3') | | 169 | 7.4 (DuPRO = 13.5) |
| Ac-hR(p-NH2-F)Q-SSSNle-DOX (3') | | 179 | 7.5 (DuPRO > 100) |
| Ac-hR(Cha)Q-SSSNle-DOX (3') | | 174 | 3.4 (DuPRO > 100) |
| Ac-hR(Cha)Q-SPNle-DOx (3') | | 175 | 12.3 (DuPRO > 100) |
| Ac-ANKASYQ-SL-DOX (3') | TFA | 193 | 10 (DuPRO > 100) |
| Ac-(ORN)YQ-SSSNle-DOX (3') | TFA | 194 | 7.0 (DuPRO > 100) |
| Ac(imidazolyl)K(Cha)QSSSNleDOX(3') | | 172 | 4.0 (DuPRO > 100) (PS) |
| Ac-hR(TIC)Q-SSSNle-DOX (3') | | 180 | 3.2 (DuPRO = 50.9) |
| Ac-hR(3-Fluoro)YQSSSNleDOX(3') | | 176 | 3.2 (DuPRO = 58.8) |
| vinblastine | | | 0.5 (DuPRO = 85) |
| DAP-desAc-vinblastine | TFA | | 150 (DuPRO >> 100) |
| Ac-KYQ-SSSNle-DAP-desAc-vinblastine | TFA | 183 | 14.7 (DuPRO >> 100) {4.8} |
| Nle-DAP-desAc-vinblastine | TFA | | 5.9 (DuPRO > 100) |
| desAc-vinblastine-LNKASYQ-SSSL-amide | AA | 184 | 1.6 (DuPRO >>100) |

FIG. 7A

PEPTIDES

RELATED APPLICATION

The present patent application is a Continuation-in-Part application of application Ser. No. 08/468,161, filed Jun. 6, 1995, which itself is a Continuation-in-Part application of application Ser. No. 08/404,833, filed Mar. 15, 1995 now abandoned, which itself is a Continuation-in-Part application of application Ser. No. 08/267,092, filed Jun. 28, 1994 now U.S. Pat. No. 5,599,686.

BACKGROUND OF THE INVENTION

In 1994 cancer of the prostate gland is expected to be diagnosed in 200,000 men in the U.S. and 38,000 American males will die from this disease (Garnick, M. B. (1994). The Dilemmas of Prostate Cancer. Scientific American, April:72–81). Thus, prostate cancer is the most frequently diagnosed malignancy other than that of the skin) in U.S. men and the second leading cause of cancer-related deaths (behind lung cancer) in that group.

Prostate specific Antigen (PSA) is a single chain 33 kDa glycoprotein that is produced almost exclusively by the human prostate epithelium and occurs at levels of 0.5 to 2.0 mg/ml in human seminal fluid (Nadji, M., Taber, S. Z., Castro, A., et al. (1981) Cancer 48:1229;Papsidero, L., Kuriyama, M., Wang, M., et al. (1981). JNCI 25 66:37; Qui, S. D., Young, C. Y. F., Bihartz, D. L., et al. (1990), J. Urol. 144:1550; Wang, M. C., Valenzuela, L. A., Murphy, G. P., et al. (1979). Invest. Urol. 17:159). The single carbohydrate unit is attached at asparagine residue number 45 and accounts for 2 to 3 kDa of the total molecular mass. PSA is a protease with chymotrypsin-like specificity (Christensson, A., Laurell, C. B., Lilja, H. (1990). Eur. J. Biochem. 194:755–763). It has been shown that PSA is mainly responsible for dissolution of the gel structure formed at ejaculation by proteolysis of the major proteins in the sperm entrapping gel, Semenogelin I and Semenogelin II, and fibronectin (Lilja, F[. (1985). J. Clin. Invest. 76:1899; Lilja, H., Oldbring, J., Rannevik, G., et al. (1987). J. Clin. Invest. 80:28 1; McGee, R. S., Herr, J. C. (1988). Biol. Reprod. 39:499). The PSA mediated proteolysis of the gel-forming proteins generates several soluble Semenogelin I and Semenogelin II fragments and soluble fibronectin fragments with liquefaction of the ejaculate and release of progressively motile spermatoza (Lilja, H., Laurell, C. B. (1984). Scand. J. Clin. Lab. Invest. 44:447; McGee, R. S., Herr, J. C. (1987). Biol. Reprod. 37:431). Furthermore, PSA may proteolytically degrade IGFBP-3 (insulin-like growth factor binding protein 3) allowing IGF to stimulate specifically the growth of PSA secreting cells (Cohen et al., (1992) J. Clin. Endo. & Meta. 75:1046–1053).

PSA complexed to alpha 1-antichymotrypsin is the predominant molecular form of serum PSA and may account for up to 95% of the detected serum PSA (Christerisson, A., Björk, T., Nilsson, O., et al. (1993). J. Urol. 150:100–105; Lilja, H., Christensson, A., Dahlén, U. (1991). Clin. Chem. 37:1618–1625; Stenman, U. H., Leinoven, J., Alfthan, H., et al. (1991). Cancer Res. 51:222–226). The prostatic tissue (normal, benign hyperplastic, or malignant tissue) is implicated to predominantly release the mature, enzyn,atically active form of PSA, as this form is required for complex formation with alpha 1-antichymotrypsin (Mast, A. E., Enghild, J. J., Pizzo, S. V., et al. (1991). Biochemistry 30:1723–1730; Perlmutter, D. H., Glover, G. I., Rivetna, M., et al. (1990). Proc. Natl. Acad. Sci. USA 87:3753–3757). Therefore, in the microenvironment of prostatic PSA secreting cells the PSA is believed to be processed and secreted in its mature enzymatically active form not complexed to any inhibitory molecule. PSA also forms stable complexes with alpha 2-macroglobulin, but as this results in encapsulation of PSA and complete loss of the PSA epitopes, the in vivo significance of this complex formation is unclear. A free, noncomplexed form of PSA constitutes a minor fraction of the serum PSA (Christensson, A., Bjork, T., Nilsson, O., et al. (1993). J. Urol. 150:100–105; Lilja, H., Christensson, A., Dahlen, U. (1991). Clin. Chem. 37:1618–1625). The size of this form of serum PSA is similar to that of PSA in seminal fluid (Lilja, H., Christensson, A., Dahlén, U. (1991). Clin. Chem. 37:1618–1625) but it is yet unknown as to whether the free form of serum PSA may be a zymogen; an internally cleaved, inactive form of mature PSA; or PSA manifesting enzyme activity. However, it seems unlikely that the free form of serurm PSA manifests enzyme activity, since there is considerable (100 to 1000 fold) molar excess of both unreacted alpha 1-antichymotrypsin and alpha 2-macroglobulin in serum as compared with the detected serum levels of the free 33 kDa form of PSA (Christensson, A., Björk, T., Nilsson, O., et al. (1993). J. Urol. 150:100–105; Lilja, H., Christensson, A., Dahlen, U. (1991). Clin. Chem. 37:1618–1625).

Serum measurements of PSA are useful for monitoring the treatment of adenocarcinoma of the prostate (Duffy, M. S. (1989). Ann. Clin. Biochem. 26:379–387; Brawer, M. K. and Lange, P. H. (1989). Urol. Suppl. 5:11–16; Hara, M. and Kimura, H. (1989). J. Lab. Clin. Med. 113:541–548), although above normal serum concentrations of PSA have also been reported in benign prostatic hyperplasia and subsequent to surgical trauma of the prostate (Lilja, H., Christensson, A., Dahlén, U. (1991). Clin. Chem. 37:1618–1625). Prostate metastases are also known to secrete immunologically reactive PSA since serum PSA is detectable at high levels in prostatectomized patients showing widespread metatstatic prostate cancer (Ford, T. F., Butcher, D. N., Masters, R. W., et al. (1985). Brit. J. Urology 57:50–55). Therefore, a cytotoxic compound that could be activated by the proteolytic activity of PSA should be prostate cell specific as well as specific for PSA secreting prostate metastases.

Accordingly, it is the object of this invention to provide novel oligopeptides which selectively are enzymatically cleaved by active free prostate specific antigen (PSA).

It is also the object of this invention to provide a quantitative assay for enzymatically active PSA which incorporates those novel oligopeptides.

It is further the object of this invention to provide a novel anti-cancer composition useful for the treatment of prostate cancer which comprises those novel oligopeptides in conjugation with a cytotoxic agent.

Another object of this invention is to provide a method of treating prostate cancer which comprises administration of novel anti-cancer composition.

SUMMARY OF THE INVENTION

The several points of cleavage where semenogelin I is selectively proteolytically cleaved by free PSA have been identified. Oligopeptides which comprise the amino acid sequences that are recognized and proteolytically cleaved by free prostate specific antigen (PSA) are described. Such oligopeptides are useful in assays which can determine the free PSA protease activity in vitro and in vivo. Furthermore, such oligopeptides may be incorporated into therapeutic agents which comprise conjugates of such oligopeptides and known cytotoxic agents and which are useful in the treatment of prostatic cancer.

BRIEF DESCRIPTION OF THE FIGURES

FIGS. 1 and 1A: Primary Amino Acid Sequence of Semenogelin I: The primary amino acid sequence of Semenogelin I is shown. (SEQ.ID.NO.: 1) The PSA proteolytic cleavage sites ("CS") are shown (numbered in order of the relative affinity of a site towards PSA hydrolysis) and the protein fragments are numbered sequentially starting at the amino terminus.

FIG. 2: Cleavage Affinity of Synthetic Oligopeptides: A nested set of synthetic oligopeptides was prepared and the oligopeptides were digested with enzymatically active free PSA for various times. The results are shown. All of the oligopeptides were tested as trifluoroacetate salts. The following SEQ. ID. NOs. apply to the peptides listed in the Figure: peptide 1—SEQ. ID. NO. 7; peptide 2—SEQ. ID. NO. 8; peptide 3—SEQ. ID. NO. 9; peptide 4—SEQ. ID. NO. 3; peptide 5—SEQ. ID. NO. 10; peptide 6—SEQ. ID. NO. 11; peptide 7—SEQ. ID. NO. 18; peptide 8—SEQ. ID. NO. 17; peptide 9—SEQ. ID. NO. 69; and peptide 10—SEQ. ID. NO. 6.

FIGS. 3, 3A and 3B: Cleavage Affinity of Synthetic Oligopeptides: Synthetic oligopeptides were prepared and the oligopeptides were digested with enzymatically active free PSA for four (4) hours. The percentage of the oligopeptide that is cleaved in this period of time is listed. The results are shown in FIGS. 3 and 3A. FIG. 3B shows the amount of time (in minutes) required for 50% cleavage of the noted oligopeptides with enzymatically active free PSA. If no salt is indicated for an oligopeptide, the free base was tested.

FIGS. 5 and 5A: Cleavage Affinity of Oligopeptides in Conjugation with Doxorubicin by Free PSA In Vitro: Oligopeptides-doxorubicin conjugates were prepared and the conjugates were digested with enzymatically active free PSA for four (4) hours. The percentage conjugate that is enzymatically cleaved in the oligopeptide in this period of time is listed. The results are shown in FIG. 5. FIG. 5A shows the amount of time (in minutes) required for 50% cleavage of the noted oligopeptide-cytotoxic agent conjugates with enzymatically active free PSA. If no salt is indicated for the conjugate, the free conjugate was tested.

FIG. 6: Cleavage Affinity of Oligopeptides in Conjugation with Doxorubicin in Cell Conditioned Media: Oligopeptides-doxorubicin conjugates were reacted for four (4) hours with cell culture media that had been conditioned by exposure to LNCaP cells (which are known to secrete free PSA) or DuPRO cell (which do not secrete free PSA). The percentage conjugate that is enzymatically cleaved in the oligopeptide in this period of time is listed. The results are shown in FIG. 6.

FIG. 7: Cytotoxicity Data of Cleavable Oligopeptide-Doxorubicin Conjugates: The data in FIG. 7 shows cytotoxicity (as $EC_{50}$) of conjugates of doxorubicin covalently bound to an oligopeptide that contain a free PSA proteolytic cleavage site against a cancer cell line that is known to secrete free PSA. Also shown for selected conjugates is the cytotoxicity of the conjugate against a cell line (DuPRO) which does not secrete free PSA. If no salt is indicated for the conjugate, the free conjugate was tested.

DETAILED DESCRIPTION OF THE INVENTION

Figure 4:
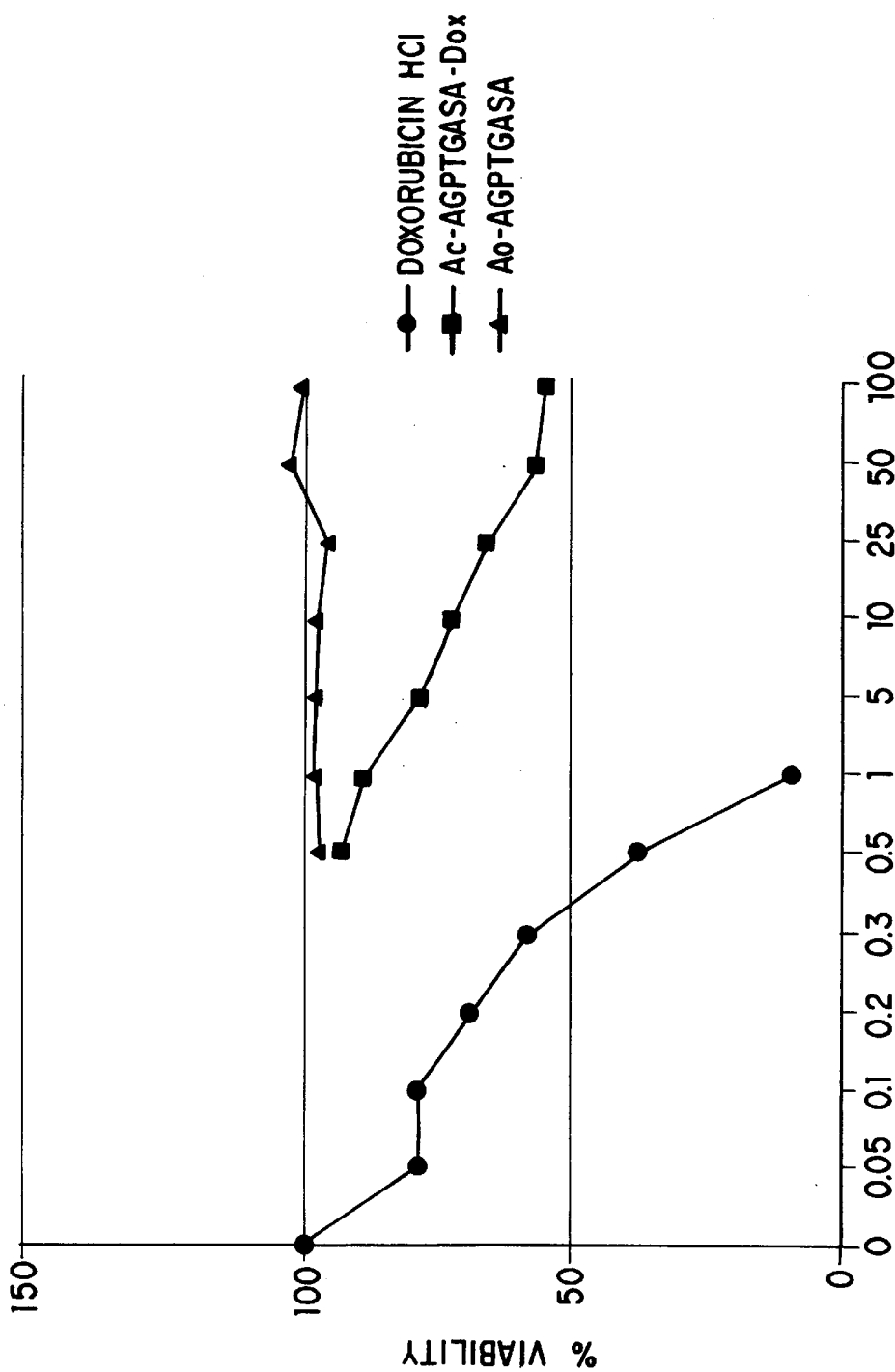
FIG. 4: Cytotoxicity Data of Non-cleavable Oligopeptide-Doxorubicin Conjugates: The data of the figure shows comparative cytotoxicity of doxorubicin and a conjugate of doxorubicin covalently bound to an oligopeptide (Compound 12d) that does not contain the free PSA proteolytic cleavage site. The $EC_{50}$ for doxorubicin is 0.3 $\mu$M, while the acetylated oligopeptide modified doxorubicin has an $EC_{50}$ that has been reduced by greater than 300 fold. This conjugate had no HPLC detectable contamination with unmodified doxorubicin. The oligopeptide alone had no detectable cell killing activity.

The present invention relates to novel oligopeptides which are specifically recognized by the free prostate specific antigen (PSA) and are capable of being proteolytically cleaved by the enzymatic activity of the free prostate specific antigen or pharmaceutically acceptable salts thereof. Such oligopeptides include oligomers that comprise an amino acid sequence selected from:

a) AsnLysIleSerTyrGln|Ser (SEQ.ID.NO.: 13), b) LysIleSerTyrGln|Ser (SEQ.ID.NO.: 14), c) GlyGluAsnGlyValGlnLysAspValSerGlnXaaSerIle Tyr|SerGlnThrGlu (SEQ.ID.NO.: 15), d) GlyLysGlyIleSerSerGlnTyr|SerAsnTirGluGluArgLeu (SEQ.ID.NO.: 2), e) AsnLysIleSerTyrTyr|Ser (SEQ.ID.NO.: 127), f) AsnLysAlaSerTyrGln|Ser (SEQ.ID.NO.: 128), g) SerTyrGln|SerSer (SEQ.ID.NO.: 129);

h) LysTyrGln|SerSer (SEQ.ID.NO.: 140);

i) hArgTyrGln|SerSer (SEQ.ID.NO.: 141);

j) hArgChaGln|SerSer (SEQ.ID.NO.: 185); and k) TyrGln|SerSer (SEQ.ID.NO.: 186);

wherein hArg is homoarginine, Cha is cyclohexylalanine and Xaa is any natural amino acid.

In an embodiment of the instant invention, the oligopeptides include oligomers that comprise an amino acid sequence that is selected from:

a) AsnLysIleSerTyrGln|SerSer (SEQ.ID.NO.: 16), b) AsnLysIleSerTyrGln|SerAla (SEQ.ID.NO.: 130), c) AsnLysIleSerTyrGln|SerSerSer (SEQ.ID.NO.: 17), d) AlaAsnLysIleSerTyrGln|SerSerSer (SEQ.ID.NO.: 18), e) LysIleSerTyrGln|SerSerSerThrGlu (SEQ.ID.NO.: 19), f) GlyGluAsnGlyValGlnLysAspValSerGlnArgSerIle Tyr|SerGlnThrGlu (SEQ.ID.NO.: 4), g) GlyGluAsnGlyValGlnLysAspValSerGlnSerSerIle Tyr|SerGlnThrGlu (SEQ.ID.NO.: 5), h) AlaAsnLysIleSerTyrTyr|Ser (SEQ.ID.NO.: 131), i) AlaAsnLysAlaSerTyrGln|Ser (SEQ.ID.NO.: 132), j) SerTyrGln|SerSerThr (SEQ.ID.NO.: 133), k) SerTyrGin|SerSerSer (SEQ.ID.NO.: 134), l) LysTyrGln|SerSerSer (SEQ.ID.NO.: 142), m) hArgTyrGln|SerSerSer (SEQ.ID.NO.: 143), and n) SerTyrGln|SerSerLeu (SEQ.ID.NO.: 135);

or the pharmaceutically acceptable salts thereof.

In a more preferred embodiment of the instant invention, the oligopeptides include oligomers that comprise an amino acid sequence that is selected from:

a) AsnLysIleSerTyrGln|SerSerSerThr (SEQ.ID.NO.: 10), b) AlaAsnLysIleSerTyrGln|SerAla (SEQ.ID.NO.: 136), c) AsnLysIleSerTyrGln|SerSerSerThrGlu (SEQ.ID.NO.:3), d) AlaAsnLysIleSerTyrGln|SerSerSerThrGlu (SEQ.ID.NO.: 11), e) GlyGluAsnGlyValGlnLysAspValSerGlnArgSerIle Tyr|SerGlnThrGlu (SEQ.ID.NO.: 4), f) AlaAsnLysIleSerTyrTyr|SerSer (SEQ.ID.NO.: 137), g) AlaAsnLysIleSerTyrTyr|SerAla (SEQ.ID.NO.: 139), h) AlaAsnLysAlaSerTyrGln|SerAla (SEQ.ID.NO.: 139), i) AlaSerTyrGln|SerSerLeu (SEQ.ID.NO.: 94);
or the pharmaceutically acceptable salts thereof.

In a further embodiment of the instant invention, the oligopeptides include oligomers that comprise an amino acid sequence that is selected from:

a) GlyArgLysAlaAsnLysIleSerTyrGln|SerSerSerThr Glu-GluArgArg LeuHisTyr GlyGluAsnGly (SEQ.ID.NO.: 6).

The phrase "oligomers that comprise an amino acid sequence" as used hereinabove, and elsewhere in the Detailed Description of the Invention, describes oligomers of from about 6 to about 100 amino acids residues which include in their amino acid sequence the specific amino acid sequence decribed and which are therefore proteolytically cleaved within the amino acid sequence described by free PSA. Thus, for example, the following oligomer:

GlnLeuAspAsnLysIleSerTyrGln|SerSerSerThrHis GlnSerSer (SEQ.ID.NO.: 20)

comprises the amino acid sequence:

AsnLysIleSerTyrGln|SerSerSerThr (SEQ.ID.NO.: 10) and would therefore come within the instant invention. It is understood that such oligomers do not include semenogelin I and semenogelin II.

It is also understood that the instant invention includes oligomers wherein the N-terminus amino acid or the C-terminus amino acid, or both terminus amino acids are modified. Such modifications include, but are not limited to, acylation of the amine group at the N-terminus and formation of an amide to replace the carboxylic acid at the C-terminus. Addition of such moieties may be performed during solid-phase synthesis of the oligomer; thus, attachment of the C-terminus amino acid to a solid phase resin may be through an amine which results in an amide moiety upon acidic cleavage of the oligomer from the resin. Thus the following compounds are considered "oligomers that comprise an amino acid sequence" as used hereinabove and are meant to be illustrative and are not limiting:

AlaAsnLysIleSerTyrGln|SerSerSerThrGlu-amide (SEQ.ID.NO.: 11)
Ac-AlaAsnLysIleSerTyrGln|SerSerSerThrLeu (SEQ.ID.NO.: 70)
Ac-AlaAsnLysIleSerTyrGln|SerSerSerThrGlu-amide (SEQ.ID.NO.: 11)
Ac-AlaAsnLysIleSerTyrGln|SerSerSerThrLeu-amide (SEQ.ID.NO.: 70)
Ac-AlaAsnLysIleSerTyrGln|SerAlaSerThrGlu-amide (SEQ.ID.NO.: 73)
Ac-AlaAsnLysIleSerTyrGln|SerSerLysThrGlu-amide (SEQ.ID.NO.: 74)
Ac-AlaAsnLysIleSerTyrGln|SerSerThrGlu-amide (SEQ.ID.NO.: 75)
Ac-AlaAsnLysIleSerTyrGln|SerSerGlnThrGlu-amide (SEQ.ID.NO.: 78)
Ac-AlaAsnLysIleSerTyrGln|SerAlaLysThrGlu-amide (SEQ.ID.NO.: 79)
Ac-AlaAsnLysIleSerTyrGln|SerThrGlu-amide (SEQ.ID.NO.: 81)
Ac-AlaAsnLysSerTyrGln|SerSerThrGlu-amide (SEQ.ID.NO.: 82)
Ac-AlaAsnLysAlaSerTyrGlnISerAlaSerThrGlu-amide (SEQ.ID.NO.: 84)
Ac-AlaAsnGluIleSerTyrGln|SerAlaSerThrGlu-amide (SEQ.ID.NO.: 85)
Ac-AsnLysIleSerTyrGln|SerSer-amide (SEQ.ID.NO.: 16)
Ac-LysIleSerTyrGln|SerSer-amide (SEQ.ID.NO.: 86)
Ac-SerTyrGln|SerSerThrGlu-amide (SEQ.ID.NO.: 87)
Ac-AlaSerTyrGln|SerSerThrGlu-amide (SEQ.ID.NO.: 89)
Ac-AlaAsnLysIleSerTyrTyr|SerSerSerThrGlu-amide (SEQ.ID.NO.: 92)
Ac-AlaAsnLysIleSerTyrTyr|SerAlaSerThrGlu-amide (SEQ.ID.NO.: 93)
Ac-AlaSerTyrGln|SerSerLeu-amide (SEQ.ID.NO.: 94)
Ac-AlaAsnSerTyrGln|SerSerSerThrGlu-amide (SEQ.ID.NO.: 95)
Ac-AlaSerTyrGln|SerSerSerThrGlu-amicle (SEQ.ID.NO.: 96)
Ac-SerTyrGln|SerSerSerThrGlu-amide (SEQ.ID.NO.: 97)
Ac-AlaAsnLysAlaSerTyrGln|SerAlaSerCys-amide (SEQ.ID.NO.: 98)
Ac-hArg(Cha)Gln|SerNle-Acid (SEQ.ID.NO.: 147)
Ac-hArghTyrGln|SerSerNle-Acid (SEQ.ID.NO.: 148)
Ac-hArgh(Cha)Gln|SerSerNle-Acid (SEQ.ID.NO.: 149)
Ac-AlaAspLysAlaSerTyrGln|SerSer-Cha-NHNH$_2$ (SEQ.ID.NO.: 150)
Ac-hArgTyrGln|SerSerPro-Acid (SEQ.ID.NO.: 151)
Ac-hArgTyrGln|SerSerHis-Acid (SEQ.ID.NO.: 152)
Ac-hArgTyrGln|SerAsn-Acid (SEQ.ID.NO.: 153)
Ac-hArgTyrGln|SerSerSerNle-Acid (SEQ.ID.NO.: 154)
Ac-(Amf)TyrGln|SerSerSerNle-Acid (SEQ.ID.NO.: 155)
H$_2$NCO-hArgTyrGln|SerSerSerLeu-Acid (SEQ.ID.NO.: 156)
Ac-AlaAspLysAlaLysTyrGln|SerSer(Cha)-NHNH$_2$ (SEQ.ID.NO.: 157)
Ac-(DPL)TyrGln|SerSerSerNle-Acid (SEQ.ID.NO.: 158)
Ac-(imidazole)LysTyrGln|SerSerLeu-Acid (SEQ.ID.NO.: 159)
Ac-AlaAspLysAla(hArg)TyrGln|SerSerLeu-Acid (SEQ.ID.NO.: 160)
Ac-(p-NH2-Cha)TyrGln|SerSerSerNle-Acid (SEQ.ID.NO.: 161)
Ac(imidazolyl)LysTyrGln|SerSerSerNle-Acid (SEQ.ID.NO.: 162)
Ac-hArg(Cha)Gln|SerSerSerNle-Acid (SEQ.ID.NO.: 163)
Ac-hArgTyrGln|SerSerSerhArg-Acid (SEQ.ID.NO.: 164)
Ac-hArgTyrGln|SerSer(MeLeu) (SEQ.ID.NO.: 188)
Ac-hArgTyrGln1SerSerSer(Ethylester-Leu) (SEQ.ID.NO.: 156)
Ac-AlaAspLysAla(imidazoleLys)TyrGln|SerSerNle-Acid (SEQ.ID.NO.: 165)
Ac-hArg(3-Iodo-Tyr)Gln|SerSerSerNle-Acid (SEQ.ID.NO.: 166)
Ac-hArg(Me$_2$PO$_3$-Tyr)Gln|SerSerSerNle-Acid (SEQ.ID.NO.: 167)
Ac-hArgTyrGln|SerSerAsp-Acid (SEQ.ID.NO.: 168)
Ac-hArg(O-Me-Tyr)Gln|SerSerSerNle-Acid (SEQ.ID.NO.: 169)
Ac-AlaAspLysAlaLysTyrGln|SerSerNle-Acid (SEQ.ID.NO.: 170)
Ac-hArg(Cha)Gln|SerSerSer(ethylester-Leu) (SEQ.ID.NO.: 171)
Ac-(imidazolyl)Lys(Cha)Gln|SerSerSerNle-Acid (SEQ.ID.NO.: 172)
Ac-hArg(Cha)Gln|SerSerSer-Acid (SEQ.ID.NO.: 173)
Ac-hArg(Cha)Gln|SerSerNle-Acid (SEQ.ID.NO.: 174)
Ac-hArg(Cha)Gln|SerProNle-Acid (SEQ.ID.NO.: 175) and Ac-hArg(m-fluoro-Tyr)Gln|SerSerSerNle-Acid (SEQ.ID.NO.: 176), and the pharmaceutically acceptable salts.

A person of ordinary skill in the peptide chemistry art would readily appreciate that certain amino acids in a biologically active oligopeptide may be replaced by other homologous, isosteric and/or isoelectronic amino acids wherein the biological activity of the original oligopeptide has been conserved in the trodified oligopeptide. Certain unnatural and modified natural amino acids may also be utilized to replace the corresponding natural amino acid in the oligopeptides of the instant invention. Thus, for example, tyrosine may be replaced by 3-iodotyrosine, 2-methyltyrosine, 3-fluorotyrosine, 3-methyltyrosine and the like. Further for example, lysine may be replaced with N'-(2-imidazolyl)lysine and the like. The following list of amino acid replacements is meant to be illustrative and is not limiting:

| Original Amino Acid | Replacement Amino Acid(s) |
|---|---|
| Ala | Gly |
| Arg | Lys, Ornithine |
| Asn | Gln |
| Asp | Glu |
| Glu | Asp |
| Gln | Asn |
| Gly | Ala |
| Ile | Val, Leu, Met, Nle |
| Leu | Ile, Val, Met, Nle |
| Lys | Arg, Ornithine |
| Met | Leu, Ile, Nle, Val |
| Ornithine | Lys, Arg |
| Phe | Tyr, Trp |
| Ser | Thr |
| Thr | Ser |
| Trp | Phe, Tyr |
| Tyr | Phe, Trp |
| Val | Leu, Ile, Met, Nle |

Thus, for example, the following oligopeptides may be synthesized by techniques well known to persons of ordinary skill in the art and would be expected to be proteolytically cleaved by free PSA:

AsnArgIleSerTyrGln|Ser (SEQ.ID.NO.: 21)
AsnLysValSerTyrGln|Ser (SEQ.ID.NO.: 22)
AsnLysMetSerTyrGln|SerSer (SEQ.ID.NO.: 23)
AsnLysLeuSerTyrGln|SerSer (SEQ.ID.NO.: 24)
AsnLysIleThrTyrGln|SerSerSer (SEQ.ID.NO.: 25)
AsnLysIleSerPheGln|SerSerSer (SEQ.ID.NO.: 26)
AsnLysIleSerTrpGln|SerSerSerThr (SEQ.ID.NO.: 27)
AsnLysIleSerTyrAsn|SerSerSerThr (SEQ.ID.NO.: 28)
AsnLysIleSerTyrGln|ThrSerSerThr (SEQ.ID.NO.: 29)
AsnLysIleSerTyrGln|Ser (SEQ.ID.NO.: 30)
GlnLysIleSerTyrGln|SerSer (SEQ.ID.NO.: 31)
AsnArgIleThrTyrGln|SerSerSer (SEQ.ID.NO.: 32)
AsnArgIleSerPheGln|SerSerSerThr (SEQ.ID.NO.: 33)
AsnArgIleSerTrpGln|SerSerSerThr (SEQ.ID.NO.: 35)
AsnArgIleSerTyrGln|ThrSerSerThr (SEQ.ID.NO.: 36)
AsnLysIleThrTyrGln|ThrSerSerThr (SEQ.ID.NO.: 37)
AsnLysLeuSerTyrGln|ThrSerSerThr (SEQ.ID.NO.: 38)
GlnLysLeuSerTyrGln|SerSerSerThr (SEQ.ID.NO.: 39)
AsnArgLeuSerTyrGln|ThrSerSerThr (SEQ.ID.NO.: 40)
AsnLysValSerPheGln|SerSerSerThr (SEQ.ID.NO.: 41)
AsnArgValSerTrpGln|SerSerSerThr (SEQ.ID.NO.: 42)
GlnLysValSerTyrGln|SerSerSerThr (SEQ.ID.NO.: 43)
GlnLysIleSerTyrGln|ThrSerSerThr (SEQ.ID.NO.: 34)
AsnLysIleSerTyrGln|SerSerSerThr (SEQ.ID.NO.: 44);
or the pharmaceutically acceptable salts thereof.

Similarly, the following oligopeptides may be synthesized by techniques well known to persons of ordinary skill in the art and would be expected to be proteolytically cleaved by free PSA:

GlyGluGlnGlyValGlnLysAspValSerGlnSerSerIleTyr|SerGlnThrGlu (SEQ.ID.NO.: 45),
GlyGluAsnGlyLeuGlnLysAspValSerGlnSerSerIleTyr|SerGlnThrGlu (SEQ.ID.NO.: 47),
GlyGluAsnGlyValAsnLysAspValSerGlnSerSerIleTyr|SerGlnThrGlu (SEQ.ID.NO.: 48),
GlyGluAsnGlyValGlnArgAspValSerGlnArgSerIleTyr|SerGlnThrGlu (SEQ.ID.NO.: 49),
GlyGluAsnGlyValGlnLysAspValSerGlnLysSerIleTyr|SerGlnThrGlu (SEQ.ID.NO.: 50),
GlyGluAsnGlyValGlnLysAspLeuSerGlnThrSerIleTyr|SerGlnThrGlu (SEQ.ID.NO.: 51),
GlyGluAsnGlyValGlnLysAspValSerGlnSerSerIlePhe|SerGlnThrGlu (SEQ.ID.NO.: 52),
GlyGluAsnGlyValGlnLysAspMetSerGlnSerSerIleTyr|ThrGlnThrGlu (SEQ.ID.NO.: 53),
GlyGluAsnGlyValGlnLysAspValSerGlnArgSerIleTyr|ThrGlnThrGlu (SEQ.ID.NO.: 54),
GlyGluAsnGlyValGlnLysAspValSerGlnSerSerIleTyr|SerGlnSerGlu (SEQ.ID.NO.: 55),
GlyGluAsnGlyValGlnLysAspValSerGlnArgSerIleTyr|SerAsnThrGlu (SEQ.ID.NO.: 56),
GlyLysAlaIleSerSerGlnTyr|SerAsnThrGluGluArgLeu (SEQ.ID.NO.: 57),
GlyArgGlyIleSerSerGlnTyr|SerAsnThrGluGluArgLeu (SEQ.ID.NO.: 59),
GlyLysGlyIleThrSerGlnTyr|SerAsnThrGluGluArgLeu (SEQ.ID.NO.: 60),
GlyLysGlyIleSerThrGlnTyr|SerAsnThrCluGluArgLeu (SEQ.ID.NO.: 61),
GlyLysGlyIleSerSerAsnTyr|SerAsnThrGluGluArgLeu (SEQ.ID.NO.: 62),
AlaLysGlyIleSerSerGlnTyr|SerAsnThrGluGluArgLeu (SEQ ID.NO.: 63),
GlyLysGlyIleSerSerGlnPhe|SerAsnThrGluGluArgLeu (SEQ.ID.NO.: 64),
GlyLysGlyIleSerSerGlnTyr|ThrAsnThrGluGluArgLeu (SEQ.ID.NO.: 65),
GlyLysGlyIleSerSerGlnTyr|SerAsnSerGluGluArgLeu (SEQ.ID.NO.: 59), and
GlyLysGlyIleSerSerGlnTyr|SerAsnThrAspGluArgLeu (SEQ.ID.NO. 46);
and the like.

The inclusion of the symbol "|" within an amino acid sequence indicates the point within that sequence where the oligopeptide is proteolytically cleaved by free PSA.

The compounds of the present invention may have asymmetric centers and occur as racemates, racemic mixtures, and as individual diastereomers, with all possible isomers, including optical isomers, being included in the present invention. Unless otherwise specified, named amino acids are understood to have the natural "L" stereoconfiguration The following abbreviations are utilized in the specification and figures to denote the indicated amino acids and moieties:

hR or hArg: homoarginine
hY or hTyr: homotyrosine
Cha: cyclohexylalanine
Amf: 4-aminomethylphenylalanine DPL: 2-(4,6-dimethylpyrimidinyl)lysine
(imidazolyl)K: N'-(2-imidazolyl)lysine
Me$_2$PO$_3$—Y: O-dimethylphosphotyrosine
O—Me—Y: O-methyltyrosine
TIC: tetrahydro-3-isoquinoline carboxylic acid
MeL: 2-keto-3-amino-5-methylhexane
DAP: 1,3-diaminopropane
TFA: trifluoroacetic acid
AA: acetic acid The invention also concerns a method for assaying proteolytic free PSA activity in a composition. This is an important aspect of the invention in that such an assay system provides one with the ability to measure quantitatively the amount of free PSA present in certain physiological fluids and tissues much an assay will also provide not only the ability to follow isolation and purification of free PSA, but also is a basis for a screening assay for inhibitors of the proteolytic activity of free PSA. The assay method generally includes simply determining the ability of a composition suspected of containing enzymatically active free PSA to proteolytically cleave the oligopeptide.

Typically, the assay protocol is carried out using one of the oligopeptides described hereinabove. However, one may find a particular benefit in construction of an assay wherein the oligopeptide containing the cleavage site is labeled so that one can measure the appearance of such a label, for example, a radioactive label, in both the uncleaved oligopeptide and the portion of the oligopeptide remaining after cleavage which contains the label.

The instant invention further relates to a method for identifying compounds (hereinafter referred to as candidate compounds) that will inhibit the proteolytic activity of free PSA. It is contemplated that this screening technique will prove useful in the general identification of any candidate compound that will serve such as an inhibitory purpose, whether or not the candidate compound is proteinaceous or peptidyl in structure.

Thus, the present invention is also directed to a method for determining the ability of a test substance to inhibit the proteolytic activity of free PSA, the method which comprises:

(a) reacting a substrate, wherein the substrate comprises a sequence of amino acids that is recognized and selectively proteolytically cleaved by free prostate specific antigen, with free prostate specific antigen in the presence of a test substance; and (b) detecting whether the substrate has been cleaved, in which the ability of the test substance to inhibit proteolytic activity of prostate specific antigen is indicated by a decrease in the cleavage of the substrate as compared to the cleavage of the substrate in the absence of the test substance.

The candidate screening assay is quite simple to set up and perform, and is related in many ways to the assay discussed above for determining proteolytic activity. Thus, after obtaining a relatively purified preparation of free PSA, one will desire to simply admix a test substance with the proteolytic preparation, preferably under conditions which would allow the PSA to perform its cleavage function but for inclusion of a inhibitory substance. Thus, for example, one will typically desire to include within the admixture an amount of a known oligopeptide having a PSA specific cleavage site, such as those oligopeptides described hereinabove. In this fashion, one can measure the ability of the test substance to reduce cleavage of the oligopeptide relatively in the presence of the test substance.

Accordingly, one will desire to measure or otherwise determine the activity of the free PSA in the absence of the added test substance relative to the activity in the presence of the test substance in order to assess the relative inhibitory capability of the test substance.

The instant invention also relates to novel anti-cancer compositions useful for the treatment of prostate cancer. Such compositions comprise the oligopeptides of the instant invention covalently bonded directly, or through a chemical linker, to a cytotoxic agent. Such a combination of an oligopeptide and cytotoxic agent may be termed a conjugate. Ideally, the cytotoxic activity of the cytotoxic agent is greatly reduced or absent when the oligopeptide containing the PSA proteolytic cleavage site is bonded directly, or through a chemical linker, to the cytotoxic agent and is intact Also ideally, the cytotoxic activity of the cytotoxic agent increases significantly or returns to the activity of the unmodified cytotoxic agent upon proteolytic cleavage of the attached oligopeptide at the cleavage site. While it is not necessary for practicing this aspect of the invention, a preferred embodiment of this aspect of the invention is a conjugate wherein the oligopeptide, and the chemical linker if present, are detached from the cytotoxic agent by the proteolytic activity of the free PSA and any other native proteolytic enzymes present in the tissue proximity, thereby releasing unmodified cytotoxic agent into the physiological environment at the place of proteolytic cleavage. Pharmaceutically acceptable salts of the conjugates are also included.

It is understood that the oligopeptide of the instant invention that is conjugated to the cytotoxic agent, whether through a direct covalent bond or through a chemical linker, does not need to be the oligopeptide that has the greatest recognition by free PSA and is most readily proteolytically cleaved by free PSA. Thus, the oligopeptide that is selected for incorporation in such an anti-cancer composition will be chosen both for its selective, proteolytic cleavage by free PSA and for the cytotoxic activity of the cytotoxic agent-proteolytic residue conjugate (or, in what is felt to be an ideal situation, the unmodified cytotoxic agent) which results from such a cleavage.

Because the conjugates of the invention can be used for modifying a given biological response, cytotoxic agent is not to be construed as limited to classical chemical therapeutic agents. For example, the cytotoxic agent may be a protein or polypeptide possessing a desired biological activity Such proteins may include, for example, a toxin such as abrin, ricin A, pseudomonas exotoxin, or diphtheria toxin; a protein such as tumor necrosis factor, (α-interferon, β-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

The preferred cytotoxic agents include, in general, alkylating agents, antiproliferative agents, tubulin binding agents and the like. Preferred classes of cytotoxic agents include, for example, the anthracycline family of drugs, the vinca drugs, the mitomycins, the bleomycins, the cytotoxic nucleosides, the pteridine family of drugs, diynenes, and the podophyllotoxins. Particularly useful members of those classes include, for example, doxorubicin, carminomycin, daunorubicin, aminopterin, methotrexate, methopterin, dichloromethotrexate, mitomycin C, porfiromycin, 5-fluorouracil, 6-mercaptopurine, cytosine arabinoside, podophyllotoxin, or podophyllotoxin derivatives such as etoposide or etoposide phosphate, melphalan, vinblastine, vincristine, leurosidine, vindesine, leurosine and the like. Other useful cytotoxic agents include estramustine, cisplatin and cyclophosphamide. One skilled in the art may make chemical modifications to the desired cytotoxic agent in order to make reactions of that compound more convenient for purposes of preparing conjugates of the invention.

A highly preferred group of cytotoxic agents for the present invention include drugs of the following formulae:
The Methotrexate Group of Formula(1):

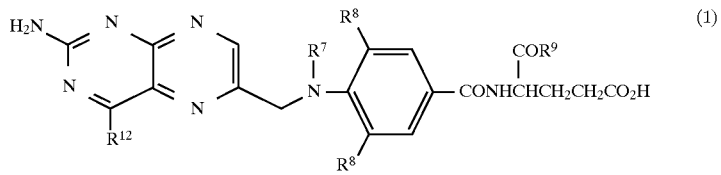

in which
- $R^{12}$ is amino or hydroxy;
- $R^7$ is hydrogen or methyl;
- $R^8$ is hydrogen, fluoro, chloro, bromo or iodo;
- $R^9$ is hydroxy or a moiety which completes a salt of the carboxylic acid;

The Mitomycin Group of Formula (2):

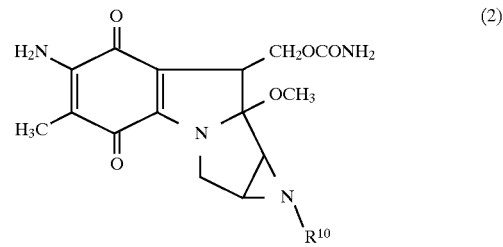

in which $R^{10}$ is hydrogen or methyl;

The Bleomycin Group Of Formula (3)

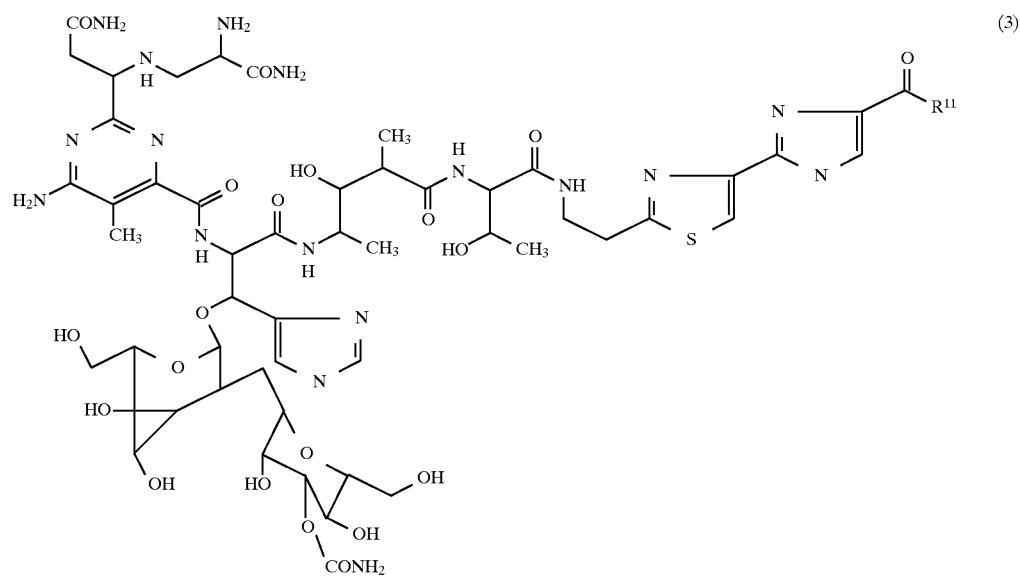

in which $R^{11}$ is hydroxy, amino, $C_1$–$C_3$ alkylamino, di($C_1$–$C_3$ alkyl)amino, $C_4$–$C_6$ polymethylene amino,

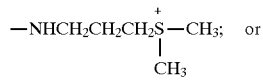

or

Melphalan Of Formula (4):

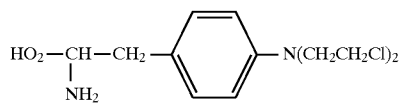
(4)

6-Mercaptopurine of Formula (5):

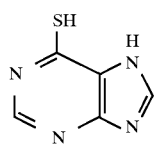
(5)

A Cytosine Arabinoside of Formula (6):

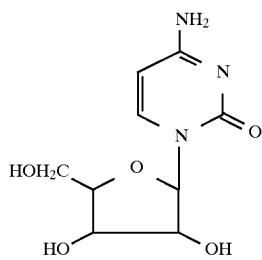
(6)

The Podophyllotoxins Of Formula(7):

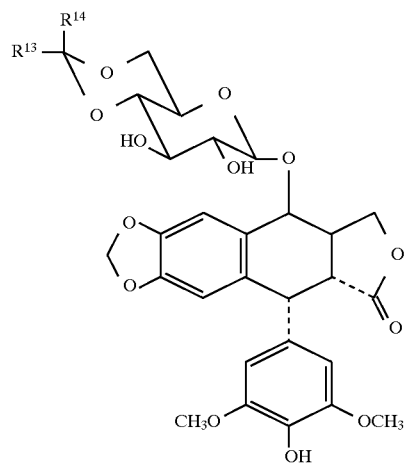
(7)

in which $R^{13}$ is hydrogen or methyl;

$R^{14}$ is methyl or thienyl;

or a phosphate salt thereof;

The Vinca Alkaloid Group of Drugs of Formula (8):

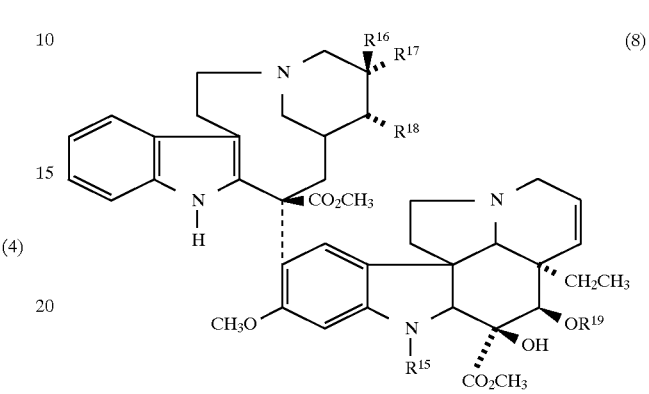
(8)

in which $R^{15}$ is H, $CH_3$ or CHO; when $R^{17}$ and $R^{18}$ are taken singly;

$R^{18}$ is H, and one of $R^{16}$ and $R^{17}$ is ethyl and the other is H or OH; when $R^{17}$ and $R^{18}$ are taken together with the carbons to which they are attached, they form an oxirane ring in which case $R^{16}$ is ethyl;

$R^{19}$ is hydrogen, ($C_1$–$C_3$ alkyl)-CO, or chlorosubstituted ($C_1$–$C_3$ alkyl)-CO;

Difluoronucleosides of Formula (9):

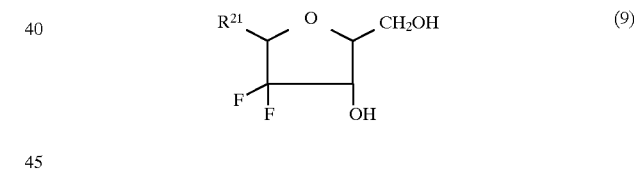
(9)

in which $R^{21}$ is a base of one of the formulae:

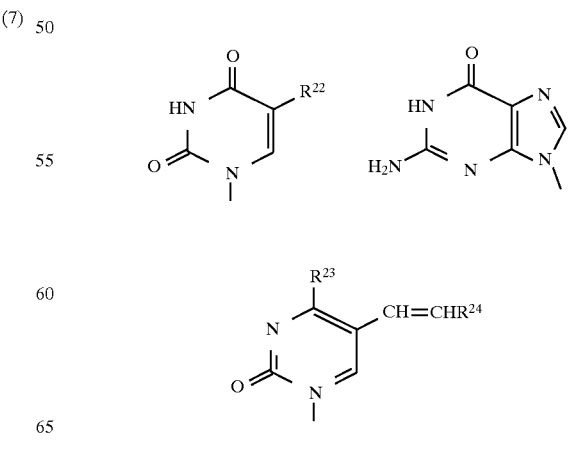

-continued

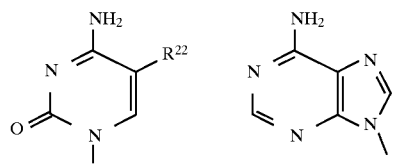

in which
R$^{22}$ is hydrogen, methyl, bromo, fluoro, chloro or iodo;
R$^{23}$ is —OH or —NH$_2$;
R$^{24}$ is hydrogen, bromo, chloro or iodo; or,
The Anthracyclines Anti-Biotics of Formula (10):

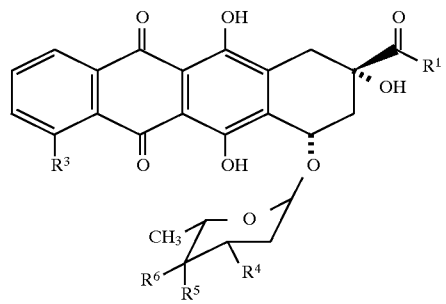

wherein
R$^1$ is —CH$_3$, —CH$_2$OH, —(CH$_2$OCO(CH$_2$)$_3$CH$_3$, or —CH$_2$OCOCH(OC$_2$H$_5$)$_2$;

R$^3$ is —OCH$_3$, —OH or —H;
R$^4$ is —NH$_2$, —NHCOCF$_3$, 4-morpholinyl, 3-cyano-4-morpholinyl, 1-piperidinyl, 4-methoxy-1-piperidinyl, benzylamine, dibenzylamine, cyanomethylamine, or 1-cyano-2-methoxyethyl amine;

R$^5$ is —OH—OTHP or —H; and
R$^6$ is —OH or —H provided that R$^6$ is not —OH when R$^5$ is —OH or —OTHP.

Estramustine (11)

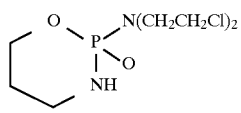

Cyclophosphamide (12)

$$\underset{NH}{\overset{O}{\underset{|}{P}}} \; N(CH_2CH_2Cl)_2 \quad (12)$$

The most highly preferred drugs are the anthracycline antiobiotic agents of Formula (10), described previously. One skilled in the art understands that this structural formula includes compounds which are drugs, or are derivatives of drugs, which have acquired in the art different generic or trivial names. Table 1, which follows, represents a number of anthracycline drugs and their generic or trivial names and which are especially preferred for use in the present invention.

TABLE 1

| Compound | R$_1$ | R$_3$ | R$_4$ | R$_5$ | R$_6$ |
|---|---|---|---|---|---|
| daunorubicin[a] | CH$_3$ | OCH3 | NH$_2$ | OH | H |
| doxorubicin[b] | CH$_2$OH | OCH$_3$ | NH$_2$ | OH | H |
| detorubicin | CH$_2$OCOCH(OC$_2$H$_5$)$_2$ | OCH$_3$ | NH$_2$ | OH | H |
| carminomycin | CH$_3$ | OH | NH$_2$ | OH | H |
| idarubicin | CH$_3$ | H | NH$_2$ | OH | H |
| epirubicin | CH$_2$OH | OCH$_3$ | NH$_2$ | OH | OH |
| esorubicin | CH$_2$OH | OCH$_3$ | NH$_2$ | H | H |
| THP | CH$_2$OH | OCH$_3$ | NH$_2$ | OTHP | H |
| AD-32 | CH$_2$OCO(CH$_2$)$_3$CH$_3$ | OCH$_3$ | NHCOCF$_3$ | OH | H |

[a]"daunomycin" is an alternative name for daunorubicin
[b]"adriamycin" is an alternative name for doxorubicin Of the compounds shown in Table 1, the most highly preferred cytotoxic agents are doxerubicin, vinblastine and desacetylvinblastine. Doxorubicin (also referred to herein as "DOX") is that anthracycline of Formula (10) In which $R_1$ is —$CH_2OH$, $R_3$ is —$OCH_3$, $R^4$ is —$NH_2$, $R_5$ is —OH, and $R_6$ is —H.

The oligopeptides, peptide subunits and peptide derivatives (also termed "peptides") of the present invention can be synthesized from their constituent amino acids by conventional peptide synthesis techniques, preferably by solid-phase technology The peptides are then purified by reverse-phase high performance liquid chromatography (HPLC).

Standard methods of peptide synthesis are disclosed, for example, in the following works: Schroeder et al., "The Peptides", Vol. I, Academic Press 1965; Bodansky et al., "Peptide Synthesis", Interscience Publishers, 1966; McOmie (ed.) "Protective Groups in Organic Chemistry", Plenum Press, 1973; Barany et al., "The Peptides: Analysis, Synthesis, Biology" 2, Chapter 1, Academic Press, 1980, and Stewart et al., "*Solid Phase Peptide Synthesis*", Second Edition, Pierce Chemical Company, 1984. The teachings of these works are hereby incorporated by reference.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenyl-acetic, glutamic, benzoic, salicylic, sulfanilic, 2-aceloxy-benzoic, fumaric, toluenesulfonic, methanesulfonic, ethane disulfonic, oxalic, isethionic, trifluoroacetic and the like.

The conjugates of the instant invention which comprise the oligopeptide containing the PSA cleavage site and a cytotoxic agent may similarly be synthesized by techniques well known in the medicinal chemistry art. For example, a free amine moiety on the cytotoxic agent may be covalently attached to the oligopeptide at the carboxyl terminus such that an amide bond is formed. Similarly, an amide bond may be formed by covalently coupling an amine moiety of the oligopeptide and a carboxyl moiety of the cytotoxic agent. For these purposes a reagent such as 2-(1H-benzotriazol-1-yl)-1,3,3-tetramethyluronium hexafluorophosphate (known as HBTU) and 1-hyroxybenzotriazole hydrate (known as HOBT), dicyclohexyl-carbodiimide (DCC), N-ethyl-N-(3-dimethylaminopropyl)-carbodiimide (EDC), diphenylphosphorylazide (DPPA), benzotriazol-1-yl-oxy-tris-(dimethylamino)phosphonium hexifluorophosphate (BOP) and the like, used in combination or singularly, may be utilized Furthermore, the instant conjugate may be formed by a non-peptidyl bond between the PSA cleavage site and a cytotoxic agent. For example, the cytotoxic agent may be covalently attached to the carboxyl terminus of the oligopeptide via a hydroxyl moiety on the cytotoxic agent, thereby forming an ester linkage For this purpose a reagent such as a combination of HBTU and HOBT, a combination of BOP and imidazole, a combination of DCC and DMAP, and the like may be utilized. The carboxylic acid may also be activated by forming the nitrophenyl ester or the like and reacted in the presence of DBU (1,8-diazabicycloL5,4,0]undec-7-ene.

The instant conjugate may also be formed by attachment of the oligopeptide to the cytotoxic agent via a linker unit. Such linker units include, for example, a biscarbonyl alkyl diradical whereby an amine moiety on the cytotoxic agent is connected with the linker unit to form an amide bond and the amino terminus of the oligopeptide is connected with the other end of the linker unit also forming an amide bond. Conversely, a diaminoalkyl diradical linker unit, whereby a carbonyl moiety on the cyctotoxic agent is covalently attacted to one of the amines of the linker unit while the other amine of the linker unit is covalently attached to the C terminus of the oligopeptide, may also be uselful. Other such linker units which are stable to the physiological environment when not in the presence of free PSA, but are cleavable upon the cleavage of the PSA proteolytic cleavage site, are also envisioned. Furthermore, linker units may be utilized that, upon cleavage of the PSA proteolytic cleavage site, remain attached to the cytotoxic agent but do not significantly decrease the cytotoxic activity of such a post-cleavage cytotoxic agent derivative when compared with an unmodified cytotoxic agent.

One skilled in the art understands that in the synthesis of compounds of the invention, one may need to protect or block various reactive functionalities on the starting compounds and intermediates while a desired reaction is carried out on other portions of the molecule. After the desired reactions are complete, or at any desired time, normally such protecting groups will be removed by, for example, hydrolytic or hydrogenolytic means. Such protection and deprotection steps are conventional in organic chemistry. One skilled in the art is referred to *Protective Groups in Organic Chemistry*, McOmie, ed., Plenum Press, NY, N.Y. (1973); and, *Protective Groups in Organic Synthesis*, Greene, ed., John Wiley & Sons, NY, N.Y. (1981) for the teaching of protective groups which may be useful in the preparation of compounds of the present invention.

By way of example only, useful amino-protecting groups may include, for example, $C_1$–$C_{10}$ alkanoyl groups such as formyl, acetyl, dichloroacetyl, propionyl, hexanoyl, 3,3-diethylhexanoyl, γ-chlorobutryl, and the like; $C_1$–$C_{10}$ alkoxycarbonyl and $C_5$–$C_{15}$ aryloxycarbonyl groups such as tert-butoxycarbonyl, benzyloxycarbonyl, allyloxycarbonyl, 4-nitrobenzyloxycarbonyl, fluorenylmethyloxycarbonyl and cinnamoyloxycarbonyl; halo-($C_1$–$C_{10}$)-alkoxycarbonyl such as 2,2,2-trichloroethoxycarbonyl; and $C_1$–$C_{15}$ arylalkyl and alkenyl group such as benzyl, phenethyl, allyl, trityl, and the like. Other commonly used amino-protecting groups are those in the form of enamines prepared with β-keto-esters such as methyl or ethyl acetoacetate.

Useful carboxy-protecting groups may include, for example, $C_1$–$C_{10}$ alkyl groups such as methyl, tert-butyl, decyl; halo-$C_1$–$C_{10}$ alkyl such as 2,2,2-trichloroethyl, and 2-iodoethyl; $C_5$–$C_{15}$ arylalkyl such as benzyl, 4-methoxybenzyl, 4-nitrobenzyl, triphenylmethyl, diphenylmethyl; $C_1$–$C_{10}$ alkanoyloxymethyl such as acetoxymethyl, propionoxymethyl and the like; and groups such as phenacyl, 4-halophenacyl, allyl, dimethylallyl, tri-($C_1$–$C_3$ alkyl)silyl, such as trimethylsilyl, β-p-toluenesulfonylethyl, β-p-nitrophenyl-thioethyl, 2,4,6-trimethylbenzyl, β-methylthioethyl, phthalimidomethyl, 2,4-dinitrophenylsulphenyl, 2-nitrobenzhydryl and related groups.

Similarly, useful hydroxy protecting groups may include, for example, the formyl group, the chloroacetyl group, the benzyl group, the benzhydryl group, the trityl group, the 4-nitrobenzyl group, the trimethylsilyl group, the phenacyl group, the tert-butyl group, the methoxymethyl group, the tetrahydropyranyl group, and the like.

With respect to the preferred embodiment of an oligopeptide combined with the anthracycline antibiotic doxorubicin, the following Reaction Schemes illustrate the synthesis of the conjugates of the instant invention.

REACTION SCHEME I
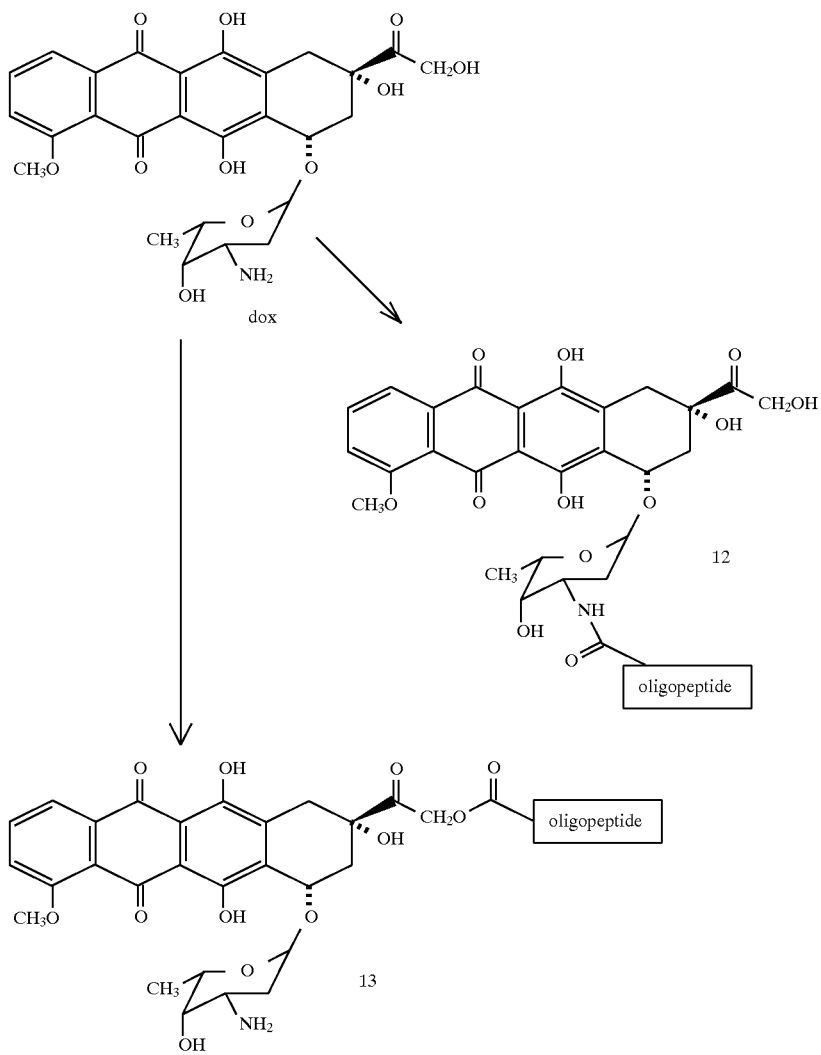
REACTION SCHEME II
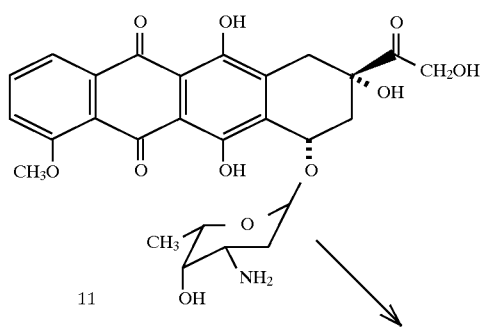

-continued
REACTION SCHEME II
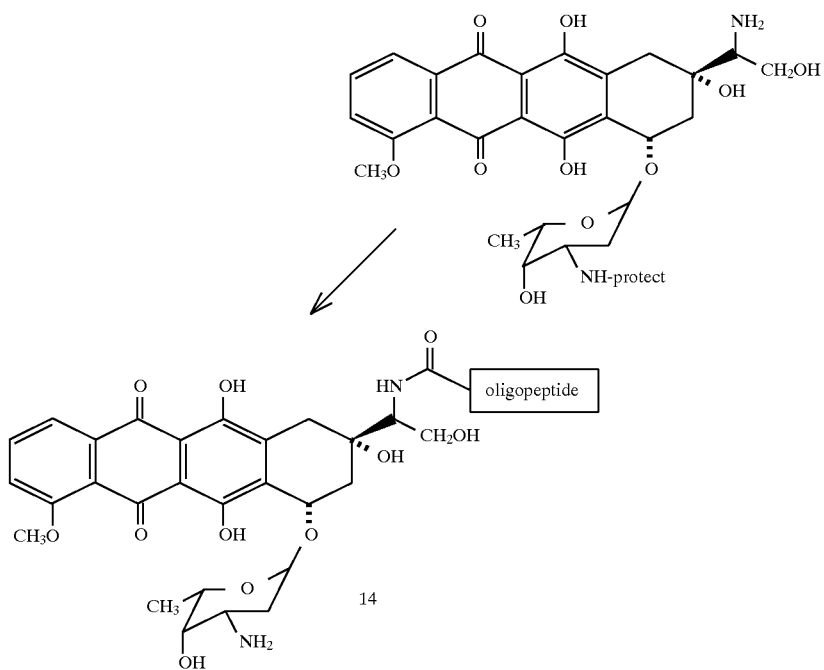
REACTION SCHEME III
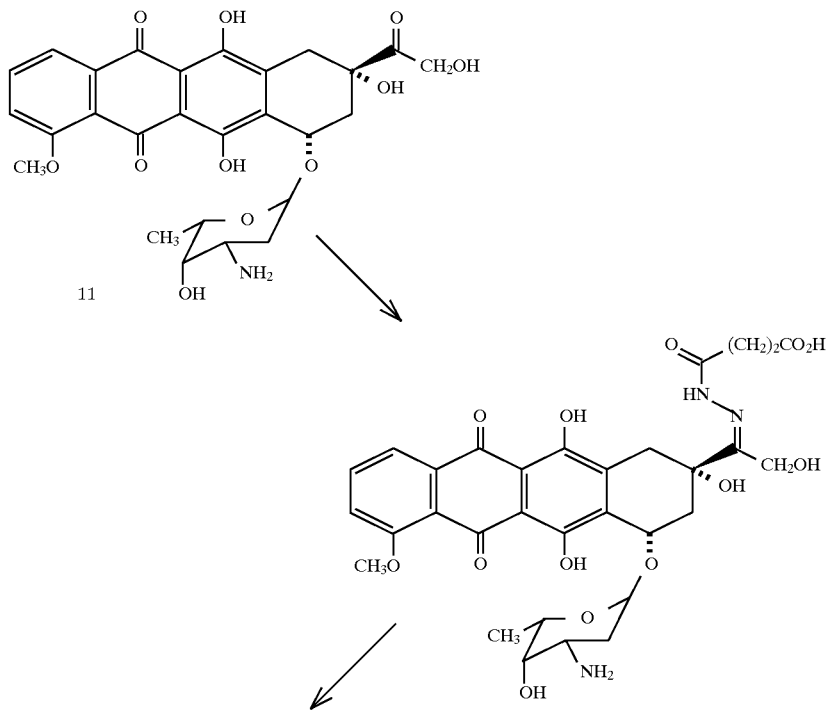

-continued
REACTION SCHEME III
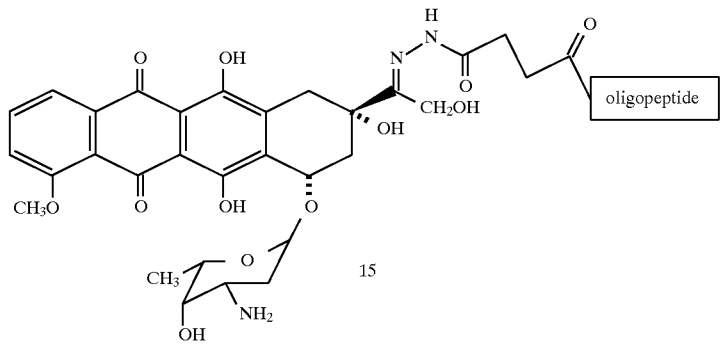
REACTION SCHEME IV
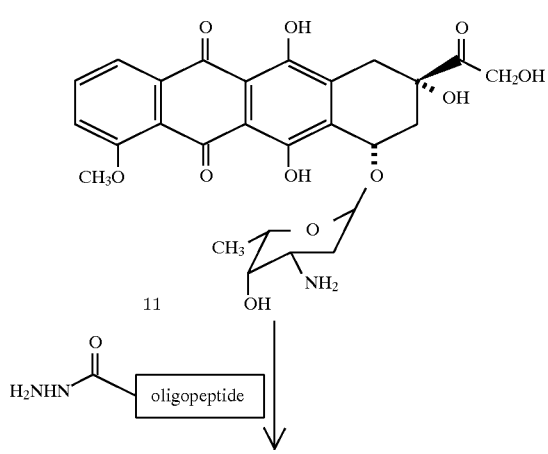
-continued
REACTION SCHEME IV
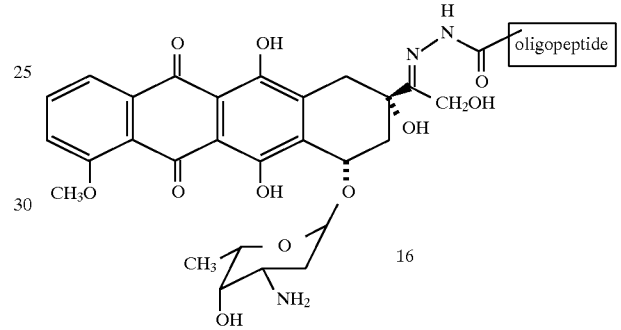
REACTION SCHEME V
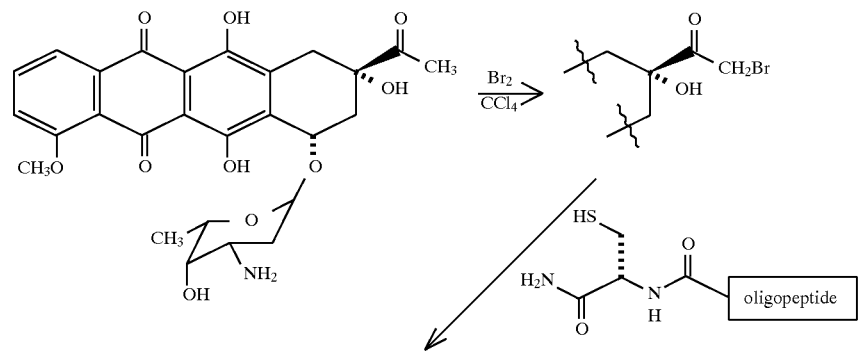

-continued
REACTION SCHEME V

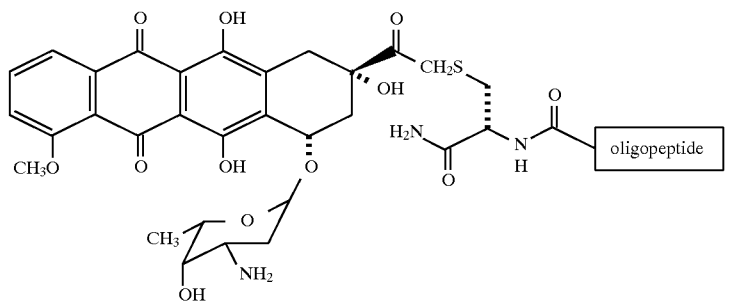

Reaction Scheme VI illustrates preparation of conjugates of the oligopeptides of the instant invention and the vinca alkaloid cytotoxic agent vinblastine. Attachment of the N-terminus of the oligopeptide to vinblastine is illustrated (S. P. Kandukuri et al. J. Med. Chem. 28:1079–1088 (1985)).

Reaction Scheme VII Illustrates preparation of conjugates of the oligopeptides of the instant invention and the vinca alkaloid cytotoxic agent vinblastine wherein the attachment of vinblastine is at the C-terminus of the oligopeptide. The use of the 1,3-diaminopropane linker is illustrative only; other spacer units between the carbonyl of vinblastine and the C-terminus of the oligopeptide are also envisioned. Furthermore, Scheme VII illustrates a synthesis of conjugates wherein the C-4-position hydroxy moiety is reacetylated following the addition of the linker unit. Applicants have discovered that the desacetyl vinblastine conjugate is also efficacious and may be prepared by eliminating the steps shown in Reaction Scheme VII of protecting the primary amine of the linker and reacting the intermediate with acetic anhydride, followed by deprotection of the amine. Conjugation of the oligopeptide at other positions and functional groups of vinblastine may be readily accomplished by one of ordinary skill in the art and is also expected to provide compounds useful in the treatment of prostate cancer.

It is also understood that conjugates may be prepared wherein the N-terminus of the oligopeptide of the instant invention is covalently attached to one cytotoxic agent, such as vinblastine, while the C-terminus is simultaneously attached to another cytotoxic agent, which is the same or different cytotoxic agent, such as doxorubicin. Reaction Scheme VIII illustrates the synthesis of such a polycytotoxic agent conjugate. Such a polycytotoxic conjugate may offer advantages over a conjugate containing only one cytctoxic agent.

REACTION SCHEME VI

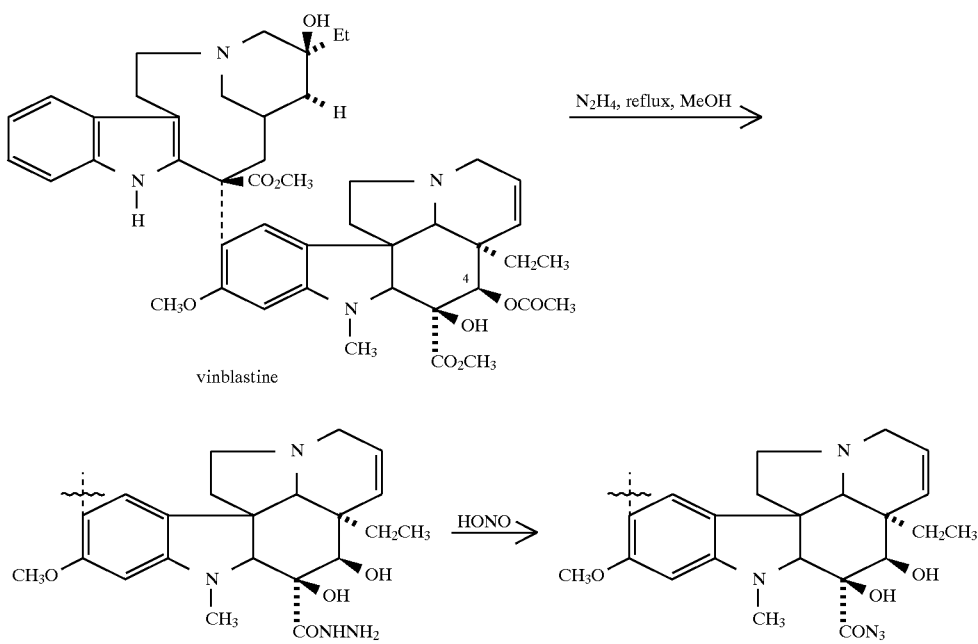

REACTION SCHEME VI
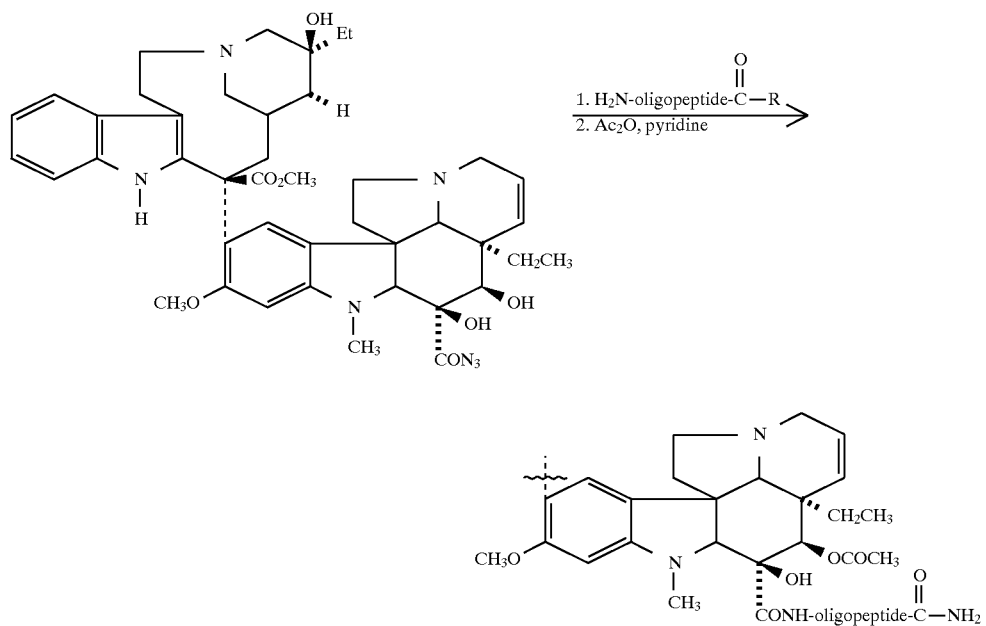
wherein R is —NH₂, —O-alkyl and the like
REACTION SCHEME VII
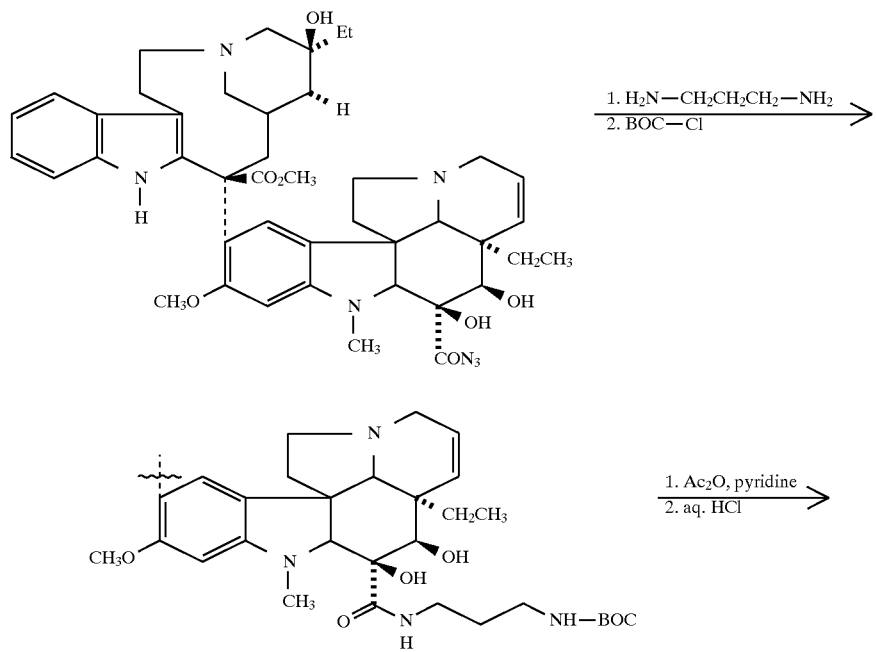

-continued
REACTION SCHEME VII
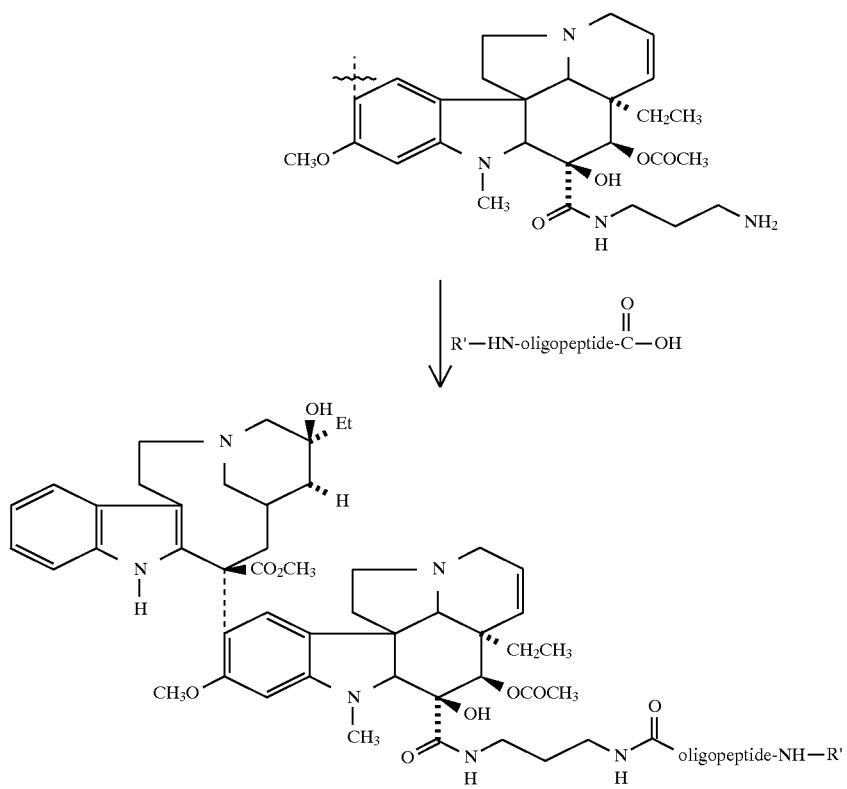
wherein R' is acetyl, alkyl, hydrogen or the like
REACTION SCHEME VIII
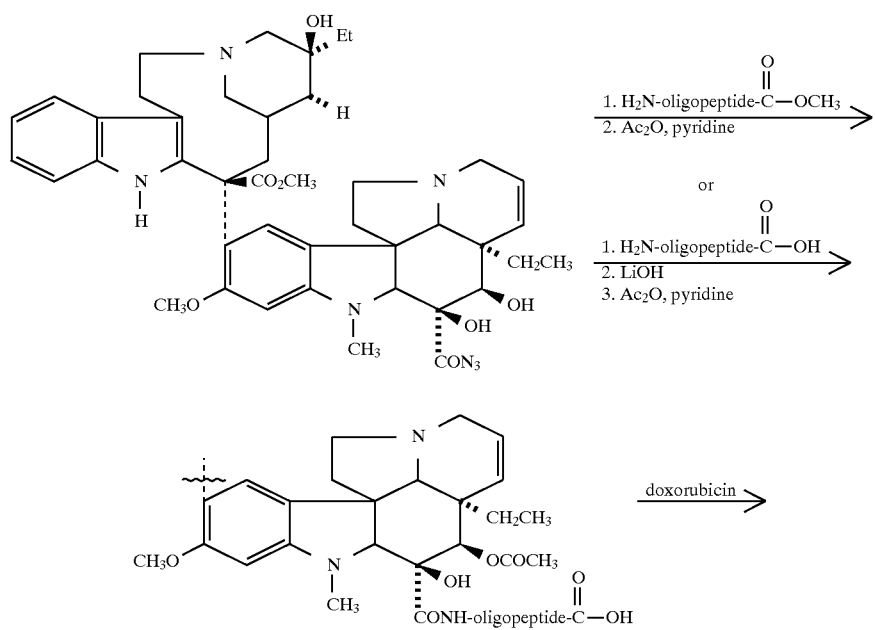

-continued
REACTION SCHEME VIII

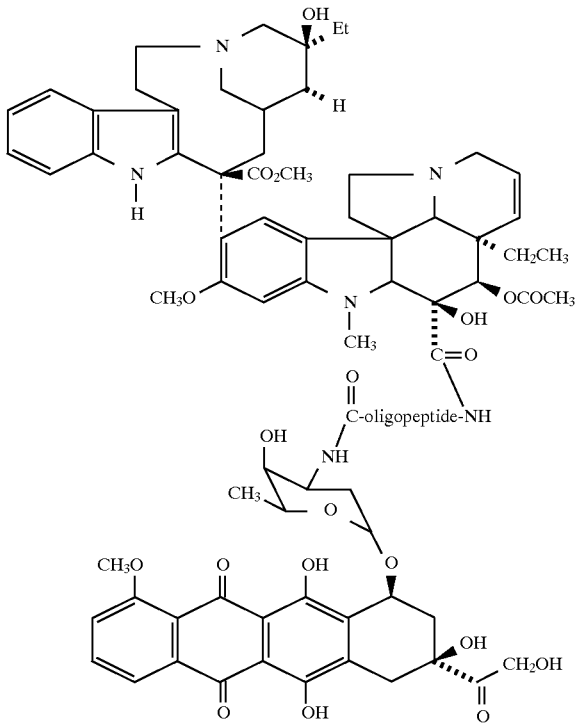

The oligopeptide-cytotoxic agent conjugate of the instant invention wherein the cytotoxic agent is the preferred cytotoxic agent doxorubicin may be described by the general formula I below:

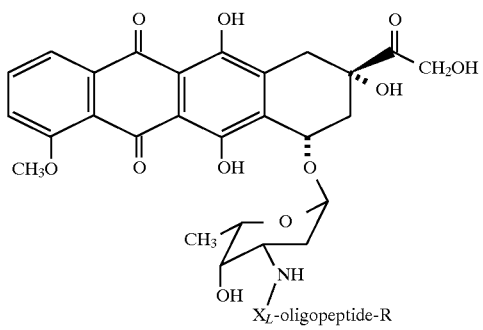

wherein:
oligopeptide is an oligopeptide which is specifically recognized by the free prostate specific antigen (PSA) and is capable of being proteolytically cleaved by the enzymatic activity of the free prostate specific antigen;
XL is absent or is an amino acid selected from:
a) phenylalanine,
b) leucine,
c) valine,
d) isoleucine,
e) (2-naphthyl)alanine,
f) cyclohexylalanine,
g) diphenylalanine,
h) norvaline, and
j) norleucine;
R is hydrogen or —(C=O)R$^1$; and
R$^1$ is C$_1$–C$_6$-alkyl or aryl, or the pharmaceutically acceptable salt thereof.

In a preferred embodiment of the oligopeptide-cytotoxic agent conjugate:

oligopeptide is an oligomer that comprises an amino acid sequence selected from:
a) AsnLysIleSerTyrGln|Ser (SEQ.ID.NO.: 13),
b) LysIleSerTyrGln|Ser (SEQ.ID.NO.: 14),
c) GlyGluAsnGlyValGlnLysAspValSerGlnXaaSerIle Tyr|SerGlnThrGlu (SEQ.ID.NO.: 15),
d) GlyLysGlyIleSerSerGlnTyr|SerAsnThrGluGlu ArgLeu (SEQ.ID.NO.: 2),
e) AsnLysIleSerTyrTyr|Ser (SEQ.ID.NO.: 127),
f) AsnLysAlaSerTyrGln|Ser (SEQ.ID.NO.: 128),
g) SerTyrGln|SerSer (SEQ.ID.NO.: 129),
h) LysTyrGln|SerSer (SEQ.ID. NO.: 140);
i) hArgTyrGln|SerSer (SEQ.ID.NO.: 141);
j) hArgChaGln|SerSer (SEQ.ID.NO.: 185); and
k) TyrGln|SerSer (SEQ.ID.NO.: 186);

wherein Xaa is any natural amino acid;

X$_L$ is absent or is an amino acid selected from:
a) leucine,
b) isoleucine,
c) norleucine, and
d) valine; and R is acetyl, pivaloyl or benzoyl, or the pharmaceutically acceptable salt thereof.

The following compounds are specific examples of the oligopeptide-cytotoxic agent conjugate of the instant invention:

33

[Structure of doxorubicin derivative with substituents: CH₃O, OH, O, CH₂OH, OH, CH₃, OH groups on the tetracyclic ring system with sugar moiety at 3' position bearing NH-X]

wherein X is:

| | |
|---|---|
| H₂N—AsnLysIleSerTyrGlnSer—C(=O)— | (SEQ. ID. NO.: 13), |
| H₂N—AsnLysIleSerTyrGlnSerSer—C(=O)— | (SEQ. ID. NO.: 16), |
| H₂N—AsnLysIleSerTyrGlnSerSer—C(=O)— | (SEQ. ID. NO.: 17), |
| H₂N—AsnLysIleSerTyrGlnSerSerThr—C(=O)— | (SEQ. ID. NO.: 10), |
| H₂N—AsnLysIleSerTyrGlnSerSerThrGlu—C(=O)— | (SEQ. ID. NO.: 3), |
| H₂N—AlaAsnLysIleSerTyrGlnSerSerThrGlu—C(=O)— | (SEQ. ID. NO.: 11), |
| AcHN—AlaAsnLysIleSerTyrGlnSerSerThr—C(=O)— | (SEQ. ID. NO.: 117), |
| AcHN—AlaAsnLysIleSerTyrGlnSerSerThrLeu—C(=O)— | (SEQ. ID. NO.: 70), |
| AcHN—AlaAsnLysSerTyrGlnSerAlaSerThrLeu—C(=O)— | (SEQ. ID. NO.: 118), |
| AcHN—AlaAsnLysAlaSerTyrGlnSerAlaSerLeu—C(=O)— | (SEQ. ID. NO.: 119), |
| AcHN—AlaAsnLysAlaSerTyrGlnSerSerSerLeu—C(=O)— | (SEQ. ID. NO.: 120), |
| AcHN—AlaAsnLysAlaSerTyrGlnSerSerLeu—C(=O)— | (SEQ. ID. NO.: 121). |
| AcHN—SerTyrGlnSerSerSerLeu—C(=O)— | (SEQ. ID. NO.: 144), |
| AcHN—hArgTyrGlnSerSerSerLeu—C(=O)— | (SEQ. ID. NO.: 145). |
| AcHN—LysTyrGlnSerSerSerLeu—C(=O)— | (SEQ. ID. NO.: 124), or (Compound 4) |
| AcHN—LysTyrGlnSerSerNle—C(=O)— | (SEQ. ID. NO.: 146). |

34 or the pharmaceutically acceptable salt thereof.

Further examples of conjugates of an oligopeptide and doxorubicin wherein the N-terminus of the oligopeptide is acylated and the C-terminus of the oligopeptide is attached to the doxorubicin at the 3'-amine are as follows:

Ac-hArgTyrGln-SerSerPro-dox(3') (SEQ.ID.NO.: 151)
Ac-hArgTyrGln-SerPro-dox(3') (SEQ.ID.NO.: 177)
Ac-hArgTyrGln-SerSerSerNle-dox(3') (SEQ.ID.NO.: 154)
Ac-AmfTyrGln-SerSerSerNle-dox(3') (SEQ.ID.NO.: 155)
H₂NCO-hArgTyrGln-SerSerSerLeu-dox(3') (SEQ.ID.NO.: 156)
Ac-LysTyrGln-SerSerNle-dox(3') (SEQ.ID.NO.: 146)
Ac-LysTyrGln-SerLysNle-dox(3') (SEQ.ID.NO.: 178)

Ac(cis-p-NH$_2$Cha)TyrGlnSerSerNledox(3') (SEQ.ID.NO.: 161)

Ac-AlaAspLysAla(hArg)TyrGln-SerSerLeu-dox(3') (SEQ.ID.NO.: 160)

Ac-hArgTyrGln-SerAsn-dox(3') (SEQ.ID.NO.: 153)

Ac-hArgTyrGln-SerSerHis-dox(3') (SEQ.ID.NO.: 152)

Ac-(imidazolyl)LysTyrGln-SerSerLeu-dox(3') (SEQ.ID.NO.: 159)

Ac-(imidazolyl)LysTyrGlnSerSerScrNle-dox(3') (SEQ.ID.NO.: 162)

Ac-hArg(Cha)Gln-SerSerSerNle-dox(3') (SEQ.ID.NO.: 163)

Ac-hArg(Me$_2$PO$_3$Tyr)Gln-SerSerSerNle-dox(3') (SEQ.ID.NO.: 167)

Ac-hArgTyrGln-SerSerSerhArg-dox(3') (SEQ.ID.NO.: 164)

Ac-hArg(3-Iodo-Tyr)Gln-SerSerSerNle-dox(3') (SEQ.ID.NO.: 166)

Ac-hArg(O-Me-Tyr)Gln-SerSerSerNle-dox(3') (SEQ.ID.NO.: 169)

Ac-hArg(p-NH$_2$-Phe)Gln-SerSerSerNle-dox(3') (SEQ.ID.NO.: 179)

Ac-hArg(Cha)Gln-SerSerNle-dox(3') (SEQ.ID.NO.: 174)

Ac-hArg(Cha)Gln-SerProNle-dox(3') (SEQ.ID.NO.: 175)

Ac(imidazolyl)Lys(Cha)GlnSerSerSerNle-dox(3') (SEQ.ID.NO.: 172)

Ac-hArg(7-HO-TIC)Gln-SerSerSerNle-dox(3') (SEQ.ID.NO.: 180)

Ac-hArg(3-Fluoro)TyrGlnSerSerSerNle-dox(3') (SEQ.ID.NO.: 176)

Ac-(omithine)TyrGln-SerSerSerNle-dox(3') (SEQ.ID.NO.: 181)

Ac-LysAlaAlaSerSerSerLeu-dox(3') (SEQ.ID.NO.: 183)

Ac-hArgh(Cha)Gln-SerSerNle-dox(3') (SEQ.ID.NO.: 149)

Ac-AlaArgLysAlaSerTyrGln-SerLeu-dox(3') (SEQ.ID.NO.: 193) and

Ac-(Orn)TyrGln-SerSerSerLeu-dox(3') (SEQ.ID.NO.: 194)

or the pharmaceutically acceptable salt thereof.

The oligopeptide-cytotoxic agent conjugate of the instant invention wherein the cytotoxic agent is the preferred cytotoxic agent vinblastine or desacetylvinblastine may be described by the general formula I below:

[Structure of formula I with X$_L$-oligopeptide-R substituent]

wherein:

oligopeptide is an oligopeptide which is specifically recognized by the free prostate specific antigen (PSA) and is capable of being proteolytically cleaved by the enzymatic activity of the free prostate specific antigen;

XL is absent or is an amino acid selected from:
a) phenylalanine,
b) leucine,
c) valine,
d) isoleucine,
e) (2-naphthyl)alanine,
f) cyclohexylalanine,
g) diphenylalanine,
h) norvaline, and
j) norleucine; or XL is —NH—(CH$_2$)$_n$—NH—

R is hydrogen or —(C=O)R$^1$;

R$^1$ is C$_1$–C$_6$-alkyl or aryl;

R$^{19}$ is hydrogen or acetyl; and n is 1, 2, 3, 4 or 5, or the pharmaceutically acceptable salt thereof.

The following compounds are specific examples of the oligopeptide-desacetylvinblastine conjugate of the instant invention:

[Structure of Compound 14 with AcHN—LysTyrGlnSerSerSerNle—C(=O)—NH substituent]

Compound 14

AcHN—LysTyrGlnSerSerSerNle—C(=O)—NH (SEQ. ID. NO.: 183),

-continued

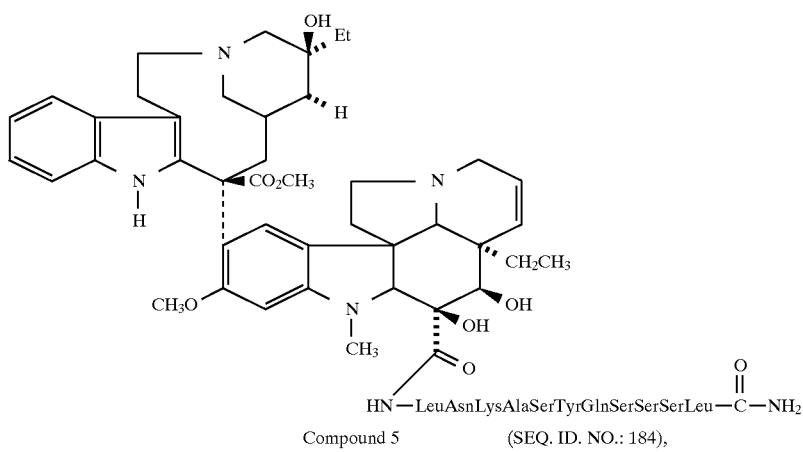

Compound 5 (SEQ. ID. NO.: 184), or the pharmaceutically acceptable salt thereof.

The following compounds is a specific example of the polycytotoxic agent conjugates of the instant invention:

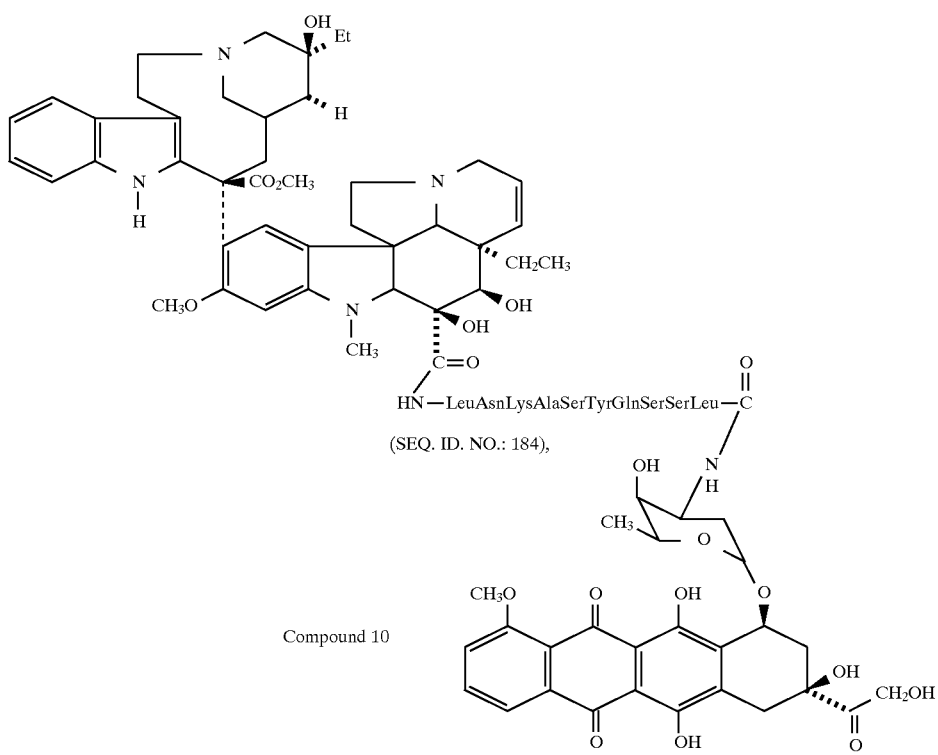

Compound 10 or the pharmaceutically acceptable salt thereof.

It is well known in the art, and understood in the instant invention, that peptidyl therapeutic agents such as the instant oligopeptide-cytotoxic agent conjugates preferably have the terminal amino moiety of any oligopeptide substituent protected with a suitable protecting group, such as acetyl, benzoyl, pivaloyl and the like. Such protection of the terminal amino group reduces or eliminates the enzymatic degradation of such peptidyl therapeutic agents by the action of exogenous amino peptidases which are present in the blood plasma of warm blooded animals.

The oligopeptide-cytotoxic agent conjugates of the invention are administered to the patient in the form of a pharmaceutical composition which comprises a conjugate of Formula (I) and a pharmaceutically acceptable carrier, excipient or diluent therefor. As used, "pharmaceutically acceptable" refers to those agents which are useful in the treatment or diagnosis of a warm-blooded animal including, for example, a human, equine, procine, bovine, murine, canine, feline, or other mammal, as well as an avian or other warm-blooded animal. The preferred mode of administration is parenterally, particularly by the intravenous, intramuscular, subcutaneous, intraperitoneal, or intralymphatic route. Such formulations can be prepared using carriers, diluents or excipients familiar to one skilled in the art. In this regard, See, e.g. Remington's Pharmaceuticil Sciences, 16th ed., 1980, Mack Publishing Company, edited by Osol et al. Such compositions may include proteins, such as serum proteins, for example, human serum albumin, buffers or buffering substances such as phosphates, other salts, or electrolytes, and the like. Suitable diluents may include, for example, sterile water, isotonic saline, dilute aqueous dextrose, a polyhydric alcohol or mixtures of such alcohols, for example, glycerin, propylene glycol, polyethylene glycol and the like. The compositions may contain preservatives such as phenethyl alcohol, methyl and propyl parabens, thimerosal, and the like. If desired, the composition can include about 0.05 to about 0.20 percent by weight of an antioxidant such as sodium metabisulfite or sodium bisulfite.

For intravenous administration, the composition preferably will be prepared so that the amount administered to the patient will be from about 0.01 to about 1 g of the conjugate. Preferably, the amount administered will be in the range of about 0.2 g to about 1 g of the conjugate. The conjugates of the invention are effective over a wide dosage range depending on factors such as the disease state to be treated or the biological effect to be modified, the manner in which the conjugate is administered, the age, weight and condition of the patient as well as other factors to be determined by the treating physician. Thus, the amount administered to any given patient must be determined on an individual basis.

One skilled in the art will appreciate that although specific reagents and reaction conditions are outlined in the following examples, modification can be made which are meant to be encompassed by the spirit and scope of the invention. The following preparations and examples, therefore, are provided to further illustrate the invention, and are not limiting.

EXAMPLES

Example 1
Identification of the Semenogelin PSA Mediated Cleavage Site:

Liquefaction of the seminal gel parallels proteolytic fragmentation of semenogelin I [Lilja, H., Laurell, C. B., (1984) Scand. J. Clin. Lab. Inves. 44, 447–452]. It is believed that the proteolytic fragmentation of semenogelin is mainly due to the proteolytic activity of prostate-specific antigen [Lilja, H., (1985) J. Clin. Invest. 76, 1899–1903]. Utilizing the published sequence of semenogelin I [Lilja, H., Abrahamsson, P. A., Lundwall, A., (1989) J. of Biol. Chem. 264, 1894–1900] (FIG. 1) we designed polymerase chain reaction primers to clone the semenogelin cDNA from a commercially available prostatic cDNA library (Clone-tech, Palo Alto, Calif.). The purified semenogelin cDNA was placed into the bacterial expression vector pTAC [Linemeyer, D. L., Kelly, L. J., Minke, J. G., Gimenez-Gallego, G., DeSalvo, J. and Thomas, K. A., (1987) Bio/Technology 5, 960–965]. The semenogelin cDNA was designed so that a tubulin epitope was placed at the carboxyl end of semenogelin protein. The bacterially expressed semenogelin protein was purified on an anti-tubulin antibody column. The purified semenogelin I protein was mixed with commercially prepared prostate-specific antigen (PSA) (York Biologicals International, Stony Brook, N.Y.) in an 100 to 1 molar ratio (semenogelin I/PSA) in 12 mM Tris pH 8.0, 25 mM NaCl, 0.5 mM CaCl$_2$, and incubated for various times. The digest was fractionated by polyacrylamide gel electrophoresis and transferred by electrophoresis to ProBlott filter paper (Applied Biosystems, Inc., Foster City, Calif.) in CAPS buffer [Matsudaira, P., (1987) J. Biol. Chem. 252, 10035–10038]. The ProBlott filter paper was stained with coomassie blue to identify the novel PSA generated semenogelin I protein fragments. The novel fragments were cut out of the filter with a scalpel and submitted for sequence determination. After the proteolytic fragments were identified by variable time digestion, a 10 minute digestion reaction was performed. The affinity of PSA for the 5 potential cleavage sites in semenogelin I was determined to be as follows: site 349/350>site 375/376>site 289/290=site 315/316>site 159/160. The relative affinities were derived from the comassie blue staining intensity of each PSA generated peptide fragment. These intensities had approximate ratios of 3:1:0.6:0.3.

Example 2
Preparation of Oligopeptides which Comprise the PSA Mediated Cleavage Site:

Oligopeptides were prepared by solid-phase synthesis, using a double coupling protocol for the introduction of amino acids on the Applied Biosystems model 430A automated peptide synthesizer. Deprotection and removal of the oligopeptide from the resin support were achieved by treatment with liquid hydrofluoric acid. The oligopeptides were purified by preparative high pressure liquid chromatography on reverse phase C18 silica columns using an aqueous 0.1% trifluoroacetic acid/acetonitrile gradient. Identity and homogeneity of the oligopeptides were confirmed by amino acid composition analysis, high pressure liquid chromatography, and fast atom bombardment mass spectral analysis. The oligopeptides that were prepared by this method are shown in FIG. 2.

Example 3
Assessment of the Recognition of Oligopeptides by Free PSA

The oligopeptides prepared as described in Example 2 were individually dissolved in PSA digestion buffer (12 mM tris(hydroxymethyl)-aminomethane pH8.0, 25 mM NaCl, 0.5 mM CaCl$_2$) and the solution added to PSA at a molar ration of 100 to 1. The reaction is quenched after various reaction times by the addition of trifluoroacetic acid (TFA) to a final 1% (volume/volume). The quenched reaction was analyzed by HPLC on a reversed-phase C18 column using an aqueous 0.1% TFA/acetonitrile gradient. The results of the assessment are shown in FIG. 2. Other oligopeptides prepared as described in Example 2 were tested in the same assay wherein the reaction was quenched at 4 hours. Those results of the assessment are shown in FIG. 3. The removal of an asparagine residue from the amino terminus of the oligopeptide results in a significant loss of PSA mediated peptide hydrolysis, while the presence of a glutamic acid residue at the carboxyl end of the peptide appears not to be essential to recognition by PSA.

Example 4
Preparation of Non-cleavable Oligopeptide-Doxorubicin Conjugates:

The derivatives of doxorubicin shown in Table 2 were prepared using the following general reaction: To a mixture of doxorubicin (Sigma) and the corresponding peptide (prepared by solid phase synthesis or commercially available (Sigma)) in DMSO was added HBTU and HOBT along with diisopropylethylamine and the reaction mixture was stirred overnight. The crude reaction mixture was purified directly by preparative HPLC on a reversed-phase C-18 column using a 0.1% trifluoroacetic acid (TFA) in acetonitrile/0.1% TFA in water gradient.

TABLE 2

(SEQ. ID. NO.: 12)

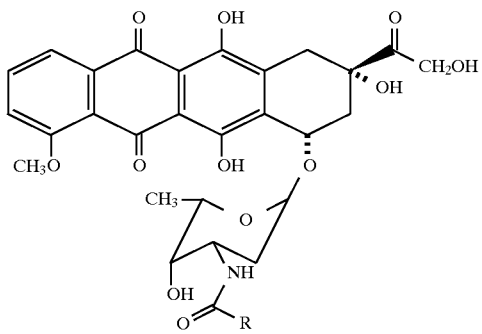

| Compound | R | MS (parent ion) |
|---|---|---|
| 12a | H—Ala— | 615 |
| 12b | N—Ac—Ala— | 657 |
| 12c | N—Ac—Ala—Ala—Ala— | 799.5 |
| 12d | N—Ac—Ala—Gly—Pro—Thr—Gly—Ala—Ser—Ala— | 1199 |

Example 5
In vitro Assay of Cytotoxicity of Peptidyl Derivatives of Doxorubicin:

The cytotoxicities of the non-cleaveable oligopeptide-doxorubicin conjugates, prepared as described in Example 4, against a line of cells which is known to be killed by unmodified doxorubicin were assessed with an Alamar Blue assay. Specifically, cell cultures of LNCaP prostate tumor cells, which are a human metastatic prostate adenocarcinoma isolated from a needle biopsy of a lymph node (LNCaP.FGC: American Type Culture Collection, ATCC CRL 1740), or DuPRO cells in 96 well plates were diluted with medium containing various concentrations of a given conjugate (final plate well volume of 200 μl). The cells were incubated for 3 days at 37° C. and then 20 μl of Alamar Blue was added to the assay well. The cells were further incubated and the assay plates were read on a EL-310 ELISA reader at the dual wavelengths of 570 and 600 nm at 4 and 7 hours after addition of Alamar Blue. Relative percentage viability at the various concentration of conjugate tested was then calculated versus control (no conjugate) cultures. Cytotoxicities of unmodified doxorubicin and unmodified oligopeptide were also assessed. FIG. 3 shows the cytotoxicity data for a representative compound (Compound 12d).

Example 6
Assessment of Enzymatically Active PSA from LNCaP Cells

Enzymatic activity was demonstrated by incubating LNCaP serum free media (concentrated approximately 200 fold) with recombinant Sememogelin I protein. Approximately 0.5 μg of immunologically reactive PSA in concentrated conditioned media [determined by HYBRIDTECH (Tandem E) elisa] was mixed with approximately 3 μg of recombinant Semenogelin I and incubated for 4 hours at 37° C. At the end of the incubation, the digest mixture was analyzed by Western blot procedures The results show that purified PSA from semen and PSA from LNCaP conditioned media generate identical proteolytic maps of the recombinant Semenogelin I protein. Thus, LNCap cells produce enzymatically active PSA. LNCaP are tumorigenic in nude mice and produce detectable levels of circulating PSA.

Example 7
Preparation of Cleavable Oligopeptide-Doxorubicin Conjugates:

The derivatives of doxorubicin wherein an oligopeptide which is proteolytically cleaved by free PSA is covalently attached to the amine of the sugar moiety of the doxorubicin were prepared using the following general reaction: To a mixture of doxorubicin (Sigma) and the corresponding peptide (prepared by solid phase synthesis as described in Example 2) in DMSO was added HBTU and HOBT along with diisopropylethylamine and the reaction mixture stirred overnight. The crude reaction mixture was purified directly by preparative HPLC on a reversed-phase C-18 column using a 0.1% trifluoroacetic acid (TFA) in acetonitrile/0.1% TFA in water gradient. When reactive amine moieties were present on the peptide, such a functionality was typically protected as the fluorenylmethyloxycarbonyl adduct, which was removed by treatment with a secondary amine, such as piperidine and the like, subsequent to conjugation with doxirubicin. The instant conjugates have a structure of the general formula

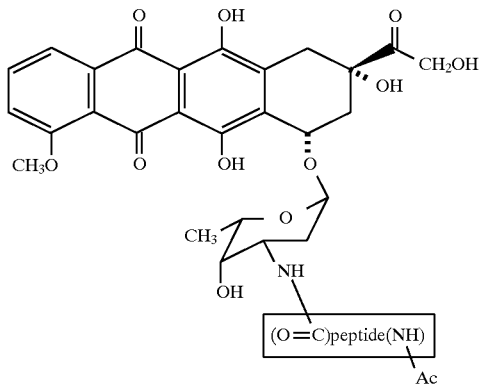

and may be represented by the phrase "Ac-peptide-DOX (3')." Conjugates which were prepared by the above general method or by the synthetic route described in Example 8, but utilizing the appropriate starting amino acid residues which are readily available commercially or by synthetic techniques well known in the art, are listed in FIGS. 5, 5A and 7.

Example 8
Ac-Lys-Tyr-Gln-Ser-Ser-Ser-Leu-Dox•Acetate
Step A: Ac-Lys(Fmoc)-Gln-Ser(Bzl)-Ser(Bzl)-Ser(Bzl)-Leu-PAM Resin (1).

Starting with 0.5 mmol (0.67g) Boc-Leu-PAM resin, the protected peptide was synthesized on a 430A ABI peptide synthesizer. The protocol used a 4 fold excess (2 mmol) of each of the following protected amino acids: Boc-Ser (OBzl), Boc-Gln, Boc-Tyr(BrZ), Boc-Lys(Fmoc). Coupling was achieved using DCC and HOBT activation in methyl-2-pyrrolidinone. Acetic acid was used for the introduction of the N terminal acetyl group. Removal of the Boc group was performed using 50% TFA in methylene chloride and the TFA salt neutralized with diisopropylethylamine. At the completion of the synthesis, the peptide resin was dried to yield 1.3g of (1).

Step B: Ac-Lys(Fmoc)-Tyr-Gln-Ser-Ser-Ser-Leu-OH (2).

The protected peptide resin (1), 1.3 g, was treated with HF (20 ml) for 2 hrs at 0° C. in the presence of anisole (2 ml). After evaporation of the HF, the residue was washed with ether, filtered and extracted with DMF. The DMF filtrate (75 ml) was concentrated to dryness and triturated with $H_2O$. The insoluble product (2) was filtered and dried (0.46g).

Step C: Ac-Lys(Fmoc)-Tyr-Gln-Ser-Ser-Ser-Leu-Dox (3)

The above prepared intermediate (2), 0.46g, (0.43 mmol) was dissolved in DMF (15 ml) and doxorubicin hydrochloride, 125 mg (0.215 mmol), added followed by 60 µl of triethylarnine (0.430 mmol). The stirred solution was cooled (0° C.) and 92 µl of diphenylphosphoryl azide (0.43 mmol) added. After 5 minutes, an additional 92 µl of DPPA was added and the pH adjusted to 7.5 (pH paper) with TEA. After 1 hour, an additional 92 µl of DPPA was added., pH adjusted to 7.5, and the reaction stirred at 0°–5° C. overnight. After 18 hours, the reaction (found to be complete by analytical HPLC) was concentrated to an oil (3).

Step D: Ac-Lys-Gln-Tyr-Ser-Ser-Ser-Leu-Dox (4).

The above product (3) was dissolved in DMF (20 ml), cooled (0° C.) and 10 ml of piperidine added. The solution was concentrated to dryness and purified by preparative HPLC. Buffer A=15% acetic acid–$H_2O$; B=15% acetic acid–methanol. The crude product was dissolved in 300 ml of 10% B/90% A buffer, filtered and purified on a C-18 reverse phase HPLC radial compression column (Vaters, Delta-Pak 15 µm, 300 Å). A step gradient of 10% B to 60% B was used at a flow rate of 75 ml/min (uv=260 nm). Homogeneous product fractions were pooled, concentrated and freeze-dried from $H_2O$ to yield 125 mg of purified product (4).

Example 9
Deacetylvinblastinyl-Leu-Asn-Lys-Ala-Ser-Try-Gln-Ser-Ser-Ser-Leu-$NH_2$•Acetate (5) (SEQ.ID.NO. 184)
Step A: $NH_2$-Leu-Asn-Lys(Fmoc)-Ala-Ser-Tyr-Gln-Ser-Ser-Ser-Leu-Amide (6)

Starting with 0.5 mmol of p-methylbenzhydrylamine resin (MBHA), the protected peptide, $NH_2$-Leu-Asn-Lys (Fmoc)-Ala-Ser(OBzl)-Tyr(BrZ)-Gln-Ser(OBzl)-Ser (OBzl)-Ser(OBzl)-Leu-MBHA, intermediate was synthesized on a 430A ABI peptide synthesizer. The protocol used a 4 fold excess (2 mmol) of each of the following protected amino acids: Boc-Leu, Boc-Asn, Boc-Lys (Fmoc), Boc-Ala, Boc-Ser(OBzl), Boc-Tyr(BrZ), Boc-Gln. Coupling was achieved using DCC and HOBT activation in N-methyl-2-pyrrolidinone (NMP).

Removal of the Boc group was performed using 50% TFA in methylene chloride and the TFA salt neutralized with diisopropylethylamine. The dried protected peptide resin (1.80g) was treated with HF (20 ml) for 2 hrs at 0° C. in the presence of anisole (2 ml). After evaporation, the residue was extracted with DMF. The DMF filtrate (75 ml) was concentrated to dryness, dissolved in a 1:1 mixture of acetonitrile-$H_2O$ and freeze-dried to give 750 mg of crude product. A portion (200 mg) was purified by preparative HPLC on a C-18 reverse phase support (Waters, µ-Bondapak). Buffer A=15% acetic acid–$H_2O$; B=15% acetic acid–methanol. For the purification, the crude product was suspended in 400 ml of 10% B/90% A buffer, filtered and the filtrate loaded onto the column. A step gradient of 10% B to 55% B was used at a flow rate of 75 ml/min. Homogeneous product fractions were pooled, concentrated and freeze-dried from 1120 to yield (6).

Step B: Deacetylvinblastin Monohydrazide (7)

1 g of vinblastine sulfate was converted to the amine form by extraction in methylene chloride and saturated sodium bicarbonate. The methylene chloride layer was washed with $H_2O$, dried over anhydrous $MgSO_4$ and concentrated to dryness The vinblastine was then dissolved in anhydrous ethanol (20 ml) and anhydrous hydrazine added (20 ml). The solution was heated (60° C.) under an $N_2$ atmosphere for 17 hrs. The reaction was concentrated to an oil, dissolved in methylene chloride, extracted with $H_2O$ and dried over $MgSO_4$. After evaporation compound (7) was isolated. [Ref: K. S. P. Bhushana Rao et al., J. Med. Chem. (1985), 28:1079.]

Step C: Deacetylvinblastine Acid Azide (8).

Deacetylvinblastine monohydrazide (7) (48 mg, 0.0624 mmol) was dissolved in DMF (3 ml), cooled (−15° C.) and acidified to ~2.5 (pH paper) with HCl/dioxane. Isoamylnitrite (10 µl) was added followed by an additional 10 µl after 10 min. HPLC analysis indicated complete conversion of the hydrazide to azide after 5 min. The azide was maintained in solution at −15° C. until ready for use.

Step D: Deacetylvinblastinyl-Leu-Asn-Lys-Ala-Ser-Try-Gln-Ser-Ser-Ser-Leu-$NH_2$•Acetate (5)

The oligopeptide product (6) from Step A, 32 mg (0.0225 mmol), was dissolved in DMF (1 ml) and cooled (−15° C.). To this solution was added a 1.5 ml DMF solution (0.031 mmol of desacetylvinblastine acid azide (8). The pH was adjusted to ~7.5 (pH paper) with triethylamine and the reaction stirred at −5° C. (2 hr), and 0° C. for 18 hr. To the reaction was added $H_2O$ (2 ml) and the solution evaporated to dryness. The intermediate was dissolved in DMF (4 ml), cooled (0° C.) and 2 ml of piperidine added. The solution was concentrated to dryness and purified by preparative HPLC as described in Step A. The homogeneous fractions were pooled, concentrated and freeze-dried from $H_2O$ to yield (5).

Example 10
Deacetylvinblastinyl-Leu-Asn-Lys-Ala-Ser-Try-Gln-Ser-Ser-Ser-Leu-Dox•Acetate (10).
Step A: Deacetylvinblastinyl-Leu-Asn-Lys(Fmoc)-Ala-Ser-Try-Gln-Ser-Ser-Ser-Leu-Dox•Acetate (9)

The oligopeptide product (6) prepared as described in Example 9, Step A, (166 mg, 0.125 mmol), was dissolved in DMSO (3 ml) and cooled to −15° C. To this solution was added a DMF solution (0.125 mmol) of desacetylvinblastine acid azide (8) prepared as described in Example 9, Step C. The pH was adjusted to ~7.5 (pH paper) with triethylamine and the reaction stirred at −15° C. for 90 mins.

After stirring 18 hours at 0°–5° C., the reaction was concentrated to dryness and the crude residue was dissolved in DMF (10 ml) and filtered. Doxorubicin hydrochloride, 62 mg (0.106 mmol), was added to the filtrate followed by 30 μl of triethylamine. The stirred solution was cooled (0° C.) and 27 μl of diphenylphosphoryl azide (DPPA, 0.134 mmol) added. After 5 minutes, an additional 27 μl of DPPA was added and the pH adjusted to ~7.5 (pH paper) with TEA. After 1 hour, an additional 27 μl of DPPA was added, pH adjusted to ~7.5, and the reaction stirred at 0°–5° C. overnight. After 18 hours, the reaction (found to be complete by analytical HPLC) was concentrated to an oil (9).

Step B: Deacetylvinblastinyl-Leu-Asn-Lys-Ala-Ser-Try-Gln-Ser-Ser-Ser-Leu-Dox•Acetate (10).

The above intermediate product (9) was dissolved in DMF (20 ml), cooled (0° C.) and 10 ml of piperidine added. The solution was concentrated to dryness and purified by preparative HPLC. Buffer A=15% acetic acid–$H_2O$; B=15% acetic acid–methanol. The crude product was dissolved in 300 ml of 10% B/90% A buffer, filtered and purified on a C-18 reverse phase HPLC radial compression column (Waters, μ-Bondapak). A step gradient of 10% B to 60% B was used at a flow rate of 75 ml/min (uv=260 nm). Semi-pure product was further purified on C-18 (Waters, Prep Pak) using Buffer A=0.13M pH 3.0 triethylammonium phosphate and Buffer B=acetonitrile. A step gradient of 10% B to 40% B was used at a flow rate of 75 ml/min. (uv=214 nm). Pure produce fractions were pooled, diluted with H2O and desalted by applying the product onto the same column and eluting the produce as the actetate salt with 90% acetonitrile/ 10% $H_2O$ (1% acetic acid). The product fractions were concentrated and freeze dried from $H_2O$ to yield the purified product (10).

Example 11
Ac-Lys-Tyr-Gln-Ser-Ser-Ser-Nle-NH-$(CH_2)_3$NH-deacetylvinblastine amide (14)

Step A: Deacetylvinblastine-3-aminopropyl amide (11)

To a cooled (–15° C.) a DMF solution (3 ml, 0.0624 mmol) of deacetylvinblastine acid azide (synthesis described in Example 9, Step C) was added 120 μl of 1,3-diaminopropane in DMF (2 ml). The reaction was stirred at –10° C. for 1 hr, filtered and concentrated to dryness to yield (11).

Step B: Deacetylvinblastine-3-aminopropylamidenorleucine amide (12)

To a DMF solution (1 ml) of Boc-Nle (22 mg, 0.095 mmol) was added 318 μl of a 1M solution of HOBT (in NMP) followed by 280 μl of a 1M solution of DCC (in NMP). After 30 min., intermediate (11) (0.0624 mmol) was added in a 3.5 ml DMF. The pH of the reaction was adjusted ~7.5 with diisopropylethylamine. After stirring for 18 hrs the reaction was concentrated to an oil and the Boc protecting group removed by treating the oil with a 1:1 solution of TFA: $CH_2Cl_2$ (20 ml). After 5 min. the reaction was concentrated to dryness. Purification was achieved by preparative HPLC on a C-18 reverse phase support (Waters, Delta Pak). Buffer A=0.1% TFA–$H_2O$; B=0.1% TFA–$CH_3CN$. The crude product was loaded in 100% A buffer (100 ml) and a step gradient of 100% A to 30% A was used at a flow rate of 75 ml/min. Homogeneous product fractions were pooled and freeze-dried to yield (12).

Step C: Ac-Lys(Fmoc)-Tyr-Gln-Ser-Ser-Ser-Nle-OH (13)

The above intermediate was prepared as described in Example 9, Step A for the preparation of Ac-Lys(Fmoc)-Tyr-Gln-Ser-Ser-Ser-Leu-OH.

Step D: Ac-Lys-Tyr-Gln-Ser-Ser-Ser-Nle-NH-$(CH_2)_3$ NH-deacetylvinblastine amide (14)

The oligopeptide product (13), (70 mg, 0.065 mmol) in DMF (1 ml) was combined with (41 mg, 0.05 mmol) of (12) in DMF (4 ml). The solution was cooled (0° C.) and 17 μl of diphenylphosphoryl azide (0.08 mmol) added. After 5 min. an additional 17 μl of DPPA was added and the pH adjusted to ~7.5 (pH paper) with triethylamine. After 2 hr. additional (13), 35 mg, was added in DMF (0.5 ml) and 17 μl of DPPA. The pH was maintained at ~7.5 with TEA and after 3 hr. an additional 35 mg of (13) was added in DMF (0.5 ml). The reaction was stirred at 0°–5° C. After 18 hrs, the reaction was concentrated to dryness, redissolved in DMF (9 ml), cooled (0° C.) and 3 ml of piperidine added. The solution was concentrated to dryness and purified by preparative HPLC. Buffer A=0.1% TFA-$H_2O$; B=0.1% TFA-$CH_3CN$. The crude product was dissolved in 30% acetic acid-$H_2O$ (100 ml) and purified on a C-18 reverse phase HPLC radial compression column (Waters, Delta Pak). A step gradient of 100% A to 70% A was used at a flow rate of 75 ml/min. Semi-pure product fractions were pooled and freeze-dried. Purification to homogeneity was achieved by repurification on a C-4 support (Waters, Delta Pak) as described above. Product fraction were pooled and freeze dried to yield pure (14).

Example 12
Assessment of the Recognition of Oligopeptide-Doxorubicin Conjugates by Free PSA:

The conjugates prepared as described in Examples 7–9 were individually dissolved in PSA digestion buffer (12 mM tris(hydroxymethyl)-aminomethane pH8.0, 25 mM NaCl, 0.5 mM $CaCl_2$) and the solution added to PSA at a molar ration of 100 to 1. The reaction is quenched after various reaction times by the addition of trifluoroacetic acid (TFA) to a final 1% (volume/volume). The quenched reaction was analyzed by HPLC on a reversed-phase C18 column using an aqueous 0.1%TFA/acetonitrile gradient. The results of the assessment are shown in FIG. 5.

Example 13
Assessment of the Cleavage of Oligolpeptide-Doxorubicin Conjugates in Cell Conditioned Media Cell conditioned serum-free α-MEM media (phenol red minus) was collected 3 days after the addition of the media to either LNCaP or Dupro (prepared as described in J. Urology, 146:915–919 (1991)) cell lines. The media was concentrated 20 fold using an Amicon® Centriprep™ concentrator with a 10,000 molecular weight cutoff. The LNCaP conditioned media contained free PSA protein at, on average, approximately 100 ng/mL concentration as determined by the Tandem®-E PSA immunodetection kit (Hybritech®). There was no detectable free PSA in the Dupro cell conditioned media.

100 μL portions of concentrated conditioned media was mixed with 35 μg of a oligopeptide-doxorubicin conjugate prepared as described in Example 7 and the mixture was incubated at 37° C. for 0, 4 and 24 hour time points. The reactions were stopped by the addition of $ZnCl_2$ (to a 0.01M final concentration and analyzed by HPLC on a reversed-phase C18 column using an aqueous 0.1% TFA/acetonitrile gradient to determine the percentage of peptide-cytotoxic agent conjugate that had been digested. The results of the assessment are shown in FIG. 6.

Example 14
In vitro Assay of Cytotoxicity of Peptidyl Derivatives of Doxorubicin:

The cytotoxicities of the cleaveable oligopeptide-doxorubicin conjugates, prepared as described in Example 7, against a line of cells which is known to be killed by unmodified doxorubicin was assessed with an Alamar Blue assay as described in Example 5. Specifically, cell cultures of LNCap prostate tumor cells or DuPRO cells in 96 well plates was diluted with medium containing various concentrations of a given conjugate (final plate well volume of 200 μl). The cells were incubated for 3 days at 37° C., 20 μl of Alamar Blue is added to the assay well. The cells were further incubated and the assay plates were read on a EL-310 ELISA reader at the dual wavelengths of 570 and 600 nm at 4 and 7 hours after addition of Alamar Blue. Relative percentage viability at the various concentration of conjugate tested was then calculated versus control (no conjugate) cultures. Cytotoxicities of the conjugates were also compared to the cytotoxicity of unmodified doxorubicin and unmodified oligopeptide assessed in the same assay. Results of this assay are shown in FIG. 7.

Example 15
In vivo Efficacy of Peptidyl-Cytotoxic Agent Conjugates

LNCaP.FGC or DuPRO-1 cells are trypsinized, resuspended in the growth medium and centifuged for 6 mins. at 200×g. The cells are resuspended in serum-free α-MEM and counted. The appropriate volume of this solution containing the desired number of cells is then transferred to a conical centrifuge tube, centrifuged as before and resuspended in the appropriate volume of a cold 1:1 mixture of α-MEM-Matrigel. The suspension is kept on ice until the animals are inoculated.

Harlan Sprague Dawley male nude mice (10–12 weeks old) are restrained without anesthesia and are inoculated with 0.5 mL of cell suspension on the left flank by subcutaneous injection using a 22G needle. Mice are either given approximately $5 \times 10^5$ DuPRO cells or $1.5 \times 10^7$ LNCaP.FGC cells.

Following inoculation with the tumor cells the mice are treated under one of two protocols:

Protocol A:

One day after cell inoculation the animals are dosed with a 0.1–0.5 mL volume of test conjugate, doxorubicin or vehicle control (sterile water). Dosages of the conjugate and doxorubicin are initially the maximum non-lethal amount, but may be subsequently titrated lower. Identical doses are administered at 24 hour intervals for 5 days. After 10 days, blood samples are removed from the mice and the serum level of PSA is determined. Similar serum PSA levels are determined at 5–10 day intervals. At the end of 5.5 weeks the mice are sacrificed and weights of any tumors present are measured and serum PSA again determined. The animals weights are determined at the beginning and end of the assay.

Protocol B:

Ten days after cell inoculation, blood samples are removed from the animals and serum levels of PSA are determined. Animals are then grouped according to their PSA serurm levels. At 14–15 days after cell inoculation, the animals are dosed with a 0.1–0.5 mL volume of test conjugate, doxorubicin or vehicle control (sterile water). Dosages of the conjugate and doxorubicin are initially the maximum non-lethal amount, but may be subsequently titrated lower. Identical doses are administered at 24 hour intervals for 5 days. Serum PSA levels are determined at 5–10 day intervals. At the end of 5.5 weeks the mice are sacrificed, weights of any tumors present are measured and serum PSA again determined. The animals' weights are determined at the beginning and end of the assay.

What is claimed is:

1. An oligopeptide which is selected from
AlaAsnLysIleSerTyrGln|SerSerSerThrGlu-amide (SEQ.ID.NO.: 11)
Ac-AlaAsnLysIleSerTyrGln|SerSerSerThrLeu (SEQ.ID.NO.: 70)
Ac-AlaAsnLysIleSerTyrGln|SerSerSerThrGlu-amide (SEQ.ID.NO.: 11)
Ac-AlaAsnLysIleSerTyrGln|SerSerSerThrLeu-amide (SEQ.ID.NO.: 70)
Ac-AlaAsnLysIleSerTyrGln|SerAlaSerThrGlu-amide (SEQ.ID.NO.: 73)
Ac-AlaAsnLysIleSerTyrGln|SerSerLysThrGlu-amide (SEQ.ID.NO.: 74)
Ac-AlaAsnLysIleSerTyrGln|SerSerThrGlu-amide (SEQ.ID.NO.: 75)
Ac-AlaAsnLysIleSerTyrGln|SerSerGluThrGlu-amide (SEQ.ID.NO.: 78)
Ac-AlaAsnLysIleSerTyrGln|SerAlaLysThrGlu-amide (SEQ.ID.NO.: 79)
Ac-AlaAsnLysIleSerTyrGln|SerThrGlu-amide (SEQ.ID.NO.: 81)
Ac-AlaAsnLysSerTyrGln|SerSerThrGlu-amide (SEQ.ID.NO.: 82)
Ac-AlaAsnLysAlaSerTyrGln|SerAlaSerThrGlu-amide (SEQ.ID.NO.: 84)
Ac-AlaAsnGluIleSerTyrGln|SerAlaSerThrGlu-amide (SEQ.ID.NO.: 85)
Ac-AsnLysIleSerTyrGln|SerSer-amide (SEQ.ID.NO.: 16)
Ac-LysIleSerTyrGln|SerSer-amide (SEQ.ID.NO.: 86)
Ac-SerTyrGln|SerSerThrGlu-amide (SEQ.ID.NO.: 87)
Ac-AlaSerTyrGln|SerSerThrGlu-amide (SEQ.ID.NO.: 89)
Ac-AlaAsnLysIleSerTyrTyr|SerSerSerThrGlu-amide (SEQ.ID.NO.: 92)
Ac-AlaAsnLysIleSerTyrTyr|SerAlaSerThrGlu-amide (SEQ.ID.NO.: 93)
Ac-AlaSerTyrGln|SerSerLeu-amide (SEQ.ID.NO.: 94)
Ac-AlaAsnSerTyrGln|SerSerSerThrGlu-amide (SEQ.ID.NO.: 95)
Ac-AlaSerTyrGln|SerSerSerThrGlu-amide (SEQ.ID.NO.: 96)
Ac-SerTyrGln|SerSerSerThrGlu-amide (SEQ.ID.NO.: 97)
Ac-AlaAsnLysAlaSerTyrGln|SerAlaSerCys-amide (SEQ.ID.NO.: 98)
Ac-hArg(Cha)Gln|SerNle-Acid (SEQ.ID.NO.: 147)
Ac-hArghTyrGln|SerSerNle-Acid (SEQ.ID.NO.: 148)
Ac-hArgh(Cha)Gln|SerSerNle-Acid (SEQ.ID.NO.: 149)
Ac-AlaAspLysAlaSerTyrGln|SerSer-Cha-NHNH$_2$ (SEQ.ID.NO.: 150)
Ac-hArgTyrGln|SerSerPro-Acid (SEQ.ID.NO.: 151)
Ac-hArgTyrGln|SerSerHis-Acid (SEQ.ID.NO.: 152)
Ac-hArgTyrGln|SerAsn-Acid (SEQ.ID.NO.: 153)
Ac-hArgTyrGln|SerSerNle-Acid (SEQ.ID.NO.: 154)
Ac-(Amf)TyrGln|SerSerSerNle-Acid (SEQ.ID.NO.: 155)
H$_2$NCO-hArgTyrGln|SerSerSerLeu-Acid (SEQ.ID.NO.: 156)
Ac-AlaAspLysAlaLysTyrGln|SerSer(Cha)-NHNH$_2$ (SEQ.ID.NO. 157)
Ac-(DPL)TyrGlnlSerSerSerNle-Acid (SEQ.ID.NO.: 158)
Ac-(imidazolyl)LysTyrGln|SerSerLeu-Acid (SEQ.ID.NO.: 159)
Ac-AlaAspLysAla(hArg)TyrGln|SerSerLeu-Acid (SEQ.ID.NO.: 160)
Ac-(p-NH2-Cha)TyrGlnISerSerSerNle-Acid (SEQ.ID.NO.: 161)
Ac(imidazolyl)LysTyrGln|SerSerSerNle-Acid (SEQ.ID.NO.: 162)
Ac-hArg(Cha)Gln|SerSerSerNle-Acid (SEQ.ID.NO.: 163)
Ac-hArgTyrGln|SerSerSerhArg-Acid (SEQ.ID.NO.: 164)
Ac-hArgTyrGln|SerSerSer(MeLeu) (SEQ.ID.NO.: 188)
Ac-hArgTyrGln|SerSerSer(Ethylester-Leu) (SEQ.ID.NO.: 156)
Ac-AlaAspLysAla(imidazoleLys)TyrGln|SerSerNle-Acid (SEQ.ID.NO.: 165)
Ac-hArg(3-Iodo-Tyr)Gln|SerSerSerNle-Acid (SEQ.ID.NO.: 166)
Ac-hArg(Me$_2$PO$_3$-Tyr)Gln|SerSerSerNle-Acid (SEQ.ID.NO.: 167)
Ac-hArgTyrGln|SerSerAsp-Acid (SEQ.ID.NO.: 168)
Ac-hArg(O-Me-Tyr)Gln|SerSerSerNle-Acid (SEQ.ID.NO.: 169)
Ac-AlaAspLysAlaLysTyrGln|SerSerNle-Acid (SEQ.ID.NO.: 170)
Ac-hArg(Cha)Gln|SerSerSer(ethylester-Leu) (SEQ.ID.NO.: 171)
Ac-(imidazolyl)Lys(Cha)Gln|SerSerSerNle-Acid (SEQ.ID.NO.: 172)
Ac-hArg(Cha)Gln|SerSerSer-Acid (SEQ.ID.NO.: 173)
Ac-hArg(Cha)Gln|SerSerNle-Acid (SEQ.ID.NO.: 174)
Ac-hArg(Cha)Gln|SerProNle-Acid (SEQ.ID.NO.: 175) or
Ac-hArg(m-fluoro-Tyr)Gln|SerSerSerNle-Acid (SEQ.ID.NO.: 176), or the pharmaceutically acceptable salt thereof.

2. The conjugate which is selected from:

Ac-hArgTyrGln-SerSerPro-dox(3') (SEQ.ID.NO.: 151)

Ac-hArgTyrGln-SerPro-dox(3') (SEQ. ID.NO.: 177)

Ac-hArgTyrGln-SerSerSerNle-dox(3') (SEQ.ID.NO.: 154)

Ac-AmfTyrGln-SerSerSerNle-dox(3') (SEQ.ID.NO.: 155)

H$_2$NCO-hArgTyrGln-SerSerSerLeu-dox(3') (SEQ.ID.NO.: 156)

Ac-LysTyrGln-SerSerNle-dox(3') (SEQ.ID.NO.: 146)

Ac-LysTyrGln-SerLysNle-dox(3') (SEQ.ID.NO.: 178)

Ac(cis-p-NH$_2$Cha)TyrGlnSerSerNledox(3') (SEQ.ID.NO.: 161)

Ac-AlaAspLysAla(hArg)TyrGln-SerSerLeu-dox(3') (SEQ.ID.NO.: 160)

Ac-hArgTyrGln-SerAsn-dox(3') (SEQ.ID.NO.: 153)

Ac-hArgTyrGln-SerSerHis-dox(3') (SEQ.ID.NO.: 152)

Ac-(imidazolyl)LysTyrGln-SerSerLeuL-dox(3') (SEQ.ID.NO.: 159)

Ac-(imidazolyl)LysTyrGlnSerSerSerNle-dox(3') (SEQ.ID.NO.: 162)

Ac-hArg(Cha)Gln-SerSerSerNle-dox(3') (SEQ.ID.NO.: 163)

Ac-hArg(Me$_2$PO$_3$Tyr)Gln-SerSerSerNle-dox(3') (SEQ.ID.NO.: 167)

Ac-hArgTyrGln-SerSerSerhArg-dox(3') (SEQ.ID.NO.: 164)

Ac-hArg(3-Iodo-Tyr)Gln-SerSerSerNle-dox(3') (SEQ.ID.NO.: 166)

Ac-hArg(O-Me-Tyr)Gln-SerSerSerNle-dox(3') (SEQ.ID.NO.: 169)

Ac-hArg(p-NH$_2$-Phe)Gln-SerSerSerNle-dox(3') (SEQ.ID.NO.: 179)

Ac-hArg(Cha)Gln-SerSerNle-dox(3') (SEQ.ID.NO.: 174)

Ac-hArg(Cha)Gln-SerProNle-dox(3') (SEQ.ID.NO.: 175)

Ac(imidazolyl)Lys(Cha)GlnSerSerSerNle-dox(3') (SEQ.ID.NO.: 172)

Ac-hArg(7-HO-TIC)Gln-SerSerSerNle-dox(3') (SEQ.ID.NO.: 180)

Ac-hArg(3-Fluoro)TyrGlnSerSerSerNle-dox(3') (SEQ.ID.NO.: 176)

Ac-(ornithine)TyrGln-SerSerSerNle-dox(3') (SEQ.ID.NO.: 181)

Ac-LysAlaAlaSerSerSerLeu-dox(3') (SEQ.ID.NO.: 183)

Ac-hArgh(Cha)Gln-SerSerNle-dox(3') (SEQ.ID.NO.: 149)

Ac-AlaArgLysAlaSerTyrGln-SerLeu-dox(3') (SEQ.ID.NO.: 193) and

Ac-(Orn)TyrGln-SerSerSerLeu-dox(3') (SEQ.ID.NO.: 194)

or the pharmaceutically acceptable salt thereof.

3. A conjugate of the formula II:

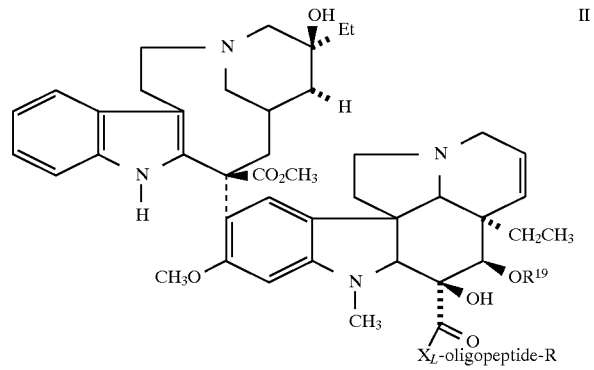

wherein:
oligopeptide is an oligopeptide which is specifically recognized by the free prostate specific antigen (PSA) and is capable of being proteolytically cleaved by the enzymatic activity of the free prostate specific antigen, provided that the oligopeptide does not comprise semenogelin I or semenogelin II;

XL is absent or is an amino acid selected from:
 a) phenylalanine,
 b) leucine,
 c) valine,
 d) isoleucine,
 e) (2-naphthyl)alanine,
 f) cyclohexylalanine,
 g) diphenylalanine,
 h) norvaline, and
 j) norleucine; or XL is —NH—(CH$_2$)$_n$—NH—

R is hydrogen or —(C=O)R$^1$;

R$^1$ is C$_1$–C$_6$-alkyl or aryl;

R$^{19}$ is hydrogen or acetyl; and n is 1, 2, 3, 4 or 5, or the pharmaceutically acceptable salt thereof.

4. The conjugate according to claim 3 of the formula

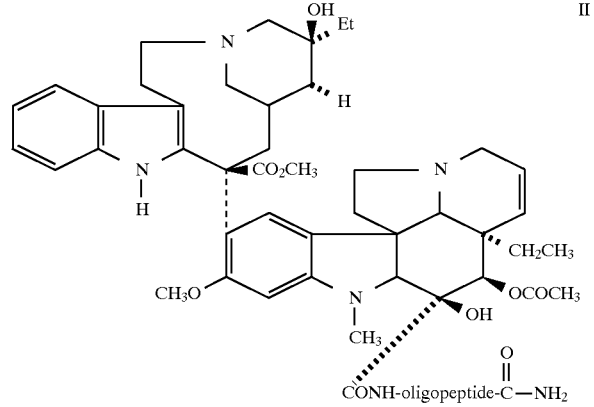

wherein
oligopeptide is an oligopeptide which is specifically recognized by the free prostate specific antigen (PSA) and is capable of being proteolytically cleaved by the enzymatic activity of the free prostate specific antigen,
or the pharmaceutically acceptable salt thereof.

5. The conjugate according to claim 3 which is selected from:

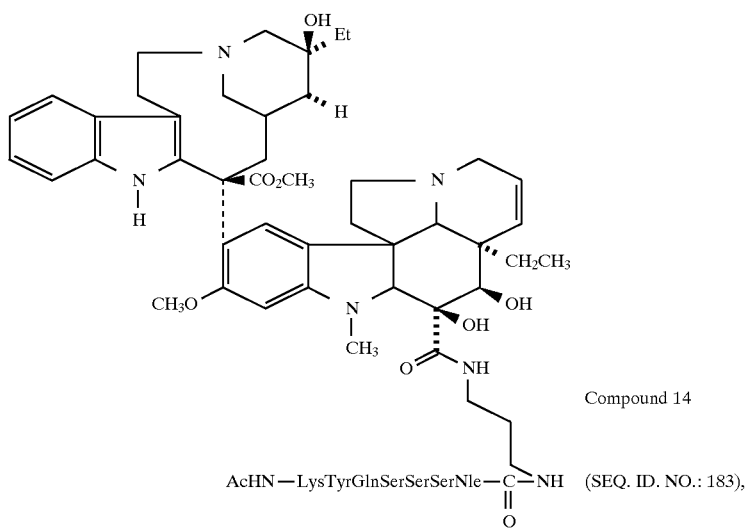

Compound 14

AcHN—LysTyrGlnSerSerSerNle—C(=O)—NH   (SEQ. ID. NO.: 183), and

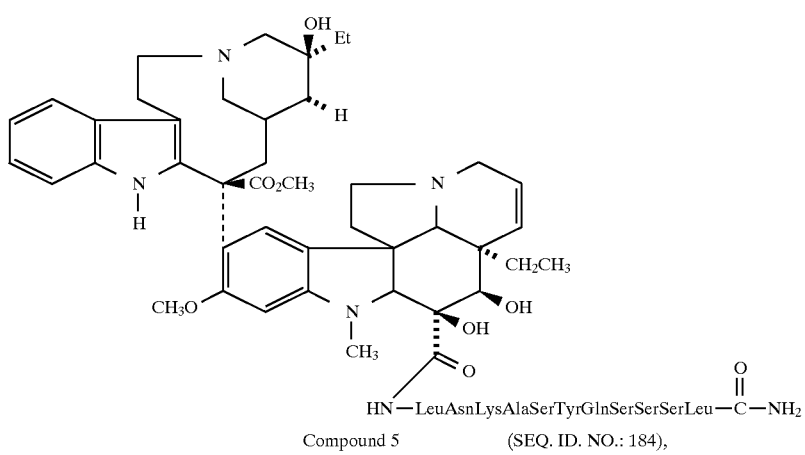

Compound 5   (SEQ. ID. NO.: 184), or the pharmaceutically acceptable salt thereof.

6. A conjugate which is useful for the treatment of prostate cancer which comprises two cytotoxic agents attached to a oligopeptide, wherein the oligopeptide comprises a sequence of amino acids that is recognized and selectively proteolytically cleaved by free prostate specific antigen and provided that the oligopeptide does not comprise semenogelin I or semenogelin II, wherein the means of attachment is a covalent bond or a chemical linker, or the pharmaceutically acceptable salt thereof.

7. The conjugate according to claim 6 which is

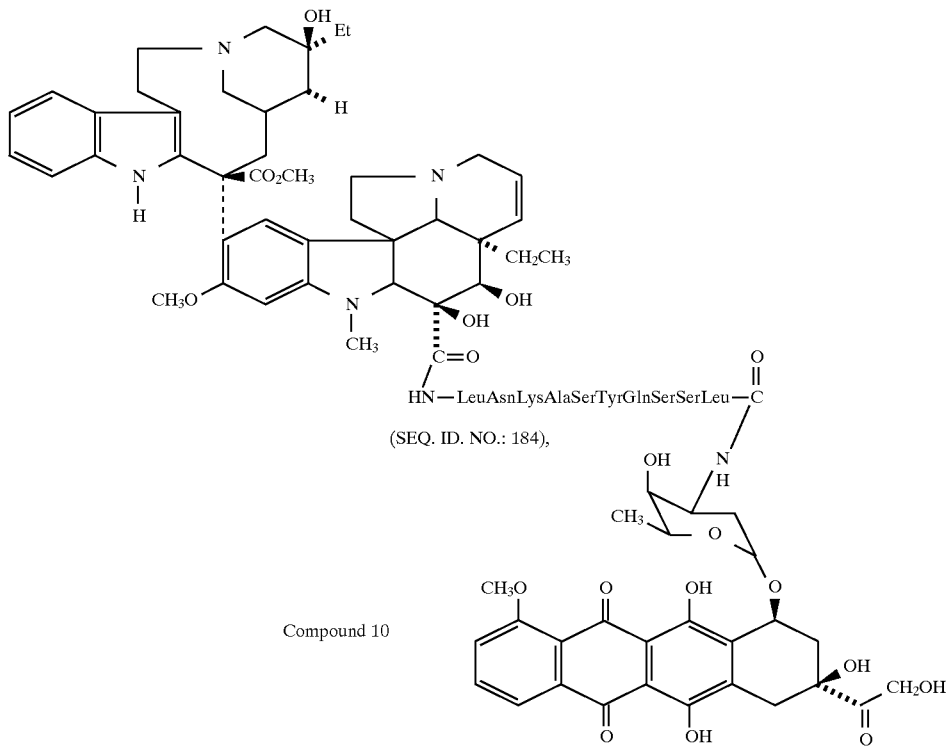

(SEQ. ID. NO.: 184),

Compound 10 or the pharmaceutically acceptable salt thereof.

8. An oligopeptide that comprises a sequence of amino acids that is recognized and selectively proteolytically cleaved by free prostate specific antigen, wherein the sequence of amino acids is
 a) AsnLysIleSerTyrTyr|Ser (SEQ.ID.NO.: 127),
 b) AsnLysAlaSerTyrGln|Ser (SEQ.ID.NO.: 128),
 c) SerTyrGln|SerSer (SEQ.ID.NO.: 129);
 d) LysTyrGln|SerSer (SEQ.ID.NO.: 140);
 e) hArgTyrGln|SerSer (SEQ.ID.NO.: 141);
 f) hArgChaGln|SerSer (SEQ.ID.NO.: 185); and
 g) TyrGln|SerSer (SEQ.ID.NO.: 186);
wherein hArg is homoarginine, Cha is cyclohexylalanine and Xaa is any natural amino acid,
 provided that the oligopeptide does not comprise semenogelin I or semenogelin II;
or the pharmaceutically acceptable salt thereof.

9. The oligopeptide according to claim 8 wherein the sequence of amino acids is
 a) AsnLysIleSerTyrGln|SerAla (SEQ.ID.NO.: 130),
 b) AlaAsnLysIleSerTyrTyr|Ser (SEQ.ID.NO.: 131),
 c) AlaAsnLysAlaSerTyrGln|Ser (SEQ.ID.NO.: 132),
 d) SerTyrGln|SerSerThr (SEQ.ID.NO.: 133),
 e) SerTyrGln|SerSerSer (SEQ.ID.NO.: 134),
 f) LysTyrGln|SerSerSer (SEQ.ID.NO.: 142),
 g) hArgTyrGln|SerSerSer (SEQ.ID.NO.: 143), or
 h) SerTyrGln|SerSerLeu (SEQ.ID.NO.: 135),
or the pharmaceutically acceptable salt thereof.

10. The oligopeptide according to claim 8 wherein the amino acid sequence is
 a) AlaAsnLysIleSerTyrGln|SerAla (SEQ.ID.NO.: 136),
 b) AlaAsnLysIleSerTyrTyr|SerSer (SEQ.ID.NO.: 137),
 c) AlaAsnLysIleSerTyrTyr|SerAla (SEQ.ID.NO.: 138),
 d) AlaAsnLysAlaSerTyrGln|SerAla (SEQ.ID.NO.: 139), or
 e) AlaSerTyrGln|SerSerLeu (SEQ.ID.NO.: 94),
or the pharmaceutically acceptable salt thereof.

11. A pharmaceutically acceptable salt of a conjugate which is useful for the treatment of prostate cancer and which comprises a cytotoxic agent attached to a oligopeptide, wherein the oligopeptide comprises a sequence of amino acids that is recognized and selectively proteolytically cleaved by free prostate specific antigen and provided that the oligopeptide does not comprise semenogelin I or semenogelin II, wherein the means of attachment is a covalent bond or a chemical linker.

12. The pharmaceutically acceptable salt of a conjugate according to claim 11 wherein the cytotoxic agent is a member of a class of cytotoxic agents selected from the following classes:
 a) anthracycline family of drugs,
 b) the vinca alkaloid drugs,
 c) the mitomycins,
 d) the bleomycins,
 e) the cytotoxic nucleosides,
 f) the pteridine family of drugs,
 g) diynenes,
 h) estramustine,
 i) cyclophosphamide, and
 h) the podophyllotoxins.

13. The pharmaceutically acceptable salt of a conjugate according to claim 11 wherein the cytotoxic agent is selected from the following cytotoxic agents:
 a) doxorubicin,
 b) carminomycin,
 c) daunorubicin, d) aminopterin,
e) methotrexate,
f) methopterin,
g) dichloro-methotrexate,
h) mitomycin C,
i) porfiromycin,
j) 5-fluorouracil,
k) 6-mercaptopurine,
l) cytosine arabinoside,
m) podophyllotoxin,
n) etoposide,
o) etoposide phosphate,
p) melehalan,
q) vinblastine,
r) vincristine,
s) leurosidine,
t) vindesine,
u) estramustine,
v) cisplatin,
w) cyclophosphamide, and
x) leurosine.

14. The pharmaceutically acceptable salt of a conjugate according to claim 11 wherein the cytotoxic agent is selected from doxorubicin and vinblastine or a cytotoxic derivative thereof.

15. The pharmaceutically acceptable salt of a conjugate according to claim 11 herein the cytotoxic agent is doxorubicin or a cytotoxic derivative thereof.

16. The pharmaceutically acceptable salt of a conjugate according to claim 15 wherein the conjugate is a compound of the formula I:

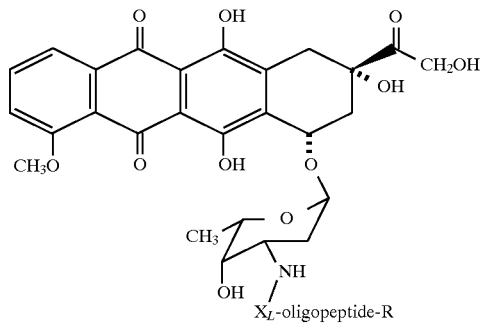

wherein:
oligopeptide is an oligopeptide which is specifically recognized by the free prostate specific antigen (PSA) and is capable of being proteolytically cleaved by the enzymatic activity of the free prostate specific antigen;
XL is absent or is an amino acid selected from:
a) phenylalanine,
b) leucine,
c) valine,
d) isoleucine,
e) (2-naphthyl)alanine,
f) cyclohexylalanine,
g) diphenylalanine,
h) norvaline, and
j) norleucine;
R is hydrogen or —(C=O)R¹; and
R¹ is $C_1$–$C_6$-alkyl or aryl.

17. The pharmaceutically acceptable salt of a conjugate according to claim 16 wherein:
oligopeptide is an oligomer that comprises an amino acid sequence selected from:
a) AsnLysIleSerTyrGln|Ser (SEQ.ID.NO.: 13),
b) LysIleSerTyrGln|Ser (SEQ.ID.NO.: 14),
c) GlyGluAsnGlyValGlnLysAspValSerGlnXaaSerNle Tyr|SerGlnThrGlu (SEQ.ID.NO.: 15),
d) GlyLysGlyIleSerSerGlnTyr|SerAsnThrGluGluArg Leu (SEQ.ID.NO.: 2),
e) AsnLysIleSerTyrTyr|Ser (SEQ.ID.NO.: 127),
f) AsnLysAlaSerTyrGln|Ser (SEQ.ID.NO.: 128),
g) SerTyrGln|SerSer (SEQ.ID.NO.: 129),
h) LysTyrGln|SerSer (SEQ.ID.NO.: 140);
i) hArgTyrGln|SerSer (SEQ.ID.NO.: 141);
j) hArgChaGln|SerSer (SEQ.ID.NO.: 185); and
k) TyrGln|SerSer (SEQ.ID.NO.: 136);
wherein hArg is homoarginine and Xaa is any natural amino acid;
XL is absent or is an amino acid selected from:
a) leucine,
b) isoleucine,
c) norleucine and
d) valine; and
R is acetyl, pivaloyl or benzoyl.

18. The pharmaceutically acceptable salt of a conjugate according to claim 16 which is selected from:

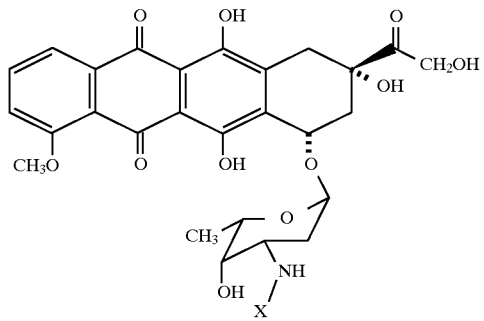

wherein X is:

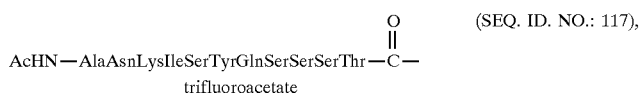

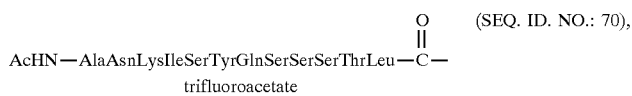

AcHN—AlaAsnLysAlaSerTyrGlnSerAlaSerThrLeu—C(=O)— acetate    (SEQ. ID. NO.: 118), AcHN—AlaAsnLysAlaSerTyrGlnSerAlaSerLeu—C(=O)— acetate    (SEQ. ID. NO.: 119), AcHN—AlaAsnLysAlaSerTyrGlnSerSerSerLeu—C(=O)— acetate    (SEQ. ID. NO.: 120), AcHN—AlaAsnLysAlaSerTyrGlnSerSerLeu—C(=O)— acetate    (SEQ. ID. NO.: 121), AcHN—hArgTyrGlnSerSerSerLeu—C(=O)— acetate    (SEQ. ID. NO.: 145), AcHN—LysTyrGlnSerSerSerLeu—C(=O)— acetate    (SEQ. ID. NO.: 124), or AcHN—LysTyrGlnSerSerNle—C(=O)— acetate    (SEQ. ID. NO.: 146).

* * * * *

UNITED STATES PATENT AND TRADEMARK OFFICE
CERTIFICATE OF CORRECTION

PATENT NO. : 5,866,679

DATED : February 2, 1999

INVENTOR(S) : Deborah DeFeo-Jones, Victor M. Garsky, Dong-Mei Feng, Raymond E. Jones and Allen I. Oliff It is certified that error appears in the above-identified patent and that said Letters Patent is hereby corrected as shown below:

On the cover page, Section [54], the Title should read:

-- NOVEL PEPTIDES --.

In claim 1, column 163, line 31 should read:

-- Ac-AlaAsnLysIleSerTyrGlnlSerSerGlnThrGlu-amide --.

In claim 1, column 164, line 33 should read:

-- Ac-(p-NH2-Cha)TryGlnlSerSerSerNle-Acid --.

In claim 2, column 165, line 1 should read:

-- 2. A conjugate which is selected from: --.

In claim 2, column 165, line 24 should read:

-- Ac-(imidazolyl)LysTyrGln-SerSerLeu-dox(3') --.

UNITED STATES PATENT AND TRADEMARK OFFICE
CERTIFICATE OF CORRECTION

PATENT NO. : 5,866,679
DATED : February 2, 1999
INVENTOR(S) : Deborah DeFeo-Jones, Victor M. Garsky, Dong-Mei Feng, Raymond E. Jones and Allen I. Oliff It is certified that error appears in the above-identified patent and that said Letters Patent is hereby corrected as shown below:

In claim 2, column 165, line 55 should read:

-- Ac-(ornithine)TyrGln-SerSerSerNle-dox(3') --.

In claim 3, column 166, line 25 should read:

-- $X_L$ is absent or is an amino acid selection from: --.

In claim 3, column 166, line 35 should read:

-- $X_L$ is $-NH-(CH_2)_n-NH-$ --.

In claim 13, column 171, line 14 should read:

-- p) melphalan, --.

In claim 16, column 171, line 52 should read:

-- $X_L$ is absent or is an amino acid selected from: --.

UNITED STATES PATENT AND TRADEMARK OFFICE
CERTIFICATE OF CORRECTION

PATENT NO. : 5,866,679
DATED : February 2, 1999
INVENTOR(S) : Deborah DeFeo-Jones, Victor M. Garsky, Dong-Mei Feng, Raymond E. Jones and Allen I. Oliff It is certified that error appears in the above-identified patent and that said Letters Patent is hereby corrected as shown below:

In claim 17, column 172, line 18 should read:

-- c) GlyGluAsnGlyValGlnLysAspValSerGlnXaaSerIle --.

In claim 17, column 172, line 27 should read:

-- k) TyrGlnIseSerSer (SEQ.ID.NO.: 186);  --.

In claim 17, column 172, line 31 should read:

-- $X_L$ is absent or is an amino acid selection from:  --.

Signed and Sealed this

Seventh Day of September, 1999

Attest:

Q. TODD DICKINSON

Attesting Officer

Acting Commissioner of Patents and Trademarks